United States Patent
Li et al.

(10) Patent No.: US 11,851,469 B2
(45) Date of Patent: Dec. 26, 2023

(54) SOLUBLE HETERODIMERIC T CELL RECEPTOR, AND PREPARATION METHOD AND USE THEREOF

(71) Applicant: XLIFESC, LTD., Guangdong (CN)

(72) Inventors: Yi Li, Guangzhou (CN); Hui Fan, Guangzhou (CN)

(73) Assignee: XLIFESC, LTD., Guangdong (CN)

( * ) Notice: Subject to any disclaimer, the term of this patent is extended or adjusted under 35 U.S.C. 154(b) by 1240 days.

(21) Appl. No.: 15/524,370

(22) PCT Filed: Nov. 4, 2015

(86) PCT No.: PCT/CN2015/093806
§ 371 (c)(1),
(2) Date: Aug. 21, 2018

(87) PCT Pub. No.: WO2016/070814
PCT Pub. Date: May 12, 2016

(65) Prior Publication Data
US 2018/0355012 A1 Dec. 13, 2018

(30) Foreign Application Priority Data

Nov. 7, 2014 (CN) .......................... 201410629321.8

(51) Int. Cl.
| | |
|---|---|
| *C07K 14/725* | (2006.01) |
| *A61K 38/17* | (2006.01) |
| *C12N 15/63* | (2006.01) |
| *A61K 47/62* | (2017.01) |
| *C07K 16/28* | (2006.01) |
| *A61K 38/00* | (2006.01) |

(52) U.S. Cl.
CPC .......... *C07K 14/7051* (2013.01); *A61K 38/17* (2013.01); *A61K 47/62* (2017.08); *C07K 16/2809* (2013.01); *C12N 15/63* (2013.01); *A61K 38/00* (2013.01); *C07K 2319/30* (2013.01)

(58) Field of Classification Search
None
See application file for complete search history.

(56) References Cited

U.S. PATENT DOCUMENTS

| 8,361,794 B2 * | 1/2013 | Jakobsen .................. A61P 3/10 |
| | | 435/372.3 |
| 10,130,721 B2 | 11/2018 | Jakobsen et al. |
| 2007/0082362 A1 | 4/2007 | Jakobsen et al. |

FOREIGN PATENT DOCUMENTS

| CN | 1279690 A | 1/2001 |
| CN | 1464790 A | 12/2003 |
| CN | 100551931 C | 10/2009 |
| JP | 2007-527191 A | 9/2007 |
| WO | 2003/020763 A2 | 3/2003 |
| WO | 2004/044004 A2 | 5/2004 |
| WO | 2004/048410 A2 | 6/2004 |

OTHER PUBLICATIONS

Boulter et al, Clinical and Experimental Immunology, 142:454-460, 2005.*
George et al (TRENDS in Immunology, 26(12):653-659, 2005.*
Dolgin, Nature Biotechnology, 40:441-449, 2022.*
International Search Report (English version); PCT Appln. CN2015/093806; dated Feb. 6, 2016; 4 pages.
Extended European Search Report; EP Appln. 15857032.5; dated Mar. 13, 2018; 9 pages.
Reiter, Y. et al..; "Construction of a Functional Disulfide-Stabilized TCR FV Indicates That Antibody and TCR FV Frameworks are Very Similar in Structure"; Immunity; vol. 2, No. 3; Mar. 1, 1995; Cell Press, US; pp. 281-287.
Belmont, et al.; Potent antitumor activity of a tumor-specific soluble TCR/IL-2 fusion protein; Clinical Immunology; (2006) 121, 29-39.
Mosquera, et al.; In Vitro and In Vivo Characterization of a Novel Antibody-Like Single-Chain TCR Human IgG1 Fusion Protein; Journal of Immunology; (2005) 174:4381-4388.
Wen, et al; Targeting activity of a TCR/IL-2 fusion protein against established tumors; Cancer Immunol Immunother; (2008) 57:1781-1794.

* cited by examiner

*Primary Examiner* — Zachary S Skelding
(74) *Attorney, Agent, or Firm* — Kilpatrick Townsend & Stockton LLP

(57) ABSTRACT

Provided is a high-stability T cell receptor (TCR). The TCR comprises (i) the whole or a part of TCRα chain except a transmembrane domain thereof, and (ii) the whole or a part of TCRβ chain except a transmembrane domain thereof, both the (i) and the (ii) comprising a functional variable domain and at least a part of a constant domain of a TCR chain. An artificial interchain disulfide bond links the constant domains of the TCRα and β chains, and a Tm value of the T cell receptor is greater than or equal to 45° C.

14 Claims, 17 Drawing Sheets

Specification includes a Sequence Listing.

MGKTTQPNSMESNEEEPVHLPCNHSTISGTDYIHWYRQLPSQGPEYVIHGLTSNVNNRMASLAIAEDRKSSTLIL
HRATLRDAAVYYCILPLAGGTSYGKLTFGQGTILTVHPNIQNPDPAVYQLRDSKSSDKSVCLFTDFDSQTNVSQS
KDSDVYITDKTVLDMCSMDFKSNSAVAWSNKSDFACANAFNNSIIPEDTFFPSPESS (SEQ ID NO. :2)

FIG. 1A

MGVSQSPRYKVAKRGQDVALRCDPISGHVSLFWYQQALGQGPEFLTYFQNEAQLDKSGLPSDRFFAERPEGSVST
LKIQRTQQEDSAVYLCASSLGQAYEQYFGPGTRLTVTEDLKNVFPPEVAVFEPSEAEISHTQKATLVCLATGFYP
DHVELSWWVNGKEVHCGVSTDPQPLKEQPALNDSRYALSSRLRVSATFWQNPRNHFRCQVQFYGLSENDEWTQDR
AKPVTQIVSAEAWGRAD (SEQ ID NO. :4)

FIG. 1B

ATGGGCAAAACCACCCAGCCGAACTCAATGGAAAGCAACGAAGAAGAACCGGTCCACCTGCCGTGTAATCACAGC
ACCATCTCAGGCACCGATTATATTCATTGGTACCGTCAGCTGCCGAGCCAAGGTCCGGAATATGTGATCCACGGT
CTGACCAGTAACGTTAACAATCGTATGGCATCCCTGGCAATTGCTGAAGATCGCAAAAGCTCTACCCTGATCCTG
CATCGTGCAACGCTGCGTGACGCAGCCGTTTATTACTGCATTCTGCCGCTGGCCGGCGGTACCAGCTACGGCAAG
CTGACGTTTGGCCAGGGTACCATTCTGACGGTCCACCCGAACATCCAGAATCCGGATCCGGCCGTTTATCAGCTG
CGTGATAGCAAAAGCAGCGATAAAAGCGTGTGCCTGTTCACCGATTTTGATAGCCAGACCAACGTGAGCCAGAGC
AAAGATAGCGATGTGTACATCACCGATAAAACCGTGCTGGATATGTGCAGCATGGATTTCAAAAGCAATAGCGCG
GTTGCGTGGAGCAACAAAAGCGATTTTGCGTGCGCGAACGCGTTTAACAACAGCATCATCCCGGAAGATACGTTC
TTCCCCAGCCCAGAAAGTTCC (SEQ ID NO. :1)

FIG. 2A

ATGGGCGTGTCCCAAAGCCCGCGTTACAAAGTTGCCAAGCGTGGTCAAGATGTTGCTCTGCGTTGCGATCCGATT
AGTGGTCATGTTAGCCTGTTTTGGTATCAGCAAGCGCTGGGCCAGGGTCCGGAATTTCTGACCTACTTCCAGAAC
GAAGCACAACTGGATAAATCAGGCCTGCCGTCGGACCGTTTCTTTGCTGAACGCCCGGAAGGTAGTGTTTCCACC
CTGAAGATTCAGCGTACGCAGCAAGAAGATTCTGCGGTCTATCTGTGCGCCAGCTCTCTGGGCCAGGCGTATGAA
CAATACTTTGGTCCGGGTACGCGTCTGACCGTCACGGAAGATCTGAAAAACGTGTTTCCGCCGGAAGTTGCGGTT
TTTGAACCGAGCGAAGCGGAAATTAGCCATACCCAGAAAGCGACCCTGGTTTGTCTGGCGACCGGTTTTTATCCG
GATCATGTGGAACTGTCTTGGTGGGTGAACGGCAAAGAAGTGCATTGCGGTGTTTCTACCGATCCGCAGCCGCTG
AAAGAACAGCCGGCGCTGAATGATAGCCGTTATGCGCTGTCTAGCCGTCTGCGTGTTAGCGCGACCTTTTGGCAA
AATCCGCGTAACCATTTTCGTTGCCAGGTGCAGTTTTATGGCCTGAGCGAAAACGATGAATGGACCCAGGATCGT
GCGAAGCCGGTTACCCAGATTGTTAGCGCGGAAGCCTGGGGCCGCGCAGATTAA (SEQ ID NO. :3)

FIG. 2B

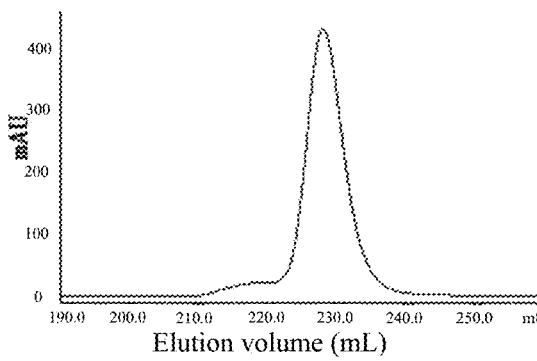

FIG. 3

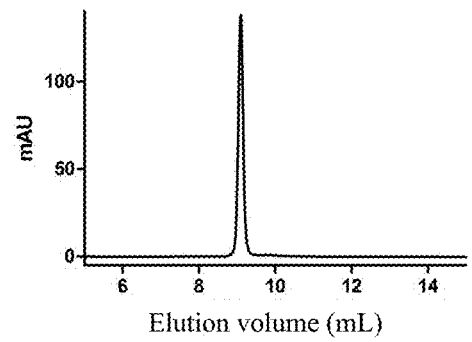

FIG. 4

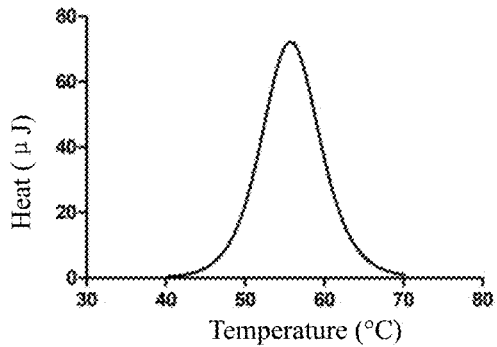

FIG. 5

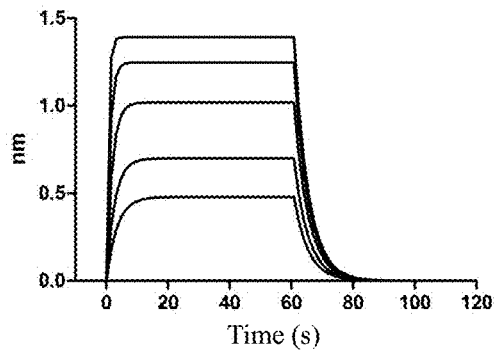

FIG. 6

MAQEVTQIPAALSVPEGENLVLNCSFTDSAIYNLQWFRQDPGKGLTSLLLIQSSQREQTSGRLNASLDKSSGRST
LYIAASQPGDSATYLCAVRPTSGGSYIPTFGRGTSLIVHPYIQNPDPAVYQLRDSKSSDKSVCLFTDFDSQTNVS
QSKDSDVYITDKTVLDMCSMDFKSNSAVAWSNKSDFACANAFNNSIIPEDTFFPSPESS (SEQ ID NO.:6)

FIG. 7A

MGVTQTPKFQVLKTGQSMTLQCAQDMNHEYMSWYRQDPGMGLRLIHYSVGAGITDQGEVPNGYNVSRSTTEDFPL
RLLSAAPSQTSVYFCASSYVGNTGELFFGEGSRLTVLEDLKNVFPPEVAVFEPSEAEISHTQKATLVCLATGFYP
DHVELSWWVNGKEVHCGVSTDPQPLKEQPALNDSRYALSSRLRVSATFWQNPRNHFRCQVQFYGLSENDEWTQDR
AKPVTQIVSAEAWGRAD (SEQ ID NO.:8)

FIG. 7B

ATGGCACAAGAAGTTACTCAAATTCCGGCGGCGCTGAGCGTTCCGGAAGGTGAAAACCTGGTGCTGAACTGCAGC
TTTACCGATAGCGCGATCTATAACCTGCAGTGGTTTCGTCAAGATCCGGGTAAAGGTCTGACCAGCCTGCTGCTG
ATTCAGAGCAGCCAGCGTGAACAGACCAGCGGTCGTCTGAATGCGAGCCTGGATAAAAGCAGCGGTCGTAGCACC
CTGTATATTGCGGCGAGCCAGCCGGGTGATAGCGCAACCTATCTGTGTGCGGTTCGTCCGACCAGCGGTGGTAGC
TATATTCCGACCTTTGGTCGTGGCACCAGCCTGATTGTGCATCCGTATATCCAGAATCCGGATCCGGCCGTTTAT
CAGCTGCGTGATAGCAAAAGCAGCGATAAAAGCGTGTGCCTGTTCACCGATTTTGATAGCCAGACCAACGTGAGC
CAGAGCAAAGATAGCGATGTGTACATCACCGATAAAACCGTGCTGGATATGTGCAGCATGGATTTCAAAAGCAAT
AGCGCGGTTGCGTGGAGCAACAAAAGCGATTTTGCGTGCGCGAACGCGTTTAACAACAGCATCATCCCGGAAGAT
ACGTTCTTCCCCAGCCCAGAAAGTTCC (SEQ ID NO.:5)

FIG. 8A

ATGGGCGTCACACAAACCCCGAAATTTCAGGTGCTGAAAACGGGTCAGAGCATGACCCTGCAGTGTGCGCAGGAT
ATGAACCACGAATACATGAGCTGGTATCGTCAAGATCCGGGTATGGGTCTGCGTCTGATCCATTATAGCGTGGGT
GCGGGCATTACCGATCAGGGTGAAGTGCCGAACGGTTATAATGTTAGCCGTAGCACCACCGAAGATTTTCCGCTG
CGTCTGCTGAGCGCGGCGCCGAGCCAGACCAGCGTTTATTTTTGCGCGAGCAGCTATGTTGGTAACACCGGCGAA
CTGTTTTTTGGTGAAGGCAGCCGTCTGACCGTTCTGGAAGATCTGAAAAACGTGTTTCCGCCGGAAGTTGCGGTT
TTTGAACCGAGCGAAGCGGAAATTAGCCATACCCAGAAAGCGACCCTGGTTTGTCTGGCGACCGGTTTTTATCCG
GATCATGTGGAACTGTCTTGGTGGGTGAACGGCAAAGAAGTGCATTGCGGTGTTTCTACCGATCCGCAGCCGCTG
AAAGAACAGCCGGCGCTGAATGATAGCCGTTATGCGCTGTCTAGCCGTCTGCGTGTTAGCGCGACCTTTTGGCAA
AATCCGCGTAACCATTTTCGTTGCCAGGTGCAGTTTTATGGCCTGAGCGAAAACGATGAATGGACCCAGGATCGT
GCGAAGCCGGTTACCCAGATTGTTAGCGCGGAAGCCTGGGGCCGCGCAGATTAA (SEQ ID NO.:7)

FIG. 8B

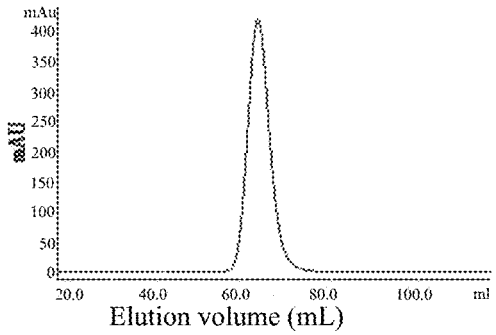

FIG. 9

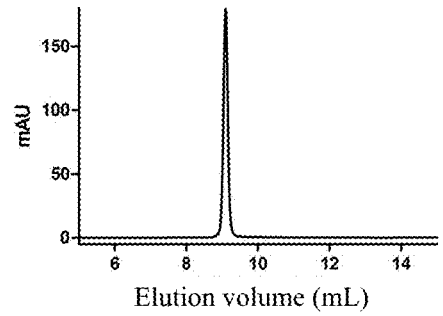

FIG. 10

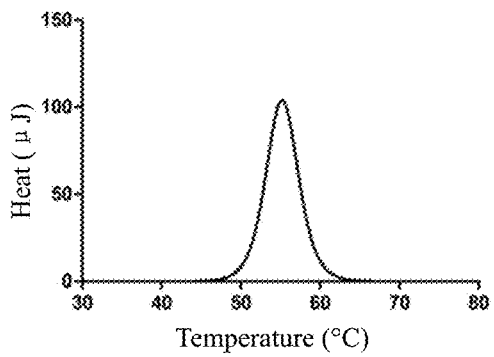

FIG. 11

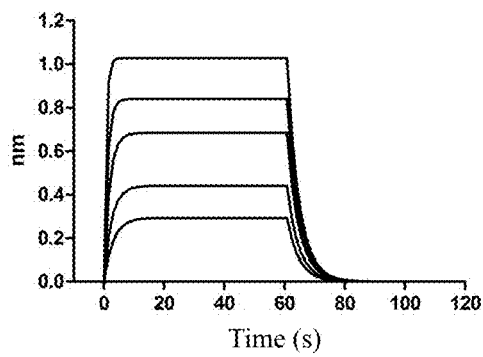

FIG. 12

MGQLLEQSPQFLSIQEGENLTVYCNSSSVFSSLQWYRQEPGEGPVLLVTVVTGGEVKKLKRLTFQFGDARKDSSL
HITAAQPGDTGLYLCAGAGSQGNLIFGKGTKLSVKPNIQNPDPAVYQLRDSKSSDKSVCLFTDFDSQTNVSQSKD
SDVYITDKTVLDMCSMDFKSNSAVAWSNKSDFACANAFNNSIIPEDTFFPSPESS (SEQ ID NO. :10)

FIG. 13A

MVDGGITQSPKYLFRKEGQNVTLSCEQNLNHDAMYWYRQDPGQGLRLIYYSQIVNDFQKGDIAEGYSVSREKKES
FPLTVTSAQKNPTAFYLCASSSRSSYEQYFGPGTRLTVTEDLKNVFPPEVAVFEPSEAEISHTQKATLVCLATGF
YPDHVELSWWVNGKEVHCGVSTDPQPLKEQPALNDSRYALSSRLRVSATFWQNPRNHFRCQVQFYGLSENDEWTQ
DRAKPVTQIVSAEAWGRAD (SEQ ID NO. :12)

FIG. 13B

ATGGGCCAACTGCTGGAACAATCCCCGCAATTCCTGAGTATTCAAGAAGGCGAAAATCTGACGGTCTACTGTAAT
TCATCATCGGTCTTTAGCTCTCTGCAGTGGTATCGTCAAGAACCGGGTGAAGGTCCGGTCCTGCTGGTGACCGTG
GTTACGGGCGGTGAAGTGAAAAAGCTGAAACGTCTGACCTTTCAGTTCGGCGATGCGCGCAAGGACAGTTCCCTG
CATATTACCGCAGCACAGCCGGGTGATACGGGTCTGTACCTGTGCGCAGGCGCTGGTAGCCAAGGTAACCTGATT
TTTGGCAAGGGTACGAAGCTGAGCGTTAAACCGAACATCCAGAATCCGGATCCGGCCGTTTATCAGCTGCGTGAT
AGCAAAAGCAGCGATAAAAGCGTGTGCCTGTTCACCGATTTTGATAGCCAGACCAACGTGAGCCAGAGCAAAGAT
AGCGATGTGTACATCACCGATAAAACCGTGCTGGATATG<u>TGC</u>AGCATGGATTTCAAAAGCAATAGCGCGGTTGCG
TGGAGCAACAAAAGCGATTTTGCGTGCGCGAACGCGTTTAACAACAGCATCATCCCGGAAGATACGTTCTTCCCC
AGCCCAGAAAGTTCC        (SEQ ID NO. :9)

FIG. 14A

ATGGTGGACGGCGGCATTACCCAAAGCCCGAAGTACCTGTTTCGCAAGGAAGGCCAAAATGTGACCCTGTCGTGT
GAACAAAATCTGAACCATGATGCGATGTATTGGTACCGTCAGGACCCGGGTCAAGGTCTGCGTCTGATTTATTAC
AGCCAGATCGTGAATGATTTTCAAAAAGGCGACATTGCAGAAGGTTATAGCGTGAGCCGTGAAAAGAAAGAATCT
TTTCCGCTGACCGTCACGTCCGCTCAGAAGAACCCGACCGCGTTCTACCTGTGCGCGAGCAGCAGCCGTAGCAGC
TATGAACAATACTTTGGTCCGGGTACGCGTCTGACCGTCACGGAAGATCTGAAAAACGTGTTTCCGCCGGAAGTT
GCGGTTTTTGAACCGAGCGAAGCGGAAATTAGCCATACCCAGAAAGCGACCCTGGTTTGTCTGGCGACCGGTTTT
TATCCGGATCATGTGGAACTGTCTTGGTGGGTGAACGGCAAAGAAGTGCATTGCGGTGTTTCTACCGATCCGCAG
CCGCTGAAAGAACAGCCGGCGCTGAATGATAGCCGTTATGCGCTGTCTAGCCGTCTGCGTGTTAGCGCGACCTTT
TGGCAAAATCCGCGTAACCATTTTCGTTGCCAGGTGCAGTTTTATGGCCTGAGCGAAAACGATGAATGGACCCAG
GATCGTGCGAAGCCGGTTACCCAGATTGTTAGCGCGGAAGCCTGGGGCCGCGCAGATTAA (SEQ ID NO.:11)

FIG. 14B

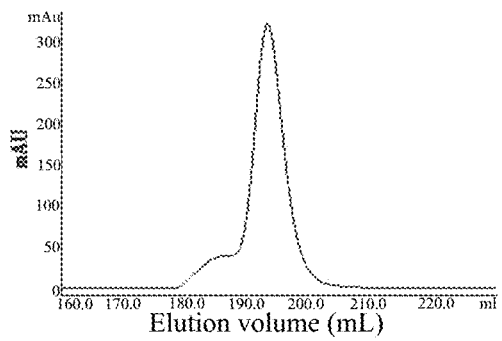

FIG. 15

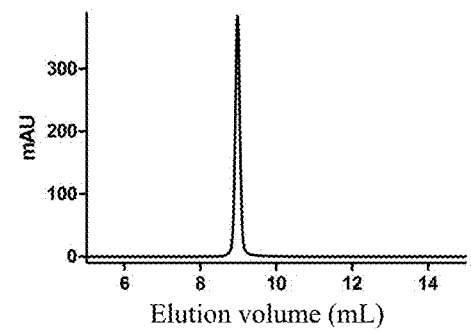

FIG. 16

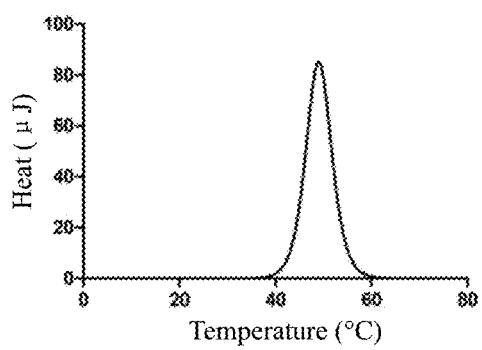

FIG. 17

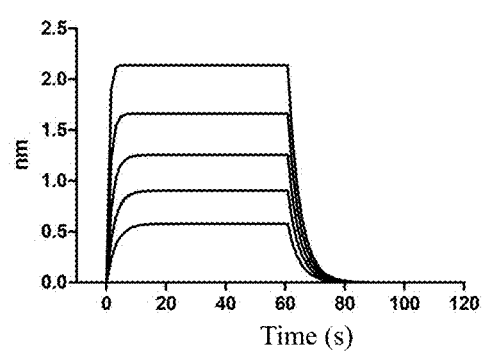

FIG. 18

MGKQEVTQIPAALSVPEGENLVLNCSFTDSAIYNLQWFRQDPGKGLTSLLLVRPYQREQTSGRLNASLDKSSGRS
TLYIAASQPGDSATYLCAVRPGGAGSYQLTFGKGTKLSVIPNIQNPDPAVYQLRDSKSSDKSVCLFTDFDSQTNV
SQSKDSDVYITDKTVLDMCSMDFKSNSAVAWSNKSDFACANAFNNSIIPEDTFFPSPESS (SEQ ID NO.:14)

FIG. 19A

MGKAGVTQTPRYLIKTRGQQVTLSCSPISGHRSVSWYQQTPGQGLQFLFEYFSETQRNKGNFPGRFSGRQFSNSR
SEMNVSTLELGDSALYLCASSPNMADEQYFGPGTRLTVTEDLKNVFPPEVAVFEPSEAEISHTQKATLVCLATGF
YPDHVELSWWVNGKEVHCGVSTDPQPLKEQPALNDSRYALSSRLRVSATFWQNPRNHFRCQVQFYGLSENDEWTQ
DRAKPVTQIVSAEAWGRAD (SEQ ID NO.:16)

FIG. 19B

ATGGGTAAGCAGGAAGTGACCCAGATCCCTGCCGCCCTGAGCGTGCCCGAGGGCGAGAACCTGGTGCTGAACTGC
AGCTTCACCGACAGCGCCATCTACAACCTGCAGTGGTTCCGGCAGGACCCCGGCAAGGGCCTGACCAGCCTGCTG
CTGGTGCGTCCGTATCAGCGGGAGCAGACCAGCGGCAGACTGAACGCCAGCCTGGACAAGAGCAGCGGCAGAAGC
ACCCTGTATATCGCCGCCAGCCAGCCCGGCGACTCCGCCACCTACCTGTGCGCTGTGCGGCCTGGCGGAGCCGGC
AGCTACCAGCTGACCTTCGGCAAGGGCACCAAGCTGTCCGTGATCCCCAATATCCAGAATCCGGATCCGGCCGTT
TATCAGCTGCGTGATAGCAAAAGCAGCGATAAAAGCGTGTGCCTGTTCACCGATTTTGATAGCCAGACCAACGTG
AGCCAGAGCAAAGATAGCGATGTGTACATCACCGATAAAACCGTGCTGGATATGTGCAGCATGGATTTCAAAAGC
AATAGCGCGGTTGCGTGGAGCAACAAAAGCGATTTTGCGTGCGCGAACGCGTTTAACAACAGCATCATCCCGGAA
GATACGTTCTTCCCCAGCCCAGAAAGTTCC(SEQ ID NO.:13)

FIG. 20A

ATGGGTAAAGCTGGAGTTACTCAAACTCCAAGATATCTGATCAAAACGAGAGGACAGCAAGTGACACTGAGCTGC
TCCCCTATCTCTGGGCATAGGAGTGTATCCTGGTACCAACAGACCCCAGGACAGGGCCTTCAGTTCCTCTTTGAA
TACTTCAGTGAGACACAGAGAAACAAAGGAAACTTCCCTGGTCGATTCTCAGGGCGCCAGTTCTCTAACTCTCGC
TCTGAGATGAATGTGAGCACCTTGGAGCTGGGGGACTCGGCCCTTTATCTTTGCGCCAGCAGCCCGAACATGGCC
GACGAGCAGTACTTCGGGCCGGGCACCAGGCTCACGGTCACAGAAGATCTGAAAAACGTGTTTCCGCCGGAAGTT
GCGGTTTTGAACCGAGCGAAGCGGAAATTAGCCATACCCAGAAAGCGACCCTGGTTTGTCTGGCGACCGGTTTT
TATCCGGATCATGTGGAACTGTCTTGGTGGGTGAACGGCAAGGAAGTGCATTGCGGTGTTTCTACCGATCCGCAG
CCGCTGAAAGAACAGCCGGCGCTGAATGATAGCCGTTATGCGCTGTCTAGCCGTCTGCGTGTTAGCGCGACCTTT
TGGCAAAATCCGCGTAACCATTTTCGTTGCCAGGTGCAGTTTTATGGCCTGAGCGAAAACGATGAATGGACCCAG
GATCGTGCGAAGCCGGTTACCCAGATTGTTAGCGCGGAAGCCTGGGGCCGCGCAGATTAA(SEQ ID NO.:15)

FIG. 20B

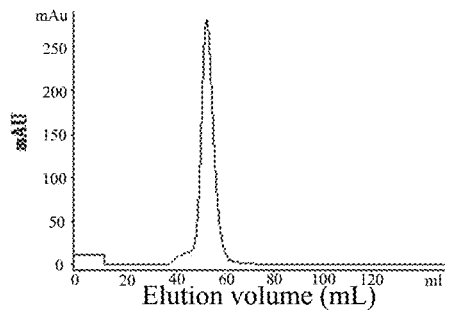

FIG. 21

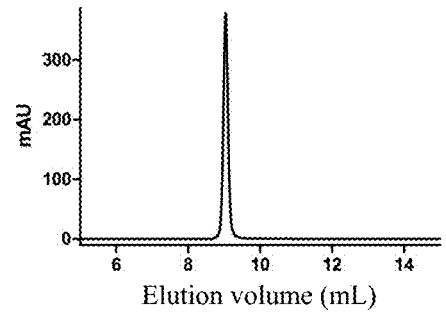

FIG. 22

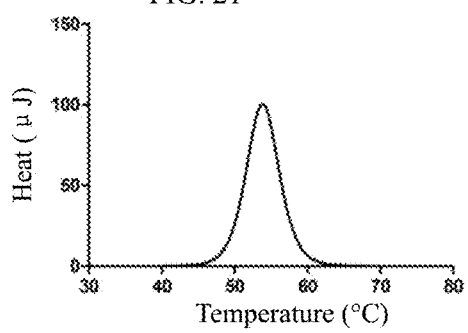

FIG. 23

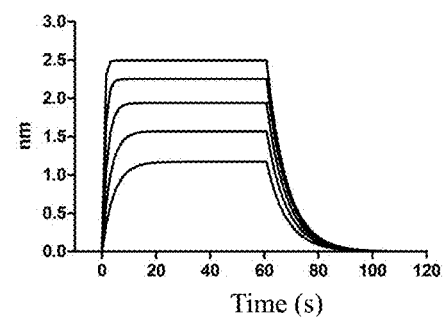

FIG. 24

MGKTTQPNSMESNEEEPVHLPCNHSTISGTDYIHWYRQLPSQGPEYVIHGLTSNVNNRMASLAIAEDRKSSTLIL
HRATLRDAAVYYCILPLAGGTSYGKLTFGQGTILTVHPNIQNPDPAVYQLRDSKSSDKSVCLFTDFDSQTNVSQS
KDSDVYITDKTVLDMRSMDFKSNSAVAWSNKSDFACANAFNNSIIPEDTFFCSPESS
(SEQ ID NO.:18)

FIG. 25A

MGVSQSPRYKVAKRGQDVALRCDPISGHVSLFWYQQALGQGPEFLTYFQNEAQLDKSGLPSDRFFAERPEGSVST
LKIQRTQQEDSAVYLCASSLGQAYEQYFGPGTRLTVTEDLKNVFPPPEVAVFEPSE<u>C</u>EISHTQKATLVCLATGFYP
DHVELSWWVNGKEVHSGVSTDPQPLKEQPALNDSRYALSSRLRVSATFWQNPRNHFRCQVQFYGLSENDEWTQDR
AKPVTQIVSAEAWGRAD (SEQ ID NO.:20)

FIG. 25B

ATGGGCAAAACCACCCAGCCGAACTCAATGGAAAGCAACGAAGAAGAACCGGTCCACCTGCCGTGTAATCACAGC
ACCATCTCAGGCACCGATTATATTCATTGGTACCGTCAGCTGCCGAGCCAAGGTCCGGAATATGTGATCCACGGT
CTGACCAGTAACGTTAACAATCGTATGGCATCCCTGGCAATTGCTGAAGATCGCAAAAGCTCTACCCTGATCCTG
CATCGTGCAACGCTGCGTGACGCAGCCGTTTATTACTGCATTCTGCCGCTGGCCGGCGGTACCAGCTACGGCAAG
CTGACGTTTGGCCAGGGTACCATTCTGACGGTCCACCCGAATATCCAGAATCCGGATCCGGCCGTTTATCAGCTG
CGTGATAGCAAAAGCAGCGATAAAAGCGTGTGCCTGTTCACCGATTTTGATAGCCAGACCAACGTGAGCCAGAGC
AAAGATAGCGATGTGTACATCACCGATAAAACCGTGCTGGATATGCGCAGCATGGATTTCAAAAGCAATAGCGCG
GTTGCGTGGAGCAACAAAAGCGATTTTGCGTGCGCGAACGCGTTTAACAACAGCATCATCCCGGAAGATACGTTC
TTC<u>TGC</u>AGCCCAGAAAGTTCC     (SEQ ID NO.:17)

FIG. 26A

ATGGGCGTGTCCCAAAGCCCGCGTTACAAAGTTGCCAAGCGTGGTCAAGATGTTGCTCTGCGTTGCGATCCGATT
AGTGGTCATGTTAGCCTGTTTTGGTATCAGCAAGCGCTGGGCCAGGGTCCGGAATTTCTGACCTACTTCCAGAAC
GAAGCACAACTGGATAAATCAGGCCTGCCGTCGGACCGTTTCTTTGCTGAACGCCCGGAAGGTAGTGTTTCCACC
CTGAAGATTCAGCGTACGCAGCAAGAAGATTCTGCGGTCTATCTGTGCGCCAGCTCTCTGGGCCAGGCGTATGAA
CAATACTTTGGTCCGGGTACGCGTCTGACCGTCACGGAAGATCTGAAAAACGTGTTTCCGCCGGAAGTTGCGGTT
TTTGAACCGAGCGAA<u>TGC</u>GAAATTAGCCATACCCAGAAAGCGACCCTGGTTTGTCTGGCGACCGGTTTTTATCCG
GATCATGTGGAACTGTCTTGGTGGGTGAACGGCAAAGAAGTGCATAGCGGTGTTTCTACCGATCCGCAGCCGCTG
AAAGAACAGCCGGCGCTGAATGATAGCCGTTATGCGCTGTCTAGCCGTCTGCGTGTTAGCGCGACCTTTTGGCAA
AATCCGCGTAACCATTTTCGTTGCCAGGTGCAGTTTTATGGCCTGAGCGAAAACGATGAATGGACCCAGGATCGT
GCGAAGCCGGTTACCCAGATTGTTAGCGCGGAAGCCTGGGGCCGCGCAGATTAA (SEQ ID NO.:19)

FIG. 26B

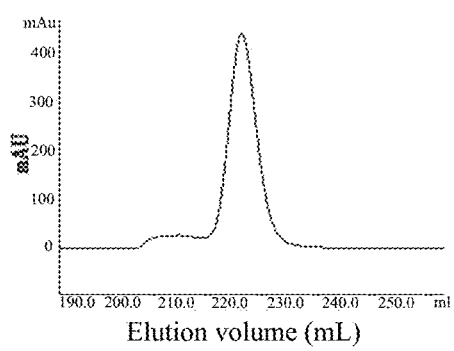

FIG. 27

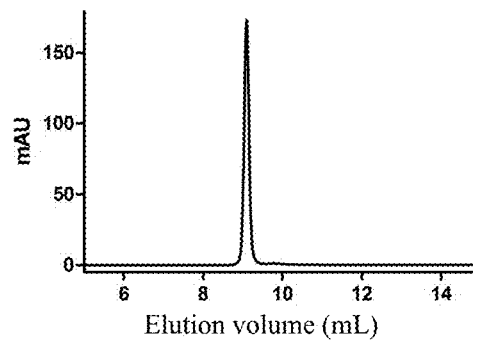

FIG. 28

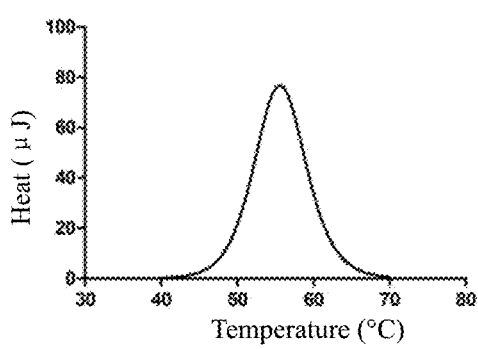

FIG. 29

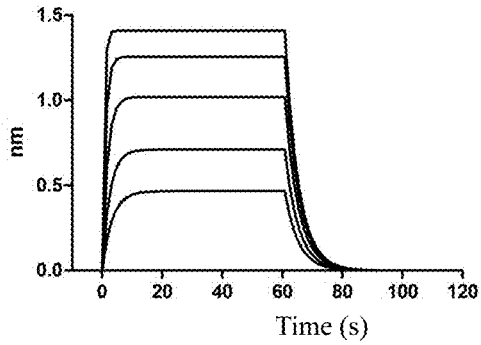

FIG. 30

MAQEVTQIPAALSVPEGENLVLNCSFTDSAIYNLQWFRQDPGKGLTSLLLIQSSQREQTSGRLNASLDKSSGRST
LYIAASQPGDSATYLCAVRPTSGGSYIPTFGRGTSLIVHPYIQNPDPAVYQLRDSKSSDKSVCLFTDFDSQTNVS
QSKDSDVYITDKTVLDMRSMDFKSNSAVAWSNKSDFACANAFNNSIIPEDTFF<u>C</u>SPESS(SEQ ID NO. :22)

FIG. 31A

MGVTQTPKFQVLKTGQSMTLQCAQDMNHEYMSWYRQDPGMGLRLIHYSVGAGITDQGEVPNGYNVSRSTTEDFPL
RLLSAAPSQTSVYFCASSYVGNTGELFFGEGSRLTVLEDLKNVFPPEVAVFEPSE<u>C</u>EISHTQKATLVCLATGFYP
DHVELSWWVNGKEVHSGVSTDPQPLKEQPALNDSRYALSSRLRVSATFWQNPRNHFRCQVQFYGLSENDEWTQDR
AKPVTQIVSAEAWGRAD(SEQ ID NO. :24)

FIG. 31B

ATGGCACAAGAAGTTACTCAAATTCCGGCGGCGCTGAGCGTTCCGGAAGGTGAAAACCTGGTGCTGAACTGCAGC
TTTACCGATAGCGCGATCTATAACCTGCAGTGGTTTCGTCAAGATCCGGGTAAAGGTCTGACCAGCCTGCTGCTG
ATTCAGAGCAGCCAGCGTGAACAGACCAGCGGTCGTCTGAATGCGAGCCTGGATAAAAGCAGCGGTCGTAGCACC
CTGTATATTGCGGCGAGCCAGCCGGGTGATAGCGCAACCTATCTGTGTGCGGTTCGTCCGACCAGCGGTGGTAGC
TATATTCCGACCTTTGGTCGTGGCACCAGCCTGATTGTGCATCCGTATATCCAGAATCCGGATCCGGCCGTTTAT
CAGCTGCGTGATAGCAAAAGCAGCGATAAAAGCGTGTGCCTGTTCACCGATTTTGATAGCCAGACCAACGTGAGC
CAGAGCAAAGATAGCGATGTGTACATCACCGATAAAACCGTGCTGGATATGCGCAGCATGGATTTCAAAAGCAAT
AGCGCGGTTGCGTGGAGCAACAAAAGCGATTTTGCGTGCGCGAACGCGTTTAACAACAGCATCATCCCGGAAGAT
ACGTTCTTC<u>TGC</u>AGCCCAGAAAGTTCC(SEQ ID NO. :21)

FIG. 32A

ATGGGCGTCACACAAACCCCGAAATTTCAGGTGCTGAAAACGGGTCAGAGCATGACCCTGCAGTGTGCGCAGGAT
ATGAACCACGAATACATGAGCTGGTATCGTCAAGATCCGGGTATGGGTCTGCGTCTGATCCATTATAGCGTGGGT
GCGGGCATTACCGATCAGGGTGAAGTGCCGAACGGTTATAATGTTAGCCGTAGCACCACCGAAGATTTTCCGCTG
CGTCTGCTGAGCGCGGCGCCGAGCCAGACCAGCGTTTATTTTTGCGCGAGCAGCTATGTTGGTAACACCGGCGAA
CTGTTTTTTGGTGAAGGCAGCCGTCTGACCGTTCTGGAAGATCTGAAAAACGTGTTTCCGCCGGAAGTTGCGGTT
TTTGAACCGAGCGAA<u>TGC</u>GAAATTAGCCATACCCAGAAAGCGACCCTGGTTTGTCTGGCGACCGGTTTTTATCCG
GATCATGTGGAACTGTCTTGGTGGGTGAACGGCAAAGAAGTGCATAGCGGTGTTTCTACCGATCCGCAGCCGCTG
AAAGAACAGCCGGCGCTGAATGATAGCCGTTATGCGCTGTCTAGCCGTCTGCGTGTTAGCGCGACCTTTTGGCAA
AATCCGCGTAACCATTTTCGTTGCCAGGTGCAGTTTTATGGCCTGAGCGAAAACGATGAATGGACCCAGGATCGT
GCGAAGCCGGTTACCCAGATTGTTAGCGCGGAAGCCTGGGGCCGCGCAGATTAA(SEQ ID NO. :23)

FIG. 32B

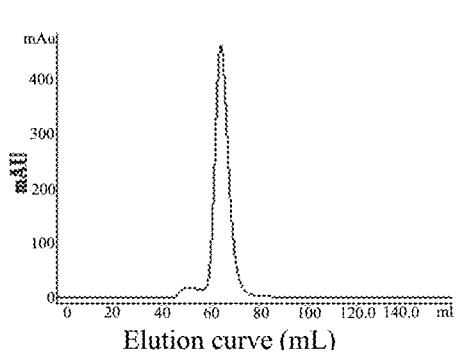

Elution curve (mL)

FIG. 33

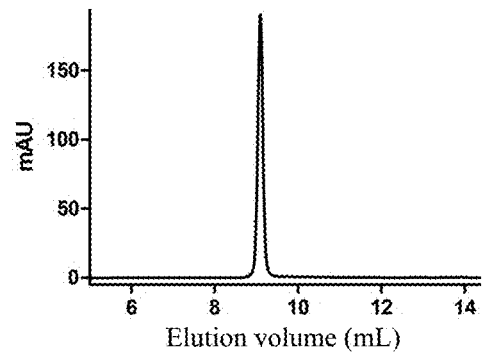

Elution volume (mL)

FIG. 34

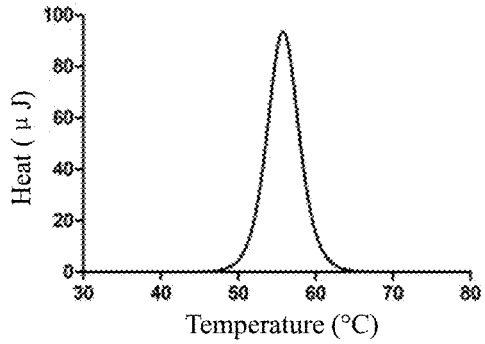

FIG. 35

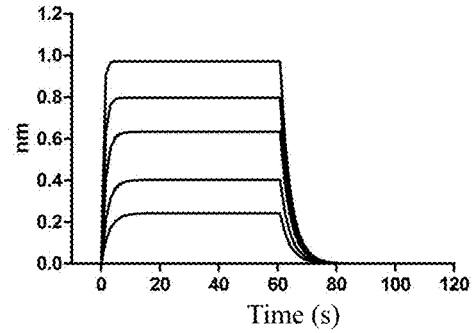

FIG. 36

MGQLLEQSPQFLSIQEGENLTVYCNSSSVFSSLQWYRQEPGEGPVLLVTVVTGGEVKKLKRLTFQFGDARKDSSL
HITAAQPGDTGLYLCAGAGSQGNLIFGKGTKLSVKPNIQNPDPAVYQLRDSKSSDKSVCLFTDFDSQTNVSQSKD
SDVYITDKTVLDMRSMDFKSNSAVAWSNKSDFACANAFNNSIIPEDTFF<u>C</u>SPESS (SEQ ID NO.:26)

FIG. 37A

MVDGGITQSPKYLFRKEGQNVTLSCEQNLNHDAMYWYRQDPGQGLRLIYYSQIVNDFQKGDIAEGYSVSREKKES
FPLTVTSAQKNPTAFYLCASSSRSSYEQYFGPGTRLTVTEDLKNVFPPEVAVFEPSE<u>CE</u>ISHTQKATLVCLATGF
YPDHVELSWWVNGKEVHSGVSTDPQPLKEQPALNDSRYALSSRLRVSATFWQNPRNHFRCQVQFYGLSENDEWTQ
DRAKPVTQIVSAEAWGRAD (SEQ ID NO.:28)

FIG. 37B

ATGGGCCAACTGCTGGAACAATCCCCGCAATTCCTGAGTATTCAAGAAGGCGAAAATCTGACGGTCTACTGTAAT
TCATCATCGGTCTTTAGCTCTCTGCAGTGGTATCGTCAAGAACCGGGTGAAGGTCCGGTCCTGCTGGTGACCGTG
GTTACGGGCGGTGAAGTGAAAAAGCTGAAACGTCTGACCTTTCAGTTCGGCGATGCGCGCAAGGACAGTTCCCTG
CATATTACCGCAGCACAGCCGGGTGATACGGGTCTGTACCTGTGCGCAGGCGCTGGTAGCCAAGGTAACCTGATT
TTTGGCAAGGGTACGAAGCTGAGCGTTAAACCGAACATCCAGAATCCGGATCCGGCCGTTTATCAGCTGCGTGAT
AGCAAAAGCAGCGATAAAAGCGTGTGCCTGTTCACCGATTTTGATAGCCAGACCAACGTGAGCCAGAGCAAAGAT
AGCGATGTGTACATCACCGATAAAACCGTGCTGGATATGCGCAGCATGGATTTCAAAAGCAATAGCGCGGTTGCG
TGGAGCAACAAAAGCGATTTTGCGTGCGCGAACGCGTTTAACAACAGCATCATCCCGGAAGATACGTTCTTC<u>TGC</u>
AGCCCAGAAAGTTCC (SEQ ID NO.:25)

FIG. 38A

ATGGTGGACGGCGGCATTACCCAAAGCCCGAAGTACCTGTTTCGCAAGGAAGGCCAAAATGTGACCCTGTCGTGT
GAACAAAATCTGAACCATGATGCGATGTATTGGTACCGTCAGGACCCGGGTCAAGGTCTGCGTCTGATTTATTAC
AGCCAGATCGTGAATGATTTTCAAAAGGCGACATTGCAGAAGGTTATAGCGTGAGCCGTGAAAAGAAAGAATCT
TTTCCGCTGACCGTCACGTCCGCTCAGAAGAACCCGACCGCGTTCTACCTGTGCGCGAGCAGCAGCCGTAGCAGC
TATGAACAATACTTTGGTCCGGGTACGCGTCTGACCGTCACGGAAGATCTGAAAAACGTGTTTCCGCCGGAAGTT
GCGGTTTTTGAACCGAGCGAA<u>TGC</u>GAAATTAGCCATACCCAGAAAGCGACCCTGGTTTGTCTGGCGACCGGTTTT
TATCCGGATCATGTGGAACTGTCTTGGTGGGTGAACGGCAAAGAAGTGCATAGCGGTGTTTCTACCGATCCGCAG
CCGCTGAAAGAACAGCCGGCGCTGAATGATAGCCGTTATGCGCTGTCTAGCCGTCTGCGTGTTAGCGCGACCTTT
TGGCAAAATCCGCGTAACCATTTTCGTTGCCAGGTGCAGTTTATGGCCTGAGCGAAAACGATGAATGGACCCAG
GATCGTGCGAAGCCGGTTACCCAGATTGTTAGCGCGGAAGCCTGGGGCCGCGCAGATTAA (SEQ ID NO.:27)

FIG. 38B

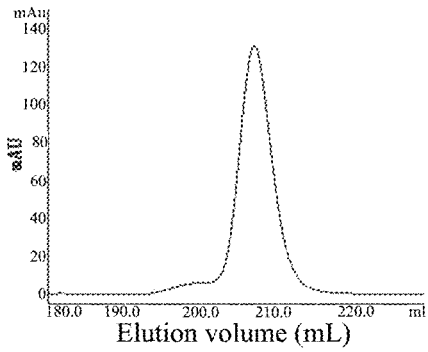

FIG. 39

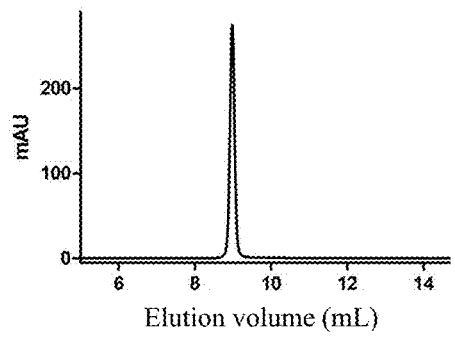

FIG. 40

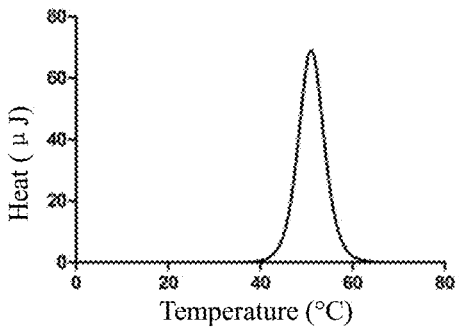

FIG. 41

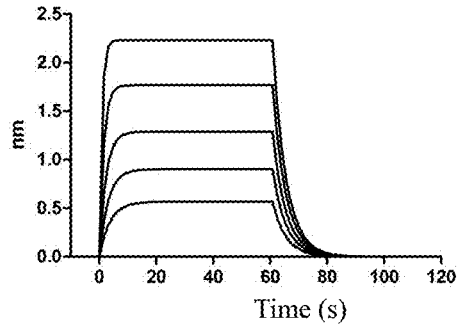

FIG. 42

MGKQEVTQIPAALSVPEGENLVLNCSFTDSAIYNLQWFRQDPGKGLTSLLLVRPYQREQTSGRLNASLDKSSGRS
TLYIAASQPGDSATYLCAVRPGGAGSYQLTFGKGTKLSVIPNIQNPDPAVYQLRDSKSSDKSVCLFTDFDSQTNV
SQSKDSDVYITDKTVLDMRSMDFKSNSAVAWSNKSDFACANAFNNSIIPEDTFF<u>C</u>SPESS (SEQ ID NO.:30)

FIG. 43A

MGKAGVTQTPRYLIKTRGQQVTLSCSPISGHRSVSWYQQTPGQGLQFLFEYFSETQRNKGNFPGRFSGRQFSNSR
SEMNVSTLELGDSALYLCASSPNMADEQYFGPGTRLTVTEDLKNVFPPEVAVFEPSE<u>C</u>EISHTQKATLVCLATGF
YPDHVELSWWVNGKEVHSGVSTDPQPLKEQPALNDSRYALSSRLRVSATFWQNPRN<u>H</u>FRCQVQFYGLSENDEWTQ
DRAKPVTQIVSAEAWGRAD (SEQ ID NO.:32)

FIG. 43B

ATGGGTAAGCAGGAAGTGACCCAGATCCCTGCCGCCCTGAGCGTGCCCGAGGGCGAGAACCTGGTGCTGAACTGC
AGCTTCACCGACAGCGCCATCTACAACCTGCAGTGGTTCCGGCAGGACCCCGGCAAGGGCCTGACCAGCCTGCTG
CTGGTGCGTCCGTATCAGCGGGAGCAGACCAGCGGCAGACTGAACGCCAGCCTGGACAAGAGCAGCGGCAGAAGC
ACCCTGTATATCGCCGCCAGCCAGCCCGGCGACTCCGCCACCTACCTGTGCGCTGTGCGGCCTGGCGGAGCCGGC
AGCTACCAGCTGACCTTCGGCAAGGGCACCAAGCTGTCCGTGATCCCCAATATCCAGAATCCGGATCCGGCCGTT
TATCAGCTGCGTGATAGCAAAAGCAGCGATAAAAGCGTGTGCCTGTTCACCGATTTTGATAGCCAGACCAACGTG
AGCCAGAGCAAAGATAGCGATGTGTACATCACCGATAAAACCGTGCTGGATATGCGCAGCATGGATTTCAAAAGC
AATAGCGCGGTTGCGTGGAGCAACAAAAGCGATTTTGCGTGCGCGAACGCGTTTAACAACAGCATCATCCCGGAA
GATACGTTCTTC<u>TGC</u>AGCCCAGAAAGTTCC (SEQ ID NO.:29)

FIG. 44A

ATGGGTAAAGCTGGAGTTACTCAAACTCCAAGATATCTGATCAAAACGAGAGGACAGCAAGTGACACTGAGCTGC
TCCCCTATCTCTGGGCATAGGAGTGTATCCTGGTACCAACAGACCCCAGGACAGGGCCTTCAGTTCCTCTTTGAA
TACTTCAGTGAGACACAGAGAAACAAAGGAAACTTCCCTGGTCGATTCTCAGGGCGCCAGTTCTCTAACTCTCGC
TCTGAGATGAATGTGAGCACCTTGGAGCTGGGGGACTCGGCCCTTTATCTTTGCGCCAGCAGCCCGAACATGGCC
GACGAGCAGTACTTCGGGCCGGGCACCAGGCTCACGGTCACAGAAGATCTGAAAAACGTGTTTCCGCCGGAAGTT
GCGGTTTTTGAACCGAGCGAA<u>TGC</u>GAAATTAGCCATACCCAGAAAGCGACCCTGGTTTGTCTGGCGACCGGTTTT
TATCCGGATCATGTGGAACTGTCTTGGTGGGTGAACGGCAAAGAAGTGCATAGCGGTGTTTCTACCGATCCGCAG
CCGCTGAAAGAACAGCCGGCGCTGAATGATAGCCGTTATGCGCTGTCTAGCCGTCTGCGTGTTAGCGCGACCTTT
TGGCAAAATCCGCGTAACCATTTTCGTTGCCAGGTGCAGTTTTATGGCCTGAGCGAAAACGATGAATGGACCCAG
GATCGTGCGAAGCCGGTTACCCAGATTGTTAGCGCGGAAGCCTGGGGCCGCGCAGATTAA(SEQ ID NO.:31)

FIG. 44B

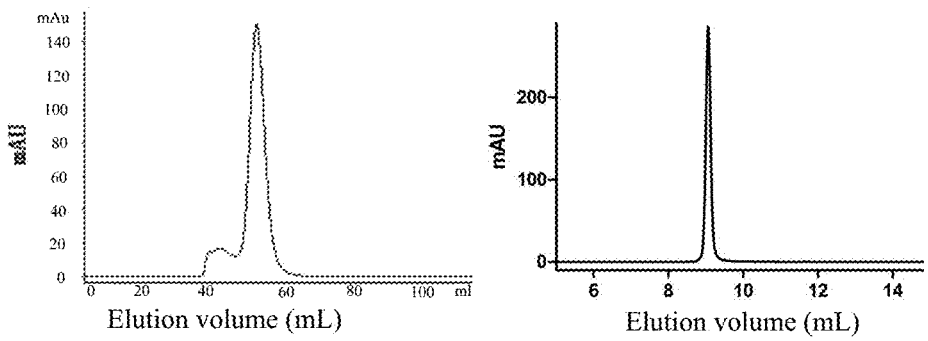

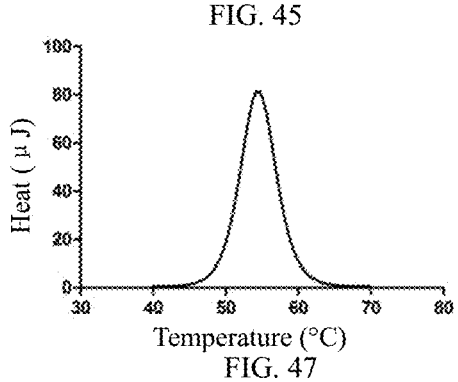

FIG. 47

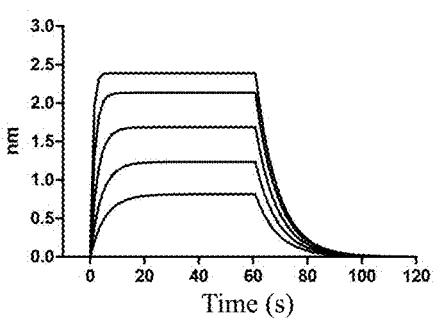

FIG. 48

MGKTTQPNSMESNEEEPVHLPCNHSTISGTDYIHWYRQLPSQGPEYVIHGLTSNVNNRMASLAIAEDRKSSTLIL
HRATLRDAAVYYCILPLAGGTSYGKLTFGQGTILTVHPNIQNPDPAV<u>C</u>QLRDSKSSDKSVCLFTDFDSQTNVSQS
KDSDVYITDKTVLDMRSMDFKSNSAVAWSNKSDFACANAFNNSIIPEDTFFPSPESS
(SEQ ID NO.:34)

FIG. 49A

MGVSQSPRYKVAKRGQDVALRCDPISGHVSLFWYQQALGQGPEFLTYFQNEAQLDKSGLPSDRFFAERPEGSVST
LKIQRTQQEDSAVYLCASSLGQAYEQYFGPGTRLTVTEDLKNVFPPEVAVFEPSEA<u>C</u>ISHTQKATLVCLATGFYP
DHVELSWWVNGKEVHSGVSTDPQPLKEQPALNDSRYALSSRLRVSATFWQNPRNHFRCQVQFYGLSENDEWTQDR
AKPVTQIVSAEAWGRAD(SEQ ID NO.:36)

FIG. 49B

ATGGGCAAAACCACCCAGCCGAACTCAATGGAAAGCAACGAAGAAGAACCGGTCCACCTGCCGTGTAATCACAGC
ACCATCTCAGGCACCGATTATATTCATTGGTACCGTCAGCTGCCGAGCCAAGGTCCGGAATATGTGATCCACGGT
CTGACCAGTAACGTTAACAATCGTATGGCATCCCTGGCAATTGCTGAAGATCGCAAAAGCTCTACCCTGATCCTG
CATCGTGCAACGCTGCGTGACGCAGCCGTTTATTACTGCATTCTGCCGCTGGCCGGCGGTACCAGCTACGGCAAG
CTGACGTTTGGCCAGGGTACCATTCTGACGGTCCACCCGAACATCCAGAATCCGGATCCGGCCGTT<u>TGC</u>CAGCTG
CGTGATAGCAAAAGCAGCGATAAAAGCGTGTGCCTGTTCACCGATTTTGATAGCCAGACCAACGTGAGCCAGAGC
AAAGATAGCGATGTGTACATCACCGATAAAACCGTGCTGGATATGCGCAGCATGGATTTCAAAAGCAATAGCGCG
GTTGCGTGGAGCAACAAAAGCGATTTTGCGTGCGCGAACGCGTTTAACAACAGCATCATCCCGGAAGATACGTTC
TTCCCCAGCCCAGAAAGTTCC (SEQ ID NO.:33)

FIG. 50A

ATGGGCGTGTCCCAAAGCCCGCGTTACAAAGTTGCCAAGCGTGGTCAAGATGTTGCTCTGCGTTGCGATCCGATT
AGTGGTCATGTTAGCCTGTTTTGGTATCAGCAAGCGCTGGGCCAGGGTCCGGAATTTCTGACCTACTTCCAGAAC
GAAGCACAACTGGATAAATCAGGCCTGCCGTCGGACCGTTTCTTTGCTGAACGCCCGGAAGGTAGTGTTTCCACC
CTGAAGATTCAGCGTACGCAGCAAGAAGATTCTGCGGTCTATCTGTGCGCCAGCTCTCTGGGCCAGGCGTATGAA
CAATACTTTGGTCCGGGTACGCGTCTGACCGTCACGGAAGATCTGAAAAACGTGTTTCCGCCGGAAGTTGCGGTT
TTTGAACCGAGCGAAGCG<u>TGC</u>ATTAGCCATACCCAGAAAGCGACCCTGGTTTGTCTGGCGACCGGTTTTTATCCG
GATCATGTGGAACTGTCTTGGTGGGTGAACGGCAAAGAAGTGCATAGCGGTGTTTCTACCGATCCGCAGCCGCTG
AAAGAACAGCCGGCGCTGAATGATAGCCGTTATGCGCTGTCTAGCCGTCTGCGTGTTAGCGCGACCTTTTGGCAA
AATCCGCGTAACCATTTTCGTTGCCAGGTGCAGTTTTATGGCCTGAGCGAAAACGATGAATGGACCCAGGATCGT
GCGAAGCCGGTTACCCAGATTGTTAGCGCGGAAGCCTGGGGCCGCGCAGATTAA(SEQ ID NO.:35)

FIG. 50B

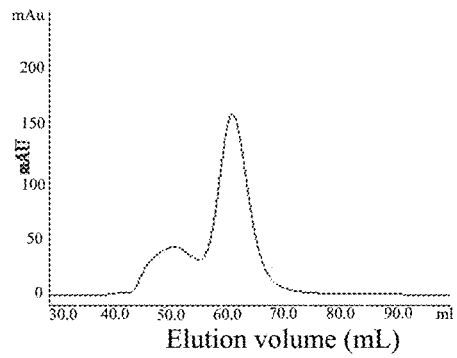

FIG. 51

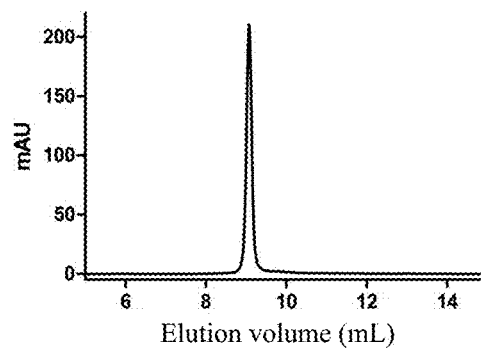

FIG. 52

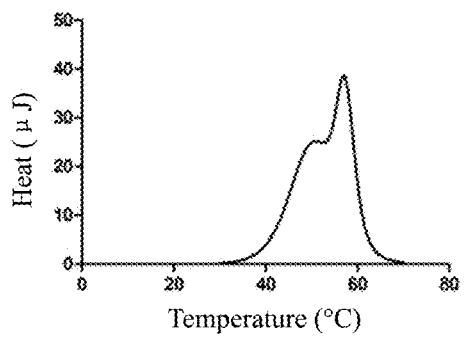

FIG. 53

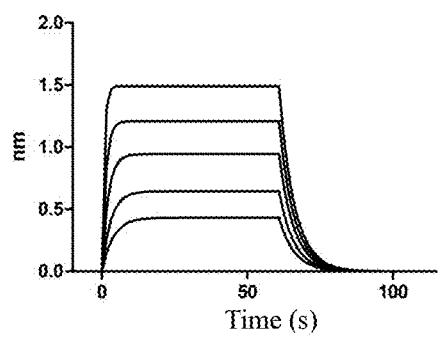

FIG. 54

MAQEVTQIPAALSVPEGENLVLNCSFTDSAIYNLQWFRQDPGKGLTSLLLIQSSQREQTSGRLNASLDKSSGRST
LYIAASQPGDSATYLCAVRPTSGGSYIPTFGRGTSLIVHPYIQNPDPAVCQLRDSKSSDKSVCLFTDFDSQTNVS
QSKDSDVYITDKTVLDMRSMDFKSNSAVAWSNKSDFACANAFNNSIIPEDTFFPSPESS (SEQ ID NO.:38)

FIG. 55A

MGVTQTPKFQVLKTGQSMTLQCAQDMNHEYMSWYRQDPGMGLRLIHYSVGAGITDQGEVPNGYNVSRSTTEDFPL
RLLSAAPSQTSVYFCASSYVGNTGELFFGEGSRLTVLEDLKNVFPPEVAVFEPSEACISHTQKATLVCLATGFYP
DHVELSWWVNGKEVHSGVSTDPQPLKEQPALNDSRYALSSRLRVSATFWQNPRNHFRCQVQFYGLSENDEWTQDR
AKPVTQIVSAEAWGRAD (SEQ ID NO.:40)

FIG. 55B

ATGGCACAAGAAGTTACTCAAATTCCGGCGGCGCTGAGCGTTCCGGAAGGTGAAAACCTGGTGCTGAACTGCAGC
TTTACCGATAGCGCGATCTATAACCTGCAGTGGTTTCGTCAAGATCCGGGTAAAGGTCTGACCAGCCTGCTGCTG
ATTCAGAGCAGCCAGCGTGAACAGACCAGCGGTCGTCTGAATGCGAGCCTGGATAAAAGCAGCGGTCGTAGCACC
CTGTATATTGCGGCGAGCCAGCCGGGTGATAGCGCAACCTATCTGTGTGCGGTTCGTCCGACCAGCGGTGGTAGC
TATATTCCGACCTTTGGTCGTGGCACCAGCCTGATTGTGCATCCGTATATCCAGAATCCGGATCCGGCCGTTTGC
CAGCTGCGTGATAGCAAAAGCAGCGATAAAAGCGTGTGCCTGTTCACCGATTTTGATAGCCAGACCAACGTGAGC
CAGAGCAAAGATAGCGATGTGTACATCACCGATAAAACCGTGCTGGATATGCGCAGCATGGATTTCAAAAGCAAT
AGCGCGGTTGCGTGGAGCAACAAAAGCGATTTTGCGTGCGCGAACGCGTTTAACAACAGCATCATCCCGGAAGAT
ACGTTCTTCCCCAGCCCAGAAAGTTCC (SEQ ID NO.:37)

FIG. 56A

ATGGGCGTCACACAAACCCCGAAATTTCAGGTGCTGAAAACGGGTCAGAGCATGACCCTGCAGTGTGCGCAGGAT
ATGAACCACGAATACATGAGCTGGTATCGTCAAGATCCGGGTATGGGTCTGCGTCTGATCCATTATAGCGTGGGT
GCGGGCATTACCGATCAGGGTGAAGTGCCGAACGGTTATAATGTTAGCCGTAGCACCACCGAAGATTTTCCGCTG
CGTCTGCTGAGCGCGGCGCCGAGCCAGACCAGCGTTTATTTTTGCGCGAGCAGCTATGTTGGTAACACCGGCGAA
CTGTTTTTTGGTGAAGGCAGCCGTCTGACCGTTCTGGAAGATCTGAAAAACGTGTTTCCGCCGGAAGTTGCGGTT
TTTGAACCGAGCGAAGCGTGCATTAGCCATACCCAGAAAGCGACCCTGGTTTGTCTGGCGACCGGTTTTTATCCG
GATCATGTGGAACTGTCTTGGTGGGTGAACGGCAAAGAAGTGCATAGCGGTGTTTCTACCGATCCGCAGCCGCTG
AAAGAACAGCCGGCGCTGAATGATAGCCGTTATGCGCTGTCTAGCCGTCTGCGTGTTAGCGCGACCTTTTGGCAA
AATCCGCGTAACCATTTTCGTTGCCAGGTGCAGTTTATGGCCTGAGCGAAAACGATGAATGGACCCAGGATCGT
GCGAAGCCGGTTACCCAGATTGTTAGCGCGGAAGCCTGGGGCCGCGCAGATTAA (SEQ ID NO.:39)

FIG. 56B

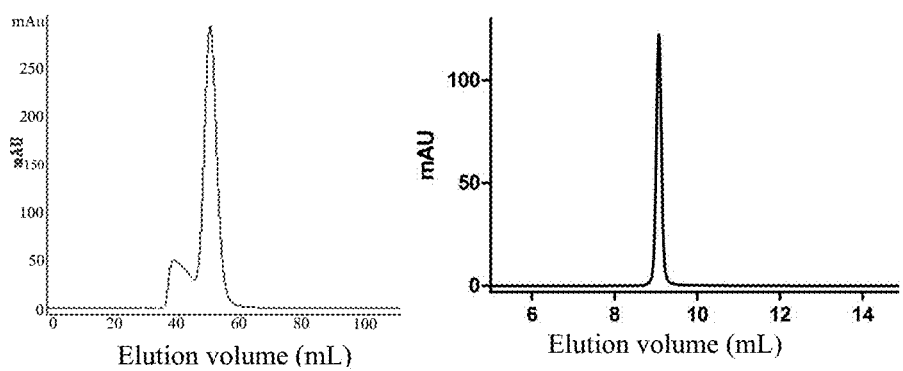

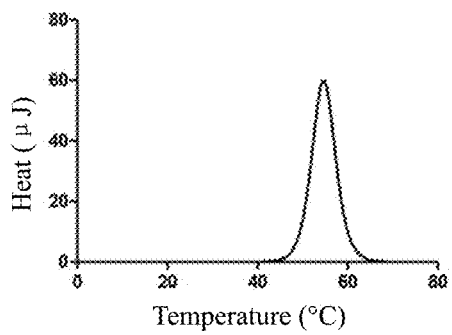

FIG. 59

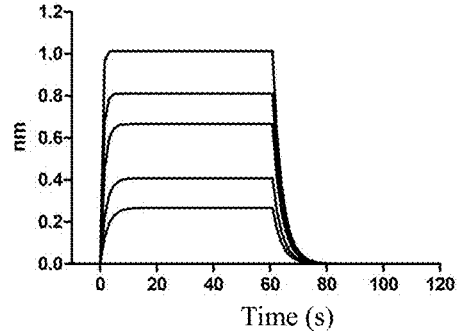

FIG. 60

MGQLLEQSPQFLSIQEGENLTVYCNSSSVFSSLQWYRQEPGEGPVLLVTVVTGGEVKKLKRLTFQFGDARKDSSL
HITAAQPGDTGLYLCAGAGSQGNLIFGKGTKLSVKPNIQNPDPAVCQLRDSKSSDKSVCLFTDFDSQTNVSQSKD
SDVYITDKTVLDMRSMDFKSNSAVAWSNKSDFACANAFNNSIIPEDTFFPSPESS (SEQ ID NO. :42)

FIG. 61A

MVDGGITQSPKYLFRKEGQNVTLSCEQNLNHDAMYWYRQDPGQGLRLIYYSQIVNDFQKGDIAEGYSVSREKKES
FPLTVTSAQKNPTAFYLCASSSRSSYEQYFGPGTRLTVTEDLKNVFPPPEVAVFEPSEACISHTQKATLVCLATGF
YPDHVELSWWVNGKEVHSGVSTDPQPLKEQPALNDSRYALSSRLRVSATFWQNPRNHFRCQVQFYGLSENDEWTQ
DRAKPVTQIVSAEAWGRAD (SEQ ID NO. :44)

FIG. 61B

ATGGGCCAACTGCTGGAACAATCCCCGCAATTCCTGAGTATTCAAGAAGGCGAAAATCTGACGGTCTACTGTAAT
TCATCATCGGTCTTTAGCTCTCTGCAGTGGTATCGTCAAGAACCGGGTGAAGGTCCGGTCCTGCTGGTGACCGTG
GTTACGGGCGGTGAAGTGAAAAAGCTGAAACGTCTGACCTTTCAGTTCGGCGATGCGCGCAAGGACAGTTCCCTG
CATATTACCGCAGCACAGCCGGGTGATACGGGTCTGTACCTGTGCGCAGGCGCTGGTAGCCAAGGTAACCTGATT
TTTGGCAAGGGTACGAAGCTGAGCGTTAAACCGAACATCCAGAATCCGGATCCGGCCGTTTGCCAGCTGCGTGAT
AGCAAAAGCAGCGATAAAAGCGTGTGCCTGTTCACCGATTTTGATAGCCAGACCAACGTGAGCCAGAGCAAAGAT
AGCGATGTGTACATCACCGATAAAACCGTGCTGGATATGCGCAGCATGGATTTCAAAAGCAATAGCGCGGTTGCG
TGGAGCAACAAAAGCGATTTTGCGTGCGCGAACGCGTTTAACAACAGCATCATCCCGGAAGATACGTTCTTCCCC
AGCCCAGAAAGTTCC (SEQ ID NO. :41)

FIG. 62A

ATGGTGGACGGCGGCATTACCCAAAGCCCGAAGTACCTGTTTCGCAAGGAAGGCCAAAATGTGACCCTGTCGTGT
GAACAAAATCTGAACCATGATGCGATGTATTGGTACCGTCAGGACCCGGGTCAAGGTCTGCGTCTGATTTATTAC
AGCCAGATCGTGAATGATTTTCAAAAAGGCGACATTGCAGAAGGTTATAGCGTGAGCCGTGAAAAGAAAGAATCT
TTTCCGCTGACCGTCACGTCCGCTCAGAAGAACCCGACCGCGTTCTACCTGTGCGCGAGCAGCAGCCGTAGCAGC
TATGAACAATACTTTGGTCCGGGTACGCGTCTGACCGTCACGGAAGATCTGAAAAACGTGTTTCCGCCGGAAGTT
GCGGTTTTTGAACCGAGCGAAGCGTGCATTAGCCATACCCAGAAAGCGACCCTGGTTTGTCTGGCGACCGGTTTT
TATCCGGATCATGTGGAACTGTCTTGGTGGGTGAACGGCAAAGAAGTGCATAGCGGTGTTTCTACCGATCCGCAG
CCGCTGAAAGAACAGCCGGCGCTGAATGATAGCCGTTATGCGCTGTCTAGCCGTCTGCGTGTTAGCGCGACCTTT
TGGCAAAATCCGCGTAACCATTTTCGTTGCCAGGTGCAGTTTTATGGCCTGAGCGAAAACGATGAATGGACCCAG
GATCGTGCGAAGCCGGTTACCCAGATTGTTAGCGCGGAAGCCTGGGGCCGCGCAGATTAA (SEQ ID NO. :43)

FIG. 62B

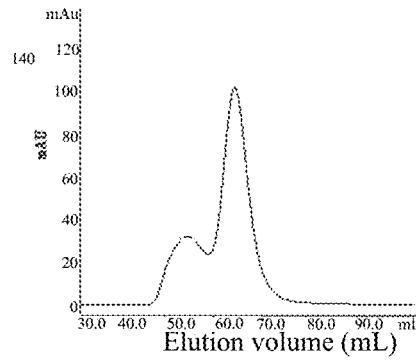

FIG. 63

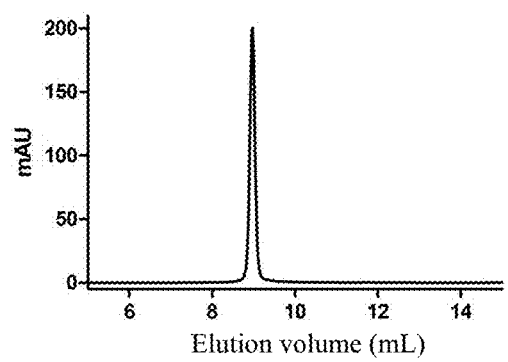

FIG. 64

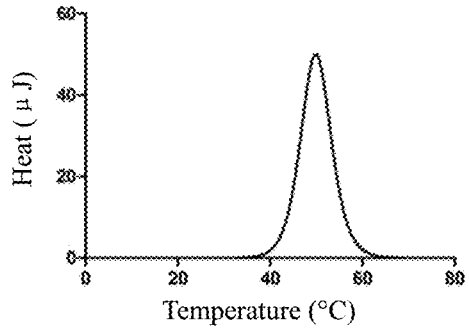

FIG. 65

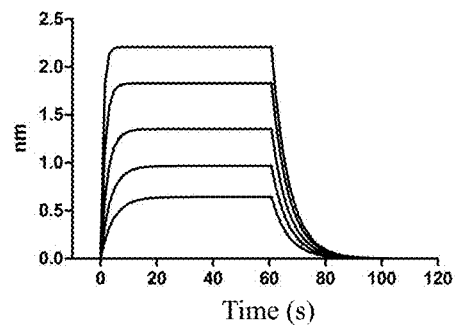

FIG. 66

MGKQEVTQIPAALSVPEGENLVLNCSFTDSAIYNLQWFRQDPGKGLTSLLLVRPYQREQTSGRLNASLDKSSGRS
TLYIAASQPGDSATYLCAVRPGGAGSYQLTFGKGTKLSVIPNIQNPDPAVCQLRDSKSSDKSVCLFTDFDSQTNV
SQSKDSDVYITDKTVLDMRSMDFKSNSAVAWSNKSDFACANAFNNSIIPEDTFFPSPESS (SEQ ID NO.:46)

FIG. 67A

MGKAGVTQTPRYLIKTRGQQVTLSCSPISGHRSVSWYQQTPGQGLQFLFEYFSETQRNKGNFPGRFSGRQFSNSR
SEMNVSTLELGDSALYLCASSPNMADEQYFGPGTRLTVTEDLKNVFPPEVAVFEPSEACISHTQKATLVCLATGF
YPDHVELSWWVNGKEVHSGVSTDPQPLKEQPALNDSRYALSSRLRVSATFWQNPRNHFRCQVQFYGLSENDEWTQ
DRAKPVTQIVSAEAWGRAD (SEQ ID NO.:48)

FIG. 67B

ATGGGTAAGCAGGAAGTGACCCAGATCCCTGCCGCCCTGAGCGTGCCCGAGGGCGAGAACCTGGTGCTGAACTGC
AGCTTCACCGACAGCGCCATCTACAACCTGCAGTGGTTCCGGCAGGACCCCGGCAAGGGCCTGACCAGCCTGCTG
CTGGTGCGTCCGTATCAGCGGGAGCAGACCAGCGGCAGACTGAACGCCAGCCTGGACAAGAGCAGCGGCAGAAGC
ACCCTGTATATCGCCGCCAGCCAGCCCGGCGACTCCGCCACCTACCTGTGCGCTGTGCGGCCTGGCGGAGCCGGC
AGCTACCAGCTGACCTTCGGCAAGGGCACCAAGCTGTCCGTGATCCCCAATATCCAGAATCCGGATCCGGCCGTT
TGCCAGCTGCGTGATAGCAAAAGCAGCGATAAAAGCGTGTGCCTGTTCACCGATTTTGATAGCCAGACCAACGTG
AGCCAGAGCAAAGATAGCGATGTGTACATCACCGATAAAACCGTGCTGGATATGCGCAGCATGGATTTCAAAAGC
AATAGCGCGGTTGCGTGGAGCAACAAAAGCGATTTTGCGTGCGCGAACGCGTTTAACAACAGCATCATCCCGGAA
GATACGTTCTTCCCCAGCCCAGAAAGTTCC (SEQ ID NO.:45)

FIG. 68A

ATGGGTAAAGCTGGAGTTACTCAAACTCCAAGATATCTGATCAAAACGAGAGGACAGCAAGTGACACTGAGCTGC
TCCCCTATCTCTGGGCATAGGAGTGTATCCTGGTACCAACAGACCCCAGGACAGGGCCTTCAGTTCCTCTTTGAA
TACTTCAGTGAGACACAGAGAAACAAAGGAAACTTCCCTGGTCGATTCTCAGGGCGCCAGTTCTCTAACTCTCGC
TCTGAGATGAATGTGAGCACCTTGGAGCTGGGGGACTCGGCCCTTTATCTTTGCGCCAGCAGCCCGAACATGGCC
GACGAGCAGTACTTCGGGCCGGGCACCAGGCTCACGGTCACAGAAGATCTGAAAAACGTGTTTCCGCCGGAAGTT
GCGGTTTTTGAACCGAGCGAAGCGTGCATTAGCCATACCCAGAAAGCGACCCTGGTTTGTCTGGCGACCGGTTTT
TATCCGGATCATGTGGAACTGTCTTGGTGGGTGAACGGCAAAGAAGTGCATAGCGGTGTTTCTACCGATCCGCAG
CCGCTGAAAGAACAGCCGGCGCTGAATGATAGCCGTTATGCGCTGTCTAGCCGTCTGCGTGTTAGCGCGACCTTT
TGGCAAAATCCGCGTAACCATTTTCGTTGCCAGGTGCAGTTTTATGGCCTGAGCGAAAACGATGAATGGACCCAG
GATCGTGCGAAGCCGGTTACCCAGATTGTTAGCGCGGAAGCCTGGGGCCGCGCAGATTAA (SEQ ID NO. :47)

FIG. 68B

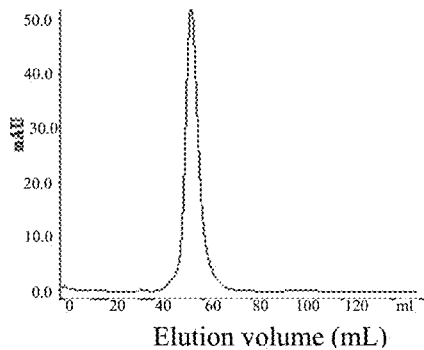

Elution volume (mL)
FIG. 69

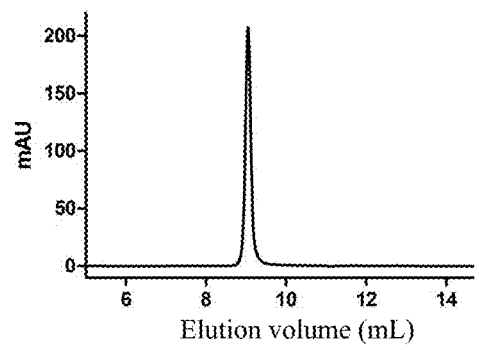

Elution volume (mL)
FIG. 70

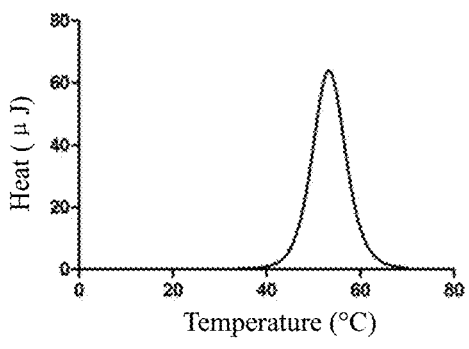

Temperature (°C)
FIG. 71

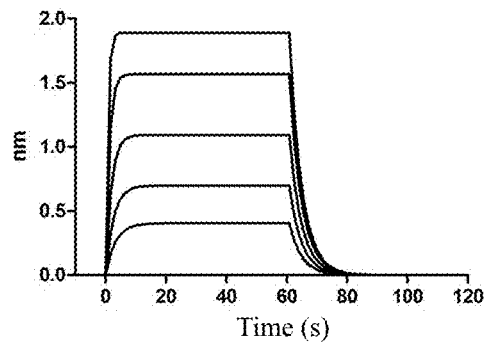

Time (s)
FIG. 72

SEQUENCE LISTING

```
<160> NUMBER OF SEQ ID NOS: 79

<210> SEQ ID NO 1
<211> LENGTH: 621
<212> TYPE: DNA
<213> ORGANISM: Artificial Sequence
<220> FEATURE:
<223> OTHER INFORMATION: Synthetic Polyribonucleotide

<400> SEQUENCE: 1
atgggcaaaa ccacccagcc gaactcaatg gaaagcaacg aagaagaacc ggtccacctg      60
ccgtgtaatc acagcaccat ctcaggcacc gattatattc attggtaccg tcagctgccg     120
agccaaggtc cggaatatgt gatccacggt ctgaccagta acgttaacaa tcgtatggca     180
tccctggcaa ttgctgaaga tcgcaaaagc tctaccctga tcctgcatcg tgcaacgctg     240
cgtgacgcag ccgtttatta ctgcattctg ccgctggccg gcggtaccag ctacggcaag     300
ctgacgtttg gccagggtac cattctgacg gtccacccga acatccagaa tccggatccg     360
gccgtttatc agctgcgtga tagcaaaagc agcgataaaa gcgtgtgcct gttcaccgat     420
tttgatagcc agaccaacgt gagccagagc aaagatagcg atgtgtacat caccgataaa     480
accgtgctgg atatgtgcag catggatttc aaaagcaata gcgcggttgc gtggagcaac     540
aaaagcgatt ttgcgtgcgc gaacgcgttt aacaacagca tcatcccgga agatacgttc     600
ttccccagcc cagaaagttc c                                               621

<210> SEQ ID NO 2
<211> LENGTH: 207
<212> TYPE: PRT
<213> ORGANISM: Artificial Sequence
<220> FEATURE:
<223> OTHER INFORMATION: Synthetic Polypeptide

<400> SEQUENCE: 2

Met Gly Lys Thr Thr Gln Pro Asn Ser Met Glu Ser Asn Glu Glu Glu
1               5                  10                  15

Pro Val His Leu Pro Cys Asn His Ser Thr Ile Ser Gly Thr Asp Tyr
            20                  25                  30

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ala Thr Leu
65                  70                  75                  80
```

Arg Asp Ala Ala Val Tyr Tyr Cys Ile Leu Pro Leu Ala Gly Gly Thr
                85                  90                  95

Ser Tyr Gly Lys Leu Thr Phe Gly Gln Gly Thr Ile Leu Thr Val His
        100                 105                 110

Pro Asn Ile Gln Asn Pro Asp Pro Ala Val Tyr Gln Leu Arg Asp Ser
        115                 120                 125

Lys Ser Ser Asp Lys Ser Val Cys Leu Phe Thr Asp Phe Asp Ser Gln
        130                 135                 140

Thr Asn Val Ser Gln Ser Lys Asp Ser Asp Val Tyr Ile Thr Asp Lys
145                 150                 155                 160

Thr Val Leu Asp Met Cys Ser Met Asp Phe Lys Ser Asn Ser Ala Val
                165                 170                 175

Ala Trp Ser Asn Lys Ser Asp Phe Ala Cys Ala Asn Ala Phe Asn Asn
            180                 185                 190

Ser Ile Ile Pro Glu Asp Thr Phe Phe Pro Ser Pro Glu Ser Ser
            195                 200                 205

<210> SEQ ID NO 3
<211> LENGTH: 729
<212> TYPE: DNA
<213> ORGANISM: Artificial Sequence
<220> FEATURE:
<223> OTHER INFORMATION: Synthetic Polyribonucleotide

<400> SEQUENCE: 3
atgggcgtgt cccaaagccc gcgttacaaa gttgccaagc gtggtcaaga tgttgctctg      60
cgttgcgatc cgattagtgg tcatgttagc ctgttttggt atcagcaagc gctgggccag     120
ggtccggaat tctgaccta cttccagaac gaagcacaac tggataaatc aggcctgccg     180
tcggaccgtt tctttgctga acgcccggaa ggtagtgttt ccaccctgaa gattcagcgt     240
acgcagcaag aagattctgc ggtctatctg tgcgccagct ctctgggcca ggcgtatgaa     300
caatactttg gtccgggtac gcgtctgacc gtcacggaag atctgaaaaa cgtgtttccg     360
ccggaagttg cggtttttga accgagcgaa gcggaaatta gccataccca gaaagcgacc     420
ctggtttgtc tggcgaccgg ttttatccg gatcatgtgg aactgtcttg gtgggtgaac     480
ggcaaagaag tgcattgcgg tgtttctacc gatccgcagc cgctgaaaga cagccggcg     540 ctgaatgata gccgttatgc gctgtctagc cgtctgcgtg ttagcgcgac cttttggcaa     600
aatccgcgta accatttttcg ttgccaggta cagttttatg gcctgagcga aaacgatgaa     660
tggacccagg atcgtgcgaa gccggttacc cagattgtta gcgcggaagc ctggggccgc     720
gcagattaa                                                             729

<210> SEQ ID NO 4
<211> LENGTH: 242
<212> TYPE: PRT
<213> ORGANISM: Artificial Sequence
<220> FEATURE:
<223> OTHER INFORMATION: Synthetic Polypeptide

<400> SEQUENCE: 4

Met Gly Val Ser Gln Ser Pro Arg Tyr Lys Val Ala Lys Arg Gly Gln
1               5                   10                  15

Asp Val Ala Leu Arg Cys Asp Pro Ile Ser Gly His Val Ser Leu Phe
            20                  25                  30

Trp Tyr Gln Gln Ala Leu Gly Gln Gly Pro Glu Phe Leu Thr Tyr Phe
        35                  40                  45

```
Gln Asn Glu Ala Gln Leu Asp Lys Ser Gly Leu Pro Ser Asp Arg Phe
     50                  55                  60

Phe Ala Glu Arg Pro Glu Gly Ser Val Ser Thr Leu Lys Ile Gln Arg
 65                  70                  75                  80

Thr Gln Gln Glu Asp Ser Ala Val Tyr Leu Cys Ala Ser Ser Leu Gly
                 85                  90                  95

Gln Ala Tyr Glu Gln Tyr Phe Gly Pro Gly Thr Arg Leu Thr Val Thr
            100                 105                 110

Glu Asp Leu Lys Asn Val Phe Pro Pro Glu Val Ala Val Phe Glu Pro
            115                 120                 125

Ser Glu Ala Glu Ile Ser His Thr Gln Lys Ala Thr Leu Val Cys Leu
130                 135                 140

Ala Thr Gly Phe Tyr Pro Asp His Val Glu Leu Ser Trp Trp Val Asn
145                 150                 155                 160

Gly Lys Glu Val His Cys Gly Val Ser Thr Asp Pro Gln Pro Leu Lys
                165                 170                 175

Glu Gln Pro Ala Leu Asn Asp Ser Arg Tyr Ala Leu Ser Ser Arg Leu
            180                 185                 190

Arg Val Ser Ala Thr Phe Trp Gln Asn Pro Arg Asn His Phe Arg Cys
            195                 200                 205

Gln Val Gln Phe Tyr Gly Leu Ser Glu Asn Asp Glu Trp Thr Gln Asp
            210                 215                 220

Arg Ala Lys Pro Val Thr Gln Ile Val Ser Ala Glu Ala Trp Gly Arg
225                 230                 235                 240

Ala Asp

<210> SEQ ID NO 5
<211> LENGTH: 627
<212> TYPE: DNA
<213> ORGANISM: Artificial Sequence
<220> FEATURE:
<223> OTHER INFORMATION: Synthetic Polyribonucleotide

<400> SEQUENCE: 5
atggcacaag aagttactca aattccggcg gcgctgagcg ttccggaagg tgaaaacctg    60
gtgctgaact gcagctttac cgatagcgcg atctataacc tgcagtggtt cgtcaagat   120 ccgggtaaag gtctgaccag cctgctgctg attcagagca gccagcgtga acagaccagc   180
ggtcgtctga atgcgagcct ggataaaagc agcggtcgta gcaccctgta tattgcggcg   240
agccagccgg gtgatagcgc aacctatctg tgtgcggttc gtccgaccag cggtggtagc   300
tatattccga ccttttggtcg tggcaccagc ctgattgtgc atccgtatat ccagaatccg   360
gatccggccg tttatcagct gcgtgatagc aaaagcagcg ataaaagcgt gtgcctgttc   420
accgattttg atagccagac caacgtgagc cagagcaaag atagcgatgt gtacatcacc   480
gataaaaccg tgctggatat tgcagcatg gatttcaaaa gcaatagcgc ggttgcgtgg   540
agcaacaaaa gcgattttgc gtgcgcgaac gcgtttaaca cagcatcat cccggaagat   600 acgttcttcc ccagcccaga aagttcc                                       627

<210> SEQ ID NO 6
<211> LENGTH: 209
<212> TYPE: PRT
<213> ORGANISM: Artificial Sequence
<220> FEATURE:
<223> OTHER INFORMATION: Synthetic Polypeptide
```

```
<400> SEQUENCE: 6

Met Ala Gln Glu Val Thr Gln Ile Pro Ala Ala Leu Ser Val Pro Glu
1               5                   10                  15

Gly Glu Asn Leu Val Leu Asn Cys Ser Phe Thr Asp Ser Ala Ile Tyr
                20                  25                  30

Asn Leu Gln Trp Phe Arg Gln Asp Pro Gly Lys Gly Leu Thr Ser Leu
            35                  40                  45

Leu Leu Ile Gln Ser Ser Gln Arg Glu Gln Thr Ser Gly Arg Leu Asn
    50                  55                  60

Ala Ser Leu Asp Lys Ser Ser Gly Arg Ser Thr Leu Tyr Ile Ala Ala
65                  70                  75                  80

Ser Gln Pro Gly Asp Ser Ala Thr Tyr Leu Cys Ala Val Arg Pro Thr
                85                  90                  95

Ser Gly Gly Ser Tyr Ile Pro Thr Phe Gly Arg Gly Thr Ser Leu Ile
                100                 105                 110

Val His Pro Tyr Ile Gln Asn Pro Asp Pro Ala Val Tyr Gln Leu Arg
            115                 120                 125

Asp Ser Lys Ser Ser Asp Lys Ser Val Cys Leu Phe Thr Asp Phe Asp
    130                 135                 140

Ser Gln Thr Asn Val Ser Gln Ser Lys Asp Ser Asp Val Tyr Ile Thr
145                 150                 155                 160

Asp Lys Thr Val Leu Asp Met Cys Ser Met Asp Phe Lys Ser Asn Ser
                165                 170                 175

Ala Val Ala Trp Ser Asn Lys Ser Asp Phe Ala Cys Ala Asn Ala Phe
            180                 185                 190

Asn Asn Ser Ile Ile Pro Glu Asp Thr Phe Phe Pro Ser Pro Glu Ser
        195                 200                 205

Ser

<210> SEQ ID NO 7
<211> LENGTH: 729
<212> TYPE: PRT
<213> ORGANISM: Artificial Sequence
<220> FEATURE:
<223> OTHER INFORMATION: Synthetic Polyribonucleotide

<400> SEQUENCE: 7

Ala Thr Gly Gly Gly Cys Gly Thr Cys Ala Cys Ala Cys Ala Ala Ala
1               5                   10                  15

Cys Cys Cys Cys Gly Ala Ala Thr Thr Cys Ala Gly Gly Thr
                20                  25                  30

Gly Cys Thr Gly Ala Ala Ala Cys Gly Gly Gly Thr Cys Ala Gly
        35                  40                  45

Ala Gly Cys Ala Thr Gly Ala Cys Cys Cys Thr Gly Cys Ala Gly Thr
    50                  55                  60

Gly Thr Gly Cys Gly Cys Ala Gly Gly Ala Thr Ala Thr Gly Ala Ala
65                  70                  75                  80

Cys Cys Ala Cys Gly Ala Ala Thr Ala Cys Ala Thr Gly Ala Gly Cys
                85                  90                  95

Thr Gly Gly Thr Ala Thr Cys Gly Thr Cys Ala Ala Gly Ala Thr Cys
                100                 105                 110

Cys Gly Gly Gly Thr Ala Thr Gly Gly Gly Cys Thr Gly Cys Gly
            115                 120                 125

Thr Cys Thr Gly Ala Thr Cys Cys Ala Thr Thr Ala Thr Ala Gly Cys
    130                 135                 140
```

-continued

Gly Thr Gly Gly Gly Thr Gly Cys Gly Gly Cys Ala Thr Thr Ala
145                 150                 155                 160

Cys Cys Gly Ala Thr Cys Ala Gly Gly Thr Gly Ala Ala Gly Thr
                165                 170                 175

Gly Cys Cys Gly Ala Ala Cys Gly Gly Thr Ala Thr Ala Ala Thr
            180                 185                 190

Gly Thr Thr Ala Gly Cys Cys Gly Thr Ala Gly Cys Ala Cys Cys Ala
            195                 200                 205

Cys Cys Gly Ala Ala Gly Ala Thr Thr Thr Cys Gly Cys Thr
        210                 215                 220

Gly Cys Gly Thr Cys Thr Gly Cys Thr Gly Ala Gly Cys Gly Cys Gly
225                 230                 235                 240

Gly Cys Gly Cys Cys Gly Ala Gly Cys Ala Gly Ala Cys Cys Ala
            245                 250                 255

Gly Cys Gly Thr Thr Thr Ala Thr Thr Thr Thr Gly Cys Gly Cys
            260                 265                 270

Gly Ala Gly Cys Ala Gly Cys Thr Ala Thr Gly Thr Thr Gly Gly Thr
        275                 280                 285

Ala Ala Cys Ala Cys Cys Gly Gly Cys Gly Ala Ala Cys Thr Gly Thr
290                 295                 300

Thr Thr Thr Thr Thr Gly Gly Thr Gly Ala Ala Gly Gly Cys Ala Gly
305                 310                 315                 320

Cys Cys Gly Thr Cys Thr Gly Ala Cys Cys Gly Thr Thr Cys Thr Gly
            325                 330                 335

Gly Gly Ala Ala Gly Ala Thr Cys Thr Gly Ala Ala Ala Ala Cys Gly
            340                 345                 350

Thr Gly Thr Thr Thr Cys Cys Gly Cys Cys Gly Gly Ala Ala Gly Thr
        355                 360                 365

Thr Gly Cys Gly Gly Thr Thr Thr Thr Thr Gly Ala Ala Cys Cys Gly
        370                 375                 380

Ala Gly Cys Gly Ala Ala Gly Cys Gly Gly Ala Ala Ala Thr Thr Ala
385                 390                 395                 400

Gly Cys Cys Ala Thr Ala Cys Cys Ala Gly Ala Ala Ala Gly Cys
            405                 410                 415

Gly Ala Cys Cys Cys Thr Gly Gly Thr Thr Thr Gly Thr Cys Thr Gly
            420                 425                 430

Gly Cys Gly Ala Cys Cys Gly Gly Thr Thr Thr Thr Ala Thr Cys
        435                 440                 445

Cys Gly Gly Ala Thr Cys Ala Thr Gly Thr Gly Gly Ala Ala Cys Thr
450                 455                 460

Gly Thr Cys Thr Thr Gly Gly Thr Gly Gly Gly Thr Gly Ala Ala Cys
465                 470                 475                 480

Gly Gly Cys Ala Ala Ala Gly Ala Ala Gly Thr Gly Cys Ala Thr Thr
            485                 490                 495

Gly Cys Gly Gly Thr Gly Thr Thr Thr Cys Thr Ala Cys Cys Gly Ala
            500                 505                 510

Thr Cys Cys Gly Cys Ala Gly Cys Cys Gly Cys Thr Gly Ala Ala Ala
        515                 520                 525

Gly Ala Ala Cys Ala Gly Cys Cys Gly Gly Cys Gly Cys Thr Gly Ala
        530                 535                 540

Ala Thr Gly Ala Thr Ala Gly Cys Cys Gly Thr Thr Ala Thr Gly Cys
545                 550                 555                 560

Gly Cys Thr Gly Thr Cys Thr Ala Gly Cys Gly Thr Cys Thr Gly
                565                 570                 575

Cys Gly Thr Gly Thr Thr Ala Gly Cys Gly Cys Gly Ala Cys Cys Thr
            580                 585                 590

Thr Thr Thr Gly Gly Cys Ala Ala Ala Thr Cys Cys Gly Cys Gly
            595                 600                 605

Thr Ala Ala Cys Cys Ala Thr Thr Thr Cys Gly Thr Thr Gly Cys
    610                 615                 620

Cys Ala Gly Gly Thr Gly Cys Ala Gly Thr Thr Thr Ala Thr Gly
625                 630                 635                 640

Gly Cys Cys Thr Gly Ala Gly Cys Gly Ala Ala Ala Cys Gly Ala
                645                 650                 655

Thr Gly Ala Ala Thr Gly Gly Ala Cys Cys Ala Gly Gly Ala Thr
            660                 665                 670

Cys Gly Thr Gly Cys Gly Ala Ala Gly Cys Cys Gly Gly Thr Thr Ala
            675                 680                 685

Cys Cys Cys Ala Gly Ala Thr Thr Gly Thr Thr Ala Gly Cys Gly Cys
    690                 695                 700

Gly Gly Ala Ala Gly Cys Cys Thr Gly Gly Gly Cys Cys Gly Cys
705                 710                 715                 720

Gly Cys Ala Gly Ala Thr Thr Ala Ala
                725

<210> SEQ ID NO 8
<211> LENGTH: 242
<212> TYPE: PRT
<213> ORGANISM: Artificial Sequence
<220> FEATURE:
<223> OTHER INFORMATION: Synthetic Polypeptide

<400> SEQUENCE: 8

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Asn
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
            100                 105                 110

Glu Asp Leu Lys Asn Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Tyr Pro Asp His Val Glu Leu Ser Trp Trp Val Asn
145                 150                 155                 160

Gly Lys Glu Val His Cys Gly Val Ser Thr Asp Pro Gln Pro Leu Lys
                165                 170                 175

Glu Gln Pro Ala Leu Asn Asp Ser Arg Tyr Ala Leu Ser Ser Arg Leu
            180                 185                 190

Arg Val Ser Ala Thr Phe Trp Gln Asn Pro Arg Asn His Phe Arg Cys
195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Asp

<210> SEQ ID NO 9
<211> LENGTH: 615
<212> TYPE: DNA
<213> ORGANISM: Artificial Sequence
<220> FEATURE:
<223> OTHER INFORMATION: Synthetic Polyribonucleotide

<400> SEQUENCE: 9

```
atgggccaac tgctggaaca atccccgcaa ttcctgagta ttcaagaagg cgaaaatctg      60
acggtctact gtaattcatc atcggtcttt agctctctgc agtggtatcg tcaagaaccg     120
ggtgaaggtc cggtcctgct ggtgaccgtg gttacgggcg gtgaagtgaa aaagctgaaa     180
cgtctgacct tcagttcgg cgatgcgcgc aaggacagtt ccctgcatat taccgcagca     240
cagccgggtg atacgggtct gtacctgtgc gcaggcgctg gtagccaagg taacctgatt     300
tttggcaagg gtacgaagct gagcgttaaa ccgaacatcc agaatccgga tccggccgtt     360
tatcagctgc gtgatagcaa aagcagcgat aaaagcgtgt gcctgttcac cgattttgat     420
agccagacca acgtgagcca gagcaaagat agcgatgtgt acatcaccga taaaaccgtg     480
ctggatatgt gcagcatgga tttcaaaagc aatagcgcgg ttgcgtggag caacaaaagc     540
gattttgcgt gcgcgaacgc gtttaacaac agcatcatcc cggaagatac gttcttcccc     600
agcccagaaa gttcc                                                     615
```

<210> SEQ ID NO 10
<211> LENGTH: 205
<212> TYPE: PRT
<213> ORGANISM: Artificial Sequence
<220> FEATURE:
<223> OTHER INFORMATION: Synthetic Polypeptide

<400> SEQUENCE: 10

Met Gly Gln Leu Leu Glu Gln Ser Pro Gln Phe Leu Ser Ile Gln Glu
1               5                   10                  15

Gly Glu Asn Leu Thr Val Tyr Cys Asn Ser Ser Ser Val Phe Ser Ser
            20                  25                  30

Leu Gln Trp Tyr Arg Gln Glu Pro Gly Glu Gly Pro Val Leu Leu Val
        35                  40                  45

Thr Val Val Thr Gly Gly Glu Val Lys Lys Leu Lys Arg Leu Thr Phe
    50                  55                  60

Gln Phe Gly Asp Ala Arg Lys Asp Ser Ser Leu His Ile Thr Ala Ala
65                  70                  75                  80

Gln Pro Gly Asp Thr Gly Leu Tyr Leu Cys Ala Gly Ala Gly Ser Gln
                85                  90                  95

Gly Asn Leu Ile Phe Gly Lys Gly Thr Lys Leu Ser Val Lys Pro Asn
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Asn
    130                 135                 140

```
Val Ser Gln Ser Lys Asp Ser Asp Val Tyr Ile Thr Asp Lys Thr Val
145                 150                 155                 160

Leu Asp Met Cys Ser Met Asp Phe Lys Ser Asn Ser Ala Val Ala Trp
            165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
            195                 200                 205
```

<210> SEQ ID NO 11
<211> LENGTH: 735
<212> TYPE: DNA
<213> ORGANISM: Artificial Sequence
<220> FEATURE:
<223> OTHER INFORMATION: Synthetic Polyribonucleotide

<400> SEQUENCE: 11

```
atggtggacg gcggcattac ccaaagcccg aagtacctgt ttcgcaagga aggccaaaat    60
gtgaccctgt cgtgtgaaca aaatctgaac catgatgcga tgtattggta ccgtcaggac   120
ccgggtcaag gtctgcgtct gatttattac agccagatcg tgaatgattt tcaaaaaggc   180
gacattgcag aaggttatag cgtgagccgt gaaaagaaag aatcttttcc gctgaccgtc   240
acgtccgctc agaagaaccc gaccgcgttc tacctgtgcg cgagcagcag ccgtagcagc   300
tatgaacaat actttggtcc gggtacgcgt ctgaccgtca cggaagatct gaaaaacgtg   360
tttccgccgg aagttgcggt ttttgaaccg agcgaagcgg aaattagcca tacccagaaa   420
gcgaccctgg tttgtctggc gaccggtttt tatccggatc atgtggaact gtcttggtgg   480
gtgaacggca agaagtgca ttgcggtgtt tctaccgatc cgcagccgct gaaagaacag   540
ccggcgctga tgatagccg ttatgcgctg tctagccgtc tgcgtgttag cgcgaccttt   600
tggcaaaatc cgcgtaacca tttcgttgc caggtgcagt tttatggcct gagcgaaaac   660
gatgaatgga cccaggatcg tgcgaagccg gttacccaga ttgttagcgc ggaagcctgg   720
ggccgcgcag attaa                                                   735
```

<210> SEQ ID NO 12
<211> LENGTH: 244
<212> TYPE: PRT
<213> ORGANISM: Artificial Sequence
<220> FEATURE:
<223> OTHER INFORMATION: Synthetic Polypeptide

<400> SEQUENCE: 12

```
Met Val Asp Gly Gly Ile Thr Gln Ser Pro Lys Tyr Leu Phe Arg Lys
1               5                   10                  15

Glu Gly Gln Asn Val Thr Leu Ser Cys Glu Gln Asn Leu Asn His Asp
            20                  25                  30

Ala Met Tyr Trp Tyr Arg Gln Asp Pro Gly Gln Gly Leu Arg Leu Ile
        35                  40                  45

Tyr Tyr Ser Gln Ile Val Asn Asp Phe Gln Lys Gly Asp Ile Ala Glu
    50                  55                  60

Gly Tyr Ser Val Ser Arg Glu Lys Lys Glu Ser Phe Pro Leu Thr Val
65                  70                  75                  80

Thr Ser Ala Gln Lys Asn Pro Thr Ala Phe Tyr Leu Cys Ala Ser Ser
                85                  90                  95

Ser Arg Ser Ser Tyr Glu Gln Tyr Phe Gly Pro Gly Thr Arg Leu Thr
            100                 105                 110
```

```
Val Thr Glu Asp Leu Lys Asn Val Phe Pro Pro Glu Val Ala Val Phe
            115                 120                 125

Glu Pro Ser Glu Ala Glu Ile Ser His Thr Gln Lys Ala Thr Leu Val
        130                 135                 140

Cys Leu Ala Thr Gly Phe Tyr Pro Asp His Val Glu Leu Ser Trp Trp
145                 150                 155                 160

Val Asn Gly Lys Glu Val His Cys Gly Val Ser Thr Asp Pro Gln Pro
                165                 170                 175

Leu Lys Glu Gln Pro Ala Leu Asn Asp Ser Arg Tyr Ala Leu Ser Ser
            180                 185                 190

Arg Leu Arg Val Ser Ala Thr Phe Trp Gln Asn Pro Arg Asn His Phe
        195                 200                 205

Arg Cys Gln Val Gln Phe Tyr Gly Leu Ser Glu Asn Asp Glu Trp Thr
    210                 215                 220

Gln Asp Arg Ala Lys Pro Val Thr Gln Ile Val Ser Ala Glu Ala Trp
225                 230                 235                 240

Gly Arg Ala Asp

<210> SEQ ID NO 13
<211> LENGTH: 630
<212> TYPE: DNA
<213> ORGANISM: Artificial Sequence
<220> FEATURE:
<223> OTHER INFORMATION: Synthetic Polyribonucleotide

<400> SEQUENCE: 13
atgggtaagc aggaagtgac ccagatccct gccgccctga gcgtgcccga gggcgagaac      60
ctggtgctga actgcagctt caccgacagc gccatctaca acctgcagtg gttccggcag     120
gaccccggca agggcctgac cagcctgctg ctggtgcgtc cgtatcagcg ggagcagacc     180
agcggcagac tgaacgccag cctggacaag agcagcggca agcaccctgt atatcgcc      240 gccagccagc ccgcgactc cgccacctac ctgtgcgctg tgcggcctgg cggagccggc     300
agctaccagc tgaccttcgg caagggcacc aagctgtccg tgatccccaa tatccagaat     360
ccggatccgg ccgtttatca gctgcgtgat agcaaaagca gcgataaaag cgtgtgcctg     420
ttcaccgatt ttgatagcca gaccaacgtg agccagagca agatagcga tgtgtacatc     480 accgataaaa ccgtgctgga tatgtgcagc atggatttca aaagcaatag cgcggttgcg     540
tggagcaaca aaagcgattt tgcgtgcgcg aacgcgttta caacagcat catcccggaa     600 gatacgttct tccccagccc agaaagttcc                                      630

<210> SEQ ID NO 14
<211> LENGTH: 210
<212> TYPE: PRT
<213> ORGANISM: Artificial Sequence
<220> FEATURE:
<223> OTHER INFORMATION: Synthetic Polypeptide

<400> SEQUENCE: 14

Met Gly Lys Gln Glu Val Thr Gln Ile Pro Ala Ala Leu Ser Val Pro
1               5                   10                  15

Glu Gly Glu Asn Leu Val Leu Asn Cys Ser Phe Thr Asp Ser Ala Ile
            20                  25                  30

Tyr Asn Leu Gln Trp Phe Arg Gln Asp Pro Gly Lys Gly Leu Thr Ser
        35                  40                  45

Leu Leu Leu Val Arg Pro Tyr Gln Arg Glu Gln Thr Ser Gly Arg Leu
    50                  55                  60
```

Asn Ala Ser Leu Asp Lys Ser Ser Gly Arg Ser Thr Leu Tyr Ile Ala
 65                  70                  75                  80

Ala Ser Gln Pro Gly Asp Ser Ala Thr Tyr Leu Cys Ala Val Arg Pro
                 85                  90                  95

Gly Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Cys Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser
    210

<210> SEQ ID NO 15
<211> LENGTH: 735
<212> TYPE: DNA
<213> ORGANISM: Artificial Sequence
<220> FEATURE:
<223> OTHER INFORMATION: Synthetic Polyribonucleotide

<400> SEQUENCE: 15

| | | | | | |
|---|---|---|---|---|---|
| atgggtaaag | ctggagttac | tcaaactcca | agatatctga | tcaaaacgag | aggacagcaa | 60 |
| gtgacactga | gctgctcccc | tatctctggg | cataggagtg | tatcctggta | ccaacagacc | 120 |
| ccaggacagg | gccttcagtt | cctctttgaa | tacttcagtg | agacacagag | aaacaaagga | 180 |
| aacttccctg | gtcgattctc | agggcgccag | ttctctaact | ctcgctctga | gatgaatgtg | 240 |
| agcaccttgg | agctggggga | ctcggccctt | tatctttgcg | ccagcagccc | gaacatggcc | 300 |
| gacgagcagt | acttcgggcc | gggcaccagg | ctcacggtca | cagaagatct | gaaaaacgtg | 360 |
| tttccgccgg | aagttgcggt | ttttgaaccg | agcgaagcgg | aaattagcca | tacccagaaa | 420 |
| gcgaccctgg | tttgtctggc | gaccggtttt | tatccggatc | atgtggaact | gtcttggtgg | 480 |
| gtgaacggca | agaagtgcca | ttgcggtgtt | tctaccgatc | cgcagccgct | gaaagaacag | 540 |
| ccggcgctga | atgatagccg | ttatgcgctg | tctagccgtc | tgcgtgttag | cgcgaccttt | 600 |
| tggcaaaatc | cgcgtaacca | ttttcgttgc | caggtgcagt | tttatggcct | gagcgaaaac | 660 |
| gatgaatgga | cccaggatcg | tgcgaagccg | gttacccaga | ttgttagcgc | ggaagcctgg | 720 |
| ggccgcgcag | attaa | | | | | 735 |

<210> SEQ ID NO 16
<211> LENGTH: 244
<212> TYPE: PRT
<213> ORGANISM: Artificial Sequence
<220> FEATURE:
<223> OTHER INFORMATION: Synthetic Polypeptide

<400> SEQUENCE: 16

| | | | | | | | | | | | | | | | |
|---|---|---|---|---|---|---|---|---|---|---|---|---|---|---|---|
|Met|Gly|Lys|Ala|Gly|Val|Thr|Gln|Thr|Pro|Arg|Tyr|Leu|Ile|Lys|Thr|
|1| | | |5| | | | |10| | | | |15| |

Arg Gly Gln Gln Val Thr Leu Ser Cys Ser Pro Ile Ser Gly His Arg
                20                  25                  30

Ser Val Ser Trp Tyr Gln Gln Thr Pro Gly Gln Gly Leu Gln Phe Leu
         35                  40                  45

Phe Glu Tyr Phe Ser Glu Thr Gln Arg Asn Lys Gly Asn Phe Pro Gly
 50                  55                  60

Arg Phe Ser Gly Arg Gln Phe Ser Asn Ser Arg Ser Glu Met Asn Val
 65                  70                  75                  80

Ser Thr Leu Glu Leu Gly Asp Ser Ala Leu Tyr Leu Cys Ala Ser Ser
                 85                  90                  95

Pro Asn Met Ala Asp Glu Gln Tyr Phe Gly Pro Gly Thr Arg Leu Thr
              100                 105                 110

Val Thr Glu Asp Leu Lys Asn Val Phe Pro Pro Glu Val Ala Val Phe
         115                 120                 125

Glu Pro Ser Glu Ala Glu Ile Ser His Thr Gln Lys Ala Thr Leu Val
 130                 135                 140

Cys Leu Ala Thr Gly Phe Tyr Pro Asp His Val Glu Leu Ser Trp Trp
145                 150                 155                 160

Val Asn Gly Lys Glu Val His Cys Gly Val Ser Thr Asp Pro Gln Pro
                165                 170                 175

Leu Lys Glu Gln Pro Ala Leu Asn Asp Ser Arg Tyr Ala Leu Ser Ser
            180                 185                 190

Arg Leu Arg Val Ser Ala Thr Phe Trp Gln Asn Pro Arg Asn His Phe
        195                 200                 205

Arg Cys Gln Val Gln Phe Tyr Gly Leu Ser Glu Asn Asp Glu Trp Thr
210                 215                 220

Gln Asp Arg Ala Lys Pro Val Thr Gln Ile Val Ser Ala Glu Ala Trp
225                 230                 235                 240

Gly Arg Ala Asp

<210> SEQ ID NO 17
<211> LENGTH: 621
<212> TYPE: DNA
<213> ORGANISM: Artificial Sequence
<220> FEATURE:
<223> OTHER INFORMATION: Synthetic Polyribonucleotide

<400> SEQUENCE: 17

```
atgggcaaaa ccacccagcc gaactcaatg gaaagcaacg aagaagaacc ggtccacctg      60
ccgtgtaatc acagcaccat ctcaggcacc gattatattc attggtaccg tcagctgccg     120
agccaaggtc cggaatatgt gatccacggt ctgaccagta cgttaacaa tcgtatggca      180
tccctggcaa ttgctgaaga tcgcaaaagc tctaccctga tcctgcatcg tgcaacgctg     240
cgtgacgcag ccgtttatta ctgcattctg ccgctggccg gcgtaccag ctacggcaag      300
ctgacgtttg gccagggtac cattctgacg gtccacccga atatccagaa tccggatccg     360
gccgtttatc agctgcgtga tagcaaaagc agcgataaaa gcgtgtgcct gttcaccgat     420
tttgatagcc agaccaacgt gagccagagc aaagatagcg atgtgtacat caccgataaa     480
accgtgctgg atatgcgcag catggatttc aaaagcaata gcgcggttgc gtggagcaac     540
```

```
aaaagcgatt ttgcgtgcgc gaacgcgttt aacaacagca tcatcccgga agatacgttc    600
ttctgcagcc cagaaagttc c                                              621
```

<210> SEQ ID NO 18
<211> LENGTH: 207
<212> TYPE: PRT
<213> ORGANISM: Artificial Sequence
<220> FEATURE:
<223> OTHER INFORMATION: Synthetic Polypeptide

<400> SEQUENCE: 18

```
Met Gly Lys Thr Thr Gln Pro Asn Ser Met Glu Ser Asn Glu Glu Glu
1               5                   10                  15

Pro Val His Leu Pro Cys Asn His Ser Thr Ile Ser Gly Thr Asp Tyr
            20                  25                  30

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ala Thr Leu
65                  70                  75                  80

Arg Asp Ala Ala Val Tyr Tyr Cys Ile Leu Pro Leu Ala Gly Gly Thr
                85                  90                  95

Ser Tyr Gly Lys Leu Thr Phe Gly Gln Gly Thr Ile Leu Thr Val His
            100                 105                 110

Pro Asn Ile Gln Asn Pro Asp Pro Ala Val Tyr Gln Leu Arg Asp Ser
        115                 120                 125

Lys Ser Ser Asp Lys Ser Val Cys Leu Phe Thr Asp Phe Asp Ser Gln
    130                 135                 140

Thr Asn Val Ser Gln Ser Lys Asp Ser Asp Val Tyr Ile Thr Asp Lys
145                 150                 155                 160

Thr Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
            180                 185                 190

Ser Ile Ile Pro Glu Asp Thr Phe Phe Cys Ser Pro Glu Ser Ser
        195                 200                 205
```

<210> SEQ ID NO 19
<211> LENGTH: 729
<212> TYPE: DNA
<213> ORGANISM: Artificial Sequence
<220> FEATURE:
<223> OTHER INFORMATION: Synthetic Polyribonucleotide

<400> SEQUENCE: 19

```
atgggcgtgt cccaaagccc gcgttacaaa gttgccaagc gtggtcaaga tgttgctctg    60
cgttgcgatc cgattagtgg tcatgttagc ctgttttggt atcagcaagc gctgggccag   120
ggtccggaat tctgacccta cttccagaac gaagcacaac tggataaatc aggcctgccg   180
tcggaccgtt tctttgctga cgcccggaa ggtagtgttt ccaccctgaa gattcagcgt    240
acgcagcaag aagattctgc ggtctatctg tgcgccagct ctctgggcca ggcgtatgaa   300
caatactttg gtccgggtac gcgtctgacc gtcacggaag atctgaaaaa cgtgtttccg   360
ccggaagttg cggttttga accgagcgaa tgcgaaatta gccataccca gaaagcgacc   420
ctggtttgtc tggcgaccgg tttttatccg gatcatgtgg aactgtcttg gtgggtgaac   480
```

```
ggcaaagaag tgcatagcgg tgtttctacc gatccgcagc cgctgaaaga acagccggcg    540
ctgaatgata gccgttatgc gctgtctagc cgtctgcgtg ttagcgcgac cttttggcaa    600
aatccgcgta accattttcg ttgccaggta cagttttatg gcctgagcga aaacgatgaa    660
tggacccagg atcgtgcgaa gccggttacc cagattgtta gcgcggaagc ctggggccgc    720
gcagattaa                                                            729
```

<210> SEQ ID NO 20
<211> LENGTH: 242
<212> TYPE: PRT
<213> ORGANISM: Artificial Sequence
<220> FEATURE:
<223> OTHER INFORMATION: Synthetic Polypeptide

<400> SEQUENCE: 20

```
Met Gly Val Ser Gln Ser Pro Arg Tyr Lys Val Ala Lys Arg Gly Gln
1               5                   10                  15

Asp Val Ala Leu Arg Cys Asp Pro Ile Ser Gly His Val Ser Leu Phe
            20                  25                  30

Trp Tyr Gln Gln Ala Leu Gly Gln Gly Pro Glu Phe Leu Thr Tyr Phe
        35                  40                  45

Gln Asn Glu Ala Gln Leu Asp Lys Ser Gly Leu Pro Ser Asp Arg Phe
    50                  55                  60

Phe Ala Glu Arg Pro Glu Gly Ser Val Ser Thr Leu Lys Ile Gln Arg
65                  70                  75                  80

Thr Gln Gln Glu Asp Ser Ala Val Tyr Leu Cys Ala Ser Ser Leu Gly
                85                  90                  95

Gln Ala Tyr Glu Gln Tyr Phe Gly Pro Gly Thr Arg Leu Thr Val Thr
            100                 105                 110

Glu Asp Leu Lys Asn Val Phe Pro Pro Glu Val Ala Val Phe Glu Pro
        115                 120                 125

Ser Glu Cys Glu Ile Ser His Thr Gln Lys Ala Thr Leu Val Cys Leu
    130                 135                 140

Ala Thr Gly Phe Tyr Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175

Glu Gln Pro Ala Leu Asn Asp Ser Arg Tyr Ala Leu Ser Ser Arg Leu
            180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Asp
```

<210> SEQ ID NO 21
<211> LENGTH: 627
<212> TYPE: DNA
<213> ORGANISM: Artificial Sequence
<220> FEATURE:
<223> OTHER INFORMATION: Synthetic Polyribonucleotide

<400> SEQUENCE: 21

```
atggcacaag aagttactca aattccggcg gcgctgagcg ttccggaagg tgaaaacctg     60
gtgctgaact gcagctttac cgatagcgcg atctataacc tgcagtggtt tcgtcaagat    120
ccgggtaaag gtctgaccag cctgctgctg attcagagca gccagcgtga acagaccagc    180
ggtcgtctga atgcgagcct ggataaaagc agcggtcgta gcaccctgta tattgcggcg    240
agccagccgg gtgatagcgc aacctatctg tgtgcggttc gtccgaccag cggtggtagc    300
tatattccga cctttggtcg tggcaccagc ctgattgtgc atccgtatat ccagaatccg    360
gatccggccg tttatcagct gcgtgatagc aaaagcagcg ataaaagcgt gtgcctgttc    420
accgattttg atagccagac caacgtgagc cagagcaaag atagcgatgt gtacatcacc    480
gataaaaccg tgctggatat gcgcagcatg gatttcaaaa gcaatagcgc ggttgcgtgg    540
agcaacaaaa gcgattttgc gtgcgcgaac gcgtttaaca acagcatcat cccggaagat    600
acgttcttct gcagcccaga aagttcc                                        627
```

<210> SEQ ID NO 22
<211> LENGTH: 209
<212> TYPE: PRT
<213> ORGANISM: Artificial Sequence
<220> FEATURE:
<223> OTHER INFORMATION: Synthetic Polypeptide

<400> SEQUENCE: 22

```
Met Ala Gln Glu Val Thr Gln Ile Pro Ala Ala Leu Ser Val Pro Glu
1               5                   10                  15
Gly Glu Asn Leu Val Leu Asn Cys Ser Phe Thr Asp Ser Ala Ile Tyr
                20                  25                  30
Asn Leu Gln Trp Phe Arg Gln Asp Pro Gly Lys Gly Leu Thr Ser Leu
            35                  40                  45
Leu Leu Ile Gln Ser Ser Gln Arg Glu Gln Thr Ser Gly Arg Leu Asn
        50                  55                  60
Ala Ser Leu Asp Lys Ser Ser Gly Arg Ser Thr Leu Tyr Ile Ala Ala
65                  70                  75                  80
Ser Gln Pro Gly Asp Ser Ala Thr Tyr Leu Cys Ala Val Arg Pro Thr
                85                  90                  95
Ser Gly Gly Ser Tyr Ile Pro Thr Phe Gly Arg Gly Thr Ser Leu Ile
                100                 105                 110
Val His Pro Tyr Ile Gln Asn Pro Asp Pro Ala Val Tyr Gln Leu Arg
            115                 120                 125
Asp Ser Lys Ser Ser Asp Lys Ser Val Cys Leu Phe Thr Asp Phe Asp
        130                 135                 140
Ser Gln Thr Asn Val Ser Gln Ser Lys Asp Ser Asp Val Tyr Ile Thr
145                 150                 155                 160
Asp Lys Thr Val Leu Asp Met Arg Ser Met Asp Phe Lys Ser Asn Ser
                165                 170                 175
Ala Val Ala Trp Ser Asn Lys Ser Asp Phe Ala Cys Ala Asn Ala Phe
                180                 185                 190
Asn Asn Ser Ile Ile Pro Glu Asp Thr Phe Phe Cys Ser Pro Glu Ser
            195                 200                 205
Ser
```

<210> SEQ ID NO 23
<211> LENGTH: 729
<212> TYPE: DNA
<213> ORGANISM: Artificial Sequence
<220> FEATURE:
<223> OTHER INFORMATION: Synthetic Polyribonucleotide

<400> SEQUENCE: 23

```
atgggcgtca cacaaacccc gaaatttcag gtgctgaaaa cgggtcagag catgaccctg      60
cagtgtgcgc aggatatgaa ccacgaatac atgagctggt atcgtcaaga tccgggtatg     120
ggtctgcgtc tgatccatta tagcgtgggt gcgggcatta ccgatcaggg tgaagtgccg     180
aacggttata tgttagccg tagcaccacc gaagattttc cgctgcgtct gctgagcgcg      240
gcgccgagcc agaccagcgt ttattttgc gcgagcagct atgttggtaa caccggcgaa      300
ctgttttttg gtgaaggcag ccgtctgacc gttctggaag atctgaaaaa cgtgtttccg     360
ccggaagttg cggttttga accgagcgaa tgcgaaatta gccataccca gaaagcgacc      420
ctggtttgtc tggcgaccgg tttttatccg gatcatgtgg aactgtcttg gtgggtgaac     480
ggcaaagaag tgcatagcgg tgtttctacc gatccgcagc cgctgaaaga cagccggcg      540
ctgaatgata gccgttatgc gctgtctagc cgtctgcgtg ttagcgcgac cttttggcaa     600
aatccgcgta accattttcg ttgccaggtg cagttttatg gcctgagcga aaacgatgaa     660
tggacccagg atcgtgcgaa gccggttacc cagattgtta gcgcggaagc ctggggccgc     720
gcagattaa                                                             729
```

<210> SEQ ID NO 24
<211> LENGTH: 242
<212> TYPE: PRT
<213> ORGANISM: Artificial Sequence
<220> FEATURE:
<223> OTHER INFORMATION: Synthetic Polypeptide

<400> SEQUENCE: 24

```
Met Gly Val Thr Gln Thr Pro Lys Phe Gln Val Leu Lys Thr Gly Gln
1               5                  10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Asn
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
            100                 105                 110

Glu Asp Leu Lys Asn Val Phe Pro Pro Glu Val Ala Val Phe Glu Pro
        115                 120                 125

Ser Glu Cys Glu Ile Ser His Thr Gln Lys Ala Thr Leu Val Cys Leu
    130                 135                 140

Ala Thr Gly Phe Tyr Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175
```

Glu Gln Pro Ala Leu Asn Asp Ser Arg Tyr Ala Leu Ser Ser Arg Leu
            180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Glu Ala Trp Gly Arg
225                 230                 235                 240

Ala Asp

<210> SEQ ID NO 25
<211> LENGTH: 615
<212> TYPE: DNA
<213> ORGANISM: Artificial Sequence
<220> FEATURE:
<223> OTHER INFORMATION: Synthetic Polyribonucleotide

<400> SEQUENCE: 25
atgggccaac tgctggaaca atccccgcaa ttcctgagta ttcaagaagg cgaaaatctg      60
acggtctact gtaattcatc atcggtcttt agctctctgc agtggtatcg tcaagaaccg     120
ggtgaaggtc cggtcctgct ggtgaccgtg gttacgggcg gtgaagtgaa aaagctgaaa     180
cgtctgacct ttcagttcgg cgatgcgcgc aaggacagtt ccctgcatat taccgcagca     240
cagccgggtg atacgggtct gtacctgtgc gcaggcgctg gtagccaagg taacctgatt     300
tttggcaagg gtacgaagct gagcgttaaa ccgaacatcc agaatccgga tccggccgtt     360
tatcagctgc gtgatagcaa aagcagcgat aaaagcgtgt gcctgttcac cgattttgat     420
agccagacca acgtgagcca gagcaaagat agcgatgtgt acatcaccga taaaaccgtg     480
ctggatatgc gcagcatgga tttcaaaagc aatagcgcgg ttgcgtggag caacaaaagc     540
gattttgcgt gcgcgaacgc gtttaacaac agcatcatcc cggaagatac gttcttctgc     600
agcccagaaa gttcc                                                     615

<210> SEQ ID NO 26
<211> LENGTH: 205
<212> TYPE: PRT
<213> ORGANISM: Artificial Sequence
<220> FEATURE:
<223> OTHER INFORMATION: Synthetic Polypeptide

<400> SEQUENCE: 26

Met Gly Gln Leu Leu Glu Gln Ser Pro Gln Phe Leu Ser Ile Gln Glu
1               5                   10                  15

Gly Glu Asn Leu Thr Val Tyr Cys Asn Ser Ser Ser Val Phe Ser Ser
            20                  25                  30

Leu Gln Trp Tyr Arg Gln Glu Pro Gly Glu Gly Pro Val Leu Leu Val
        35                  40                  45

Thr Val Val Thr Gly Gly Glu Val Lys Lys Leu Lys Arg Leu Thr Phe
    50                  55                  60

Gln Phe Gly Asp Ala Arg Lys Asp Ser Ser Leu His Ile Thr Ala Ala
65                  70                  75                  80

Gln Pro Gly Asp Thr Gly Leu Tyr Leu Cys Ala Gly Ala Gly Ser Gln
            85                  90                  95

Gly Asn Leu Ile Phe Gly Lys Gly Thr Lys Leu Ser Val Lys Pro Asn
            100                 105                 110

Ile Gln Asn Pro Asp Pro Ala Val Tyr Gln Leu Arg Asp Ser Lys Ser
        115                 120                 125

```
Ser Asp Lys Ser Val Cys Leu Phe Thr Asp Phe Asp Ser Gln Thr Asn
    130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
                180                 185                 190

Ile Pro Glu Asp Thr Phe Phe Cys Ser Pro Glu Ser Ser
                195                 200                 205

<210> SEQ ID NO 27
<211> LENGTH: 735
<212> TYPE: DNA
<213> ORGANISM: Artificial Sequence
<220> FEATURE:
<223> OTHER INFORMATION: Synthetic Polyribonucleotide

<400> SEQUENCE: 27
atggtggacg gcggcattac ccaaagcccg aagtacctgt tcgcaagga aggccaaaat     60 gtgaccctgt cgtgtgaaca aaatctgaac catgatgcga tgtattggta ccgtcaggac    120
ccgggtcaag gtctgcgtct gatttattac agccagatcg tgaatgattt tcaaaaaggc    180
gacattgcag aaggttatag cgtgagccgt gaaaagaaag aatcttttcc gctgaccgtc    240
acgtccgctc agaagaaccc gaccgcgttc tacctgtgcg cgagcagcag ccgtagcagc    300
tatgaacaat actttggtcc gggtacgcgt ctgaccgtca cggaagatct gaaaaacgtg    360
tttccgccgg aagttgcggt ttttgaaccg agcgaatgcg aaattagcca tacccagaaa    420
gcgaccctgg tttgtctggc gaccggtttt tatccggatc atgtggaact gtcttggtgg    480
gtgaacggca agaagtgca tagcggtgtt tctaccgatc cgcagccgct gaaagaacag    540
ccggcgctga atgatagccg ttatgcgctg tctagccgtc tgcgtgttag cgcgaccttt    600
tggcaaaatc cgcgtaacca ttttcgttgc caggtgcagt ttatggcct gagcgaaaac    660 gatgaatgga cccaggatcg tgcgaagccg gttacccaga ttgttagcgc ggaagcctgg    720
ggccgcgcag attaa                                                    735

<210> SEQ ID NO 28
<211> LENGTH: 244
<212> TYPE: PRT
<213> ORGANISM: Artificial Sequence
<220> FEATURE:
<223> OTHER INFORMATION: Synthetic Polypeptide

<400> SEQUENCE: 28

Met Val Asp Gly Gly Ile Thr Gln Ser Pro Lys Tyr Leu Phe Arg Lys
1               5                   10                  15

Glu Gly Gln Asn Val Thr Leu Ser Cys Glu Gln Asn Leu Asn His Asp
                20                  25                  30

Ala Met Tyr Trp Tyr Arg Gln Asp Pro Gly Gln Gly Leu Arg Leu Ile
            35                  40                  45

Tyr Tyr Ser Gln Ile Val Asn Asp Phe Gln Lys Gly Asp Ile Ala Glu
    50                  55                  60

Gly Tyr Ser Val Ser Arg Glu Lys Lys Glu Ser Phe Pro Leu Thr Val
65                  70                  75                  80

Thr Ser Ala Gln Lys Asn Pro Thr Ala Phe Tyr Leu Cys Ala Ser Ser
                85                  90                  95
```

Ser Arg Ser Ser Tyr Glu Gln Tyr Phe Gly Pro Gly Thr Arg Leu Thr
                100                 105                 110

Val Thr Glu Asp Leu Lys Asn Val Phe Pro Pro Glu Val Ala Val Phe
            115                 120                 125

Glu Pro Ser Glu Cys Glu Ile Ser His Thr Gln Lys Ala Thr Leu Val
        130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val Ser Thr Asp Pro Gln Pro
                165                 170                 175

Leu Lys Glu Gln Pro Ala Leu Asn Asp Ser Arg Tyr Ala Leu Ser Ser
            180                 185                 190

Arg Leu Arg Val Ser Ala Thr Phe Trp Gln Asn Pro Arg Asn His Phe
        195                 200                 205

Arg Cys Gln Val Gln Phe Tyr Gly Leu Ser Glu Asn Asp Glu Trp Thr
210                 215                 220

Gln Asp Arg Ala Lys Pro Val Thr Gln Ile Val Ser Ala Glu Ala Trp
225                 230                 235                 240

Gly Arg Ala Asp

<210> SEQ ID NO 29
<211> LENGTH: 630
<212> TYPE: DNA
<213> ORGANISM: Artificial Sequence
<220> FEATURE:
<223> OTHER INFORMATION: Synthetic Polyribonucleotide

<400> SEQUENCE: 29
atgggtaagc aggaagtgac ccagatccct gccgccctga gcgtgcccga gggcgagaac      60
ctggtgctga actgcagctt caccgacagc gccatctaca acctgcagtg gttccggcag     120
gaccccggca agggcctgac cagcctgctg ctggtgcgtc cgtatcagcg ggagcagacc     180
agcggcagac tgaacgccag cctggacaag agcagcggca agcacccct gtatatcgcc     240
gccagccagc ccggcgactc cgccacctac ctgtgcgctg tcggcctgg cggagcggc      300
agctaccagc tgaccttcgg caagggcacc aagctgtccg tgatccccaa tatccagaat     360
ccggatccgg ccgtttatca gctgcgtgat agcaaaagca gcgataaaag cgtgtgcctg     420
ttcaccgatt tgatagcca gaccaacgtg agccagagca agatagcga tgtgtacatc     480
accgataaaa ccgtgctgga tatgcgcagc atggatttca aaagcaatag cgcggttgcg     540
tggagcaaca aaagcgattt tgcgtgcgcg aacgcgttta caacagcat catcccggaa     600
gatacgttct tctgcagccc agaaagttcc                                     630

<210> SEQ ID NO 30
<211> LENGTH: 210
<212> TYPE: PRT
<213> ORGANISM: Artificial Sequence
<220> FEATURE:
<223> OTHER INFORMATION: Synthetic Polypeptide

<400> SEQUENCE: 30

Met Gly Lys Gln Glu Val Thr Gln Ile Pro Ala Ala Leu Ser Val Pro
1               5                   10                  15

Glu Gly Glu Asn Leu Val Leu Asn Cys Ser Phe Thr Asp Ser Ala Ile
            20                  25                  30

Tyr Asn Leu Gln Trp Phe Arg Gln Asp Pro Gly Lys Gly Leu Thr Ser
        35                  40                  45

Leu Leu Leu Val Arg Pro Tyr Gln Arg Glu Gln Thr Ser Gly Arg Leu
 50                  55                  60

Asn Ala Ser Leu Asp Lys Ser Ser Gly Arg Ser Thr Leu Tyr Ile Ala
 65                  70                  75                  80

Ala Ser Gln Pro Gly Asp Ser Ala Thr Tyr Leu Cys Ala Val Arg Pro
                 85                  90                  95

Gly Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Cys Ser Pro Glu
        195                 200                 205

Ser Ser
    210

<210> SEQ ID NO 31
<211> LENGTH: 735
<212> TYPE: DNA
<213> ORGANISM: Artificial Sequence
<220> FEATURE:
<223> OTHER INFORMATION: Synthetic Polyribonucleotide

<400> SEQUENCE: 31
atgggtaaag ctggagttac tcaaactcca agatatctga tcaaaacgag aggacagcaa      60
gtgacactga gctgctcccc tatctctggg cataggagtg tatcctggta ccaacagacc     120
ccaggacagg gccttcagtt cctctttgaa tacttcagtg agacacagag aaacaaagga     180
aacttccctg gtcgattctc agggcgccag ttctctaact ctcgctctga gatgaatgtg     240
agcaccttgg agctggggga ctcggccctt tatctttgcg ccagcagccc gaacatggcc     300
gacgagcagt acttcgggcc gggcaccagg ctcacggtca cagaagatct gaaaaacgtg     360
tttccgccgg aagttgcggt ttttgaaccg agcgaatgcg aaattagcca tacccagaaa     420
gcgaccctgg tttgtctggc gaccggtttt atccggatc atgtggaact gtcttggtgg     480
gtgaacggca agaagtgcag tagcggtgtt tctaccgatc cgcagccgct gaaagaacag     540
ccggcgctga atgatagccg ttatgcgctg tctagccgtc tgcgtgttag cgcgaccttt     600
tggcaaaatc cgcgtaacca ttttcgttgc caggtgcagt tttatggcct gagcgaaaac     660
gatgaatgga cccaggatcg tgcgaagccg gttacccaga ttgttagcgc ggaagcctgg     720
ggccgcgcag attaa                                                      735

<210> SEQ ID NO 32
<211> LENGTH: 244
<212> TYPE: PRT
<213> ORGANISM: Artificial Sequence
<220> FEATURE:
<223> OTHER INFORMATION: Synthetic Polypeptide

<400> SEQUENCE: 32

```
Met Gly Lys Ala Gly Val Thr Gln Thr Pro Arg Tyr Leu Ile Lys Thr
1               5                   10                  15
Arg Gly Gln Gln Val Thr Leu Ser Cys Ser Pro Ile Ser Gly His Arg
            20                  25                  30
Ser Val Ser Trp Tyr Gln Gln Thr Pro Gly Gln Gly Leu Gln Phe Leu
        35                  40                  45
Phe Glu Tyr Phe Ser Glu Thr Gln Arg Asn Lys Gly Asn Phe Pro Gly
    50                  55                  60
Arg Phe Ser Gly Arg Gln Phe Ser Asn Ser Arg Ser Glu Met Asn Val
65                  70                  75                  80
Ser Thr Leu Glu Leu Gly Asp Ser Ala Leu Tyr Leu Cys Ala Ser Ser
                85                  90                  95
Pro Asn Met Ala Asp Glu Gln Tyr Phe Gly Pro Gly Thr Arg Leu Thr
            100                 105                 110
Val Thr Glu Asp Leu Lys Asn Val Phe Pro Pro Glu Val Ala Val Phe
        115                 120                 125
Glu Pro Ser Glu Cys Glu Ile Ser His Thr Gln Lys Ala Thr Leu Val
    130                 135                 140
Cys Leu Ala Thr Gly Phe Tyr Pro Asp His Val Glu Leu Ser Trp Trp
145                 150                 155                 160
Val Asn Gly Lys Glu Val His Ser Gly Val Ser Thr Asp Pro Gln Pro
                165                 170                 175
Leu Lys Glu Gln Pro Ala Leu Asn Asp Ser Arg Tyr Ala Leu Ser Ser
            180                 185                 190
Arg Leu Arg Val Ser Ala Thr Phe Trp Gln Asn Pro Arg Asn His Phe
        195                 200                 205
Arg Cys Gln Val Gln Phe Tyr Gly Leu Ser Glu Asn Asp Glu Trp Thr
    210                 215                 220
Gln Asp Arg Ala Lys Pro Val Thr Gln Ile Val Ser Ala Glu Ala Trp
225                 230                 235                 240
Gly Arg Ala Asp
```

<210> SEQ ID NO 33
<211> LENGTH: 621
<212> TYPE: DNA
<213> ORGANISM: Artificial Sequence
<220> FEATURE:
<223> OTHER INFORMATION: Synthetic Polyribonucleotide

<400> SEQUENCE: 33

```
atgggcaaaa ccacccagcc gaactcaatg gaaagcaacg aagaagaacc ggtccacctg      60
ccgtgtaatc acagcaccat ctcaggcacc gattatattc attggtaccg tcagctgccg     120
agccaaggtc cggaatatgt gatccacggt ctgaccagta cgttaacaa tcgtatggca      180 tccctggcaa ttgctgaaga tcgcaaaagc tctaccctga tcctgcatcg tgcaacgctg     240
cgtgacgcag ccgtttatta ctgcattctg ccgctggccg gcggtaccag ctacggcaag     300
ctgacgtttg gccagggtac cattctgacg gtccacccga acatccagaa tccggatccg     360
gccgtttgcc agctgcgtga tagcaaaagc agcgataaaa gcgtgtgcct gttcaccgat     420
tttgatagcc agaccaacgt gagccagagc aaagatagcg atgtgtacat caccgataaa     480
accgtgctgg atatgcgcag catggatttc aaaagcaata gcgcggttgc gtggagcaac     540
```

```
aaaagcgatt tgcgtgcgc gaacgcgttt aacaacagca tcatcccgga agatacgttc    600
ttccccagcc cagaaagttc c                                             621
```

<210> SEQ ID NO 34
<211> LENGTH: 207
<212> TYPE: PRT
<213> ORGANISM: Artificial Sequence
<220> FEATURE:
<223> OTHER INFORMATION: Synthetic Polypeptide

<400> SEQUENCE: 34

```
Met Gly Lys Thr Thr Gln Pro Asn Ser Met Glu Ser Asn Glu Glu Glu
1               5                   10                  15

Pro Val His Leu Pro Cys Asn His Ser Thr Ile Ser Gly Thr Asp Tyr
            20                  25                  30

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ala Thr Leu
65                  70                  75                  80

Arg Asp Ala Ala Val Tyr Tyr Cys Ile Leu Pro Leu Ala Gly Gly Thr
                85                  90                  95

Ser Tyr Gly Lys Leu Thr Phe Gly Gln Gly Thr Ile Leu Thr Val His
            100                 105                 110

Pro Asn Ile Gln Asn Pro Asp Pro Ala Val Cys Gln Leu Arg Asp Ser
        115                 120                 125

Lys Ser Ser Asp Lys Ser Val Cys Leu Phe Thr Asp Phe Asp Ser Gln
    130                 135                 140

Thr Asn Val Ser Gln Ser Lys Asp Ser Asp Val Tyr Ile Thr Asp Lys
145                 150                 155                 160

Thr Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
            180                 185                 190

Ser Ile Ile Pro Glu Asp Thr Phe Phe Pro Ser Pro Glu Ser Ser
        195                 200                 205
```

<210> SEQ ID NO 35
<211> LENGTH: 729
<212> TYPE: DNA
<213> ORGANISM: Artificial Sequence
<220> FEATURE:
<223> OTHER INFORMATION: Synthetic Polyribonucleotide

<400> SEQUENCE: 35

```
atgggcgtgt cccaaagccc gcgttacaaa gttgccaagc gtggtcaaga tgttgctctg    60
cgttgcgatc cgattagtgg tcatgttagc ctgttttggt atcagcaagc gctgggccag   120
ggtccggaat tctgacccta cttccagaac gaagcacaac tggataaatc aggcctgccg   180
tcggaccgtt tctttgctga cgcccggaa ggtagtgttt ccaccctgaa gattcagcgt    240
acgcagcaag aagattctgc ggtctatctg tgcgccagct ctctgggcca ggcgtatgaa   300
caatactttg gtccgggtac gcgtctgacc gtcacggaag atctgaaaaa cgtgtttccg   360
ccggaagttg cggttttga accgagcgaa gcgtgcatta gccataccca gaaagcgacc   420
ctggtttgtc tggcgaccgg ttttatccg gatcatgtgg aactgtcttg gtgggtgaac   480
```

```
ggcaaagaag tgcatagcgg tgtttctacc gatccgcagc cgctgaaaga acagccggcg    540
ctgaatgata ccgttatgc gctgtctagc cgtctgcgtg ttagcgcgac ctttttggcaa    600 aatccgcgta accattttcg ttgccaggta cagttttatg gcctgagcga aaacgatgaa    660
tggacccagg atcgtgcgaa gccggttacc cagattgtta gcgcggaagc ctggggccgc    720
gcagattaa                                                            729
```

<210> SEQ ID NO 36
<211> LENGTH: 242
<212> TYPE: PRT
<213> ORGANISM: Artificial Sequence
<220> FEATURE:
<223> OTHER INFORMATION: Synthetic Polypeptide

<400> SEQUENCE: 36

```
Met Gly Val Ser Gln Ser Pro Arg Tyr Lys Val Ala Lys Arg Gly Gln
1               5                   10                  15

Asp Val Ala Leu Arg Cys Asp Pro Ile Ser Gly His Val Ser Leu Phe
            20                  25                  30

Trp Tyr Gln Gln Ala Leu Gly Gln Gly Pro Glu Phe Leu Thr Tyr Phe
        35                  40                  45

Gln Asn Glu Ala Gln Leu Asp Lys Ser Gly Leu Pro Ser Asp Arg Phe
    50                  55                  60

Phe Ala Glu Arg Pro Glu Gly Ser Val Ser Thr Leu Lys Ile Gln Arg
65                  70                  75                  80

Thr Gln Gln Glu Asp Ser Ala Val Tyr Leu Cys Ala Ser Ser Leu Gly
                85                  90                  95

Gln Ala Tyr Glu Gln Tyr Phe Gly Pro Gly Thr Arg Leu Thr Val Thr
            100                 105                 110

Glu Asp Leu Lys Asn Val Phe Pro Pro Glu Val Ala Val Phe Glu Pro
        115                 120                 125

Ser Glu Ala Cys Ile Ser His Thr Gln Lys Ala Thr Leu Val Cys Leu
    130                 135                 140

Ala Thr Gly Phe Tyr Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175

Glu Gln Pro Ala Leu Asn Asp Ser Arg Tyr Ala Leu Ser Ser Arg Leu
            180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Asp
```

<210> SEQ ID NO 37
<211> LENGTH: 627
<212> TYPE: DNA
<213> ORGANISM: Artificial Sequence
<220> FEATURE:
<223> OTHER INFORMATION: Synthetic Polyribonucleotide

<400> SEQUENCE: 37

```
atggcacaag aagttactca aattccggcg gcgctgagcg ttccggaagg tgaaaacctg      60
gtgctgaact gcagctttac cgatagcgcg atctataacc tgcagtggtt tcgtcaagat    120
ccgggtaaag gtctgaccag cctgctgctg attcagagca gccagcgtga acagaccagc    180
ggtcgtctga atgcgagcct ggataaaagc agcggtcgta gcaccctgta tattgcggcg    240
agccagccgg gtgatagcgc aacctatctg tgtgcggttc gtccgaccag cggtggtagc    300
tatattccga cctttggtcg tggcaccagc ctgattgtgc atccgtatat ccagaatccg    360
gatccggccg tttgccagct gcgtgatagc aaaagcagcg ataaaagcgt gtgcctgttc    420
accgattttg atagccagac caacgtgagc cagagcaaag atagcgatgt gtacatcacc    480
gataaaaccg tgctggatat gcgcagcatg gatttcaaaa gcaatagcgc ggttgcgtgg    540
agcaacaaaa gcgattttgc gtgcgcgaac gcgtttaaca acagcatcat cccggaagat    600
acgttcttcc ccagcccaga aagttcc                                         627
```

<210> SEQ ID NO 38
<211> LENGTH: 209
<212> TYPE: PRT
<213> ORGANISM: Artificial Sequence
<220> FEATURE:
<223> OTHER INFORMATION: Synthetic Polypeptide

<400> SEQUENCE: 38

```
Met Ala Gln Glu Val Thr Gln Ile Pro Ala Ala Leu Ser Val Pro Glu
1               5                   10                  15

Gly Glu Asn Leu Val Leu Asn Cys Ser Phe Thr Asp Ser Ala Ile Tyr
            20                  25                  30

Asn Leu Gln Trp Phe Arg Gln Asp Pro Gly Lys Gly Leu Thr Ser Leu
        35                  40                  45

Leu Leu Ile Gln Ser Ser Gln Arg Glu Gln Thr Ser Gly Arg Leu Asn
    50                  55                  60

Ala Ser Leu Asp Lys Ser Ser Gly Arg Ser Thr Leu Tyr Ile Ala Ala
65                  70                  75                  80

Ser Gln Pro Gly Asp Ser Ala Thr Tyr Leu Cys Ala Val Arg Pro Thr
                85                  90                  95

Ser Gly Gly Ser Tyr Ile Pro Thr Phe Gly Arg Gly Thr Ser Leu Ile
            100                 105                 110

Val His Pro Tyr Ile Gln Asn Pro Asp Pro Ala Val Cys Gln Leu Arg
        115                 120                 125

Asp Ser Lys Ser Ser Asp Lys Ser Val Cys Leu Phe Thr Asp Phe Asp
    130                 135                 140

Ser Gln Thr Asn Val Ser Gln Ser Lys Asp Ser Asp Val Tyr Ile Thr
145                 150                 155                 160

Asp Lys Thr Val Leu Asp Met Arg Ser Met Asp Phe Lys Ser Asn Ser
                165                 170                 175

Ala Val Ala Trp Ser Asn Lys Ser Asp Phe Ala Cys Ala Asn Ala Phe
            180                 185                 190

Asn Asn Ser Ile Ile Pro Glu Asp Thr Phe Phe Pro Ser Pro Glu Ser
        195                 200                 205

Ser
```

<210> SEQ ID NO 39
<211> LENGTH: 729
<212> TYPE: DNA
<213> ORGANISM: Artificial Sequence
<220> FEATURE:
<223> OTHER INFORMATION: Synthetic Polyribonucleotide

<400> SEQUENCE: 39

```
atgggcgtca cacaaacccc gaaatttcag gtgctgaaaa cgggtcagag catgaccctg      60
cagtgtgcgc aggatatgaa ccacgaatac atgagctggt atcgtcaaga tccgggtatg     120
ggtctgcgtc tgatccatta tagcgtgggt gcgggcatta ccgatcaggg tgaagtgccg     180
aacggttata tgttagccg tagcaccacc gaagattttc cgctgcgtct gctgagcgcg      240
gcgccgagcc agaccagcgt ttattttgc gcgagcagct atgttggtaa caccggcgaa      300
ctgttttttg gtgaaggcag ccgtctgacc gttctggaag atctgaaaaa cgtgtttccg     360
ccggaagttg cggttttga accgagcgaa gcgtgcatta gccataccca gaaagcgacc      420
ctggtttgtc tggcgaccgg ttttatccg gatcatgtgg aactgtcttg gtgggtgaac      480
ggcaaagaag tgcatagcgg tgtttctacc gatccgcagc cgctgaaaga cagccggcg      540
ctgaatgata gccgttatgc gctgtctagc cgtctgcgtg ttagcgcgac ctttttggcaa     600
aatccgcgta accattttcg ttgccaggtg cagttttatg gcctgagcga aaacgatgaa     660
tggacccagg atcgtgcgaa gccggttacc cagattgtta gcgcggaagc ctggggccgc     720
gcagattaa                                                              729
```

<210> SEQ ID NO 40
<211> LENGTH: 242
<212> TYPE: PRT
<213> ORGANISM: Artificial Sequence
<220> FEATURE:
<223> OTHER INFORMATION: Synthetic Polypeptide

<400> SEQUENCE: 40

```
Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Asn
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
            100                 105                 110

Glu Asp Leu Lys Asn Val Phe Pro Pro Glu Val Ala Val Phe Glu Pro
        115                 120                 125

Ser Glu Ala Cys Ile Ser His Thr Gln Lys Ala Thr Leu Val Cys Leu
    130                 135                 140

Ala Thr Gly Phe Tyr Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175
```

```
Glu Gln Pro Ala Leu Asn Asp Ser Arg Tyr Ala Leu Ser Ser Arg Leu
            180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Glu Ala Trp Gly Arg
225                 230                 235                 240

Ala Asp

<210> SEQ ID NO 41
<211> LENGTH: 615
<212> TYPE: DNA
<213> ORGANISM: Artificial Sequence
<220> FEATURE:
<223> OTHER INFORMATION: Synthetic Polyribonucleotide

<400> SEQUENCE: 41
atgggccaac tgctggaaca atccccgcaa ttcctgagta ttcaagaagg cgaaaatctg      60
acggtctact gtaattcatc atcggtcttt agctctctgc agtggtatcg tcaagaaccg     120
ggtgaaggtc cggtcctgct ggtgaccgtg gttacgggcg gtgaagtgaa aaagctgaaa     180
cgtctgacct ttcagttcgg cgatgcgcgc aaggacagtt ccctgcatat taccgcagca     240
cagccgggtg atacgggtct gtacctgtgc caggcgctg gtagccaagg taacctgatt      300
tttggcaagg gtacgaagct gagcgttaaa ccgaacatcc agaatccgga tccggccgtt     360
tgccagctgc gtgatagcaa aagcagcgat aaaagcgtgt gcctgttcac cgattttgat     420
agccagacca acgtgagcca gagcaaagat agcgatgtgt acatcaccga taaaccgtg      480 ctggatatgc gcagcatgga tttcaaaagc aatagcgcgg ttgcgtggag caacaaaagc     540
gattttgcgt gcgcgaacgc gtttaacaac agcatcatcc cggaagatac gttcttcccc     600
agcccagaaa gttcc                                                    615

<210> SEQ ID NO 42
<211> LENGTH: 205
<212> TYPE: PRT
<213> ORGANISM: Artificial Sequence
<220> FEATURE:
<223> OTHER INFORMATION: Synthetic Polypeptide

<400> SEQUENCE: 42

Met Gly Gln Leu Leu Glu Gln Ser Pro Gln Phe Leu Ser Ile Gln Glu
1               5                   10                  15

Gly Glu Asn Leu Thr Val Tyr Cys Asn Ser Ser Ser Val Phe Ser Ser
            20                  25                  30

Leu Gln Trp Tyr Arg Gln Glu Pro Gly Glu Gly Pro Val Leu Leu Val
        35                  40                  45

Thr Val Thr Gly Gly Glu Val Lys Lys Leu Lys Arg Leu Thr Phe
    50                  55                  60

Gln Phe Gly Asp Ala Arg Lys Asp Ser Ser Leu His Ile Thr Ala Ala
65                  70                  75                  80

Gln Pro Gly Asp Thr Gly Leu Tyr Leu Cys Ala Gly Ala Gly Ser Gln
                85                  90                  95

Gly Asn Leu Ile Phe Gly Lys Gly Thr Lys Leu Ser Val Lys Pro Asn
            100                 105                 110

Ile Gln Asn Pro Asp Pro Ala Val Cys Gln Leu Arg Asp Ser Lys Ser
        115                 120                 125
```

```
Ser Asp Lys Ser Val Cys Leu Phe Thr Asp Phe Asp Ser Gln Thr Asn
    130                 135                 140
Val Ser Gln Ser Lys Asp Ser Asp Val Tyr Ile Thr Asp Lys Thr Val
145                 150                 155                 160
Leu Asp Met Arg Ser Met Asp Phe Lys Ser Asn Ser Ala Val Ala Trp
                165                 170                 175
Ser Asn Lys Ser Asp Phe Ala Cys Ala Asn Ala Phe Asn Asn Ser Ile
            180                 185                 190
Ile Pro Glu Asp Thr Phe Phe Pro Ser Pro Glu Ser Ser
        195                 200                 205
```

<210> SEQ ID NO 43
<211> LENGTH: 735
<212> TYPE: DNA
<213> ORGANISM: Artificial Sequence
<220> FEATURE:
<223> OTHER INFORMATION: Synthetic Polyribonucleotide

<400> SEQUENCE: 43

```
atggtggacg gcggcattac ccaaagcccg aagtacctgt tcgcaagga aggccaaaat    60
gtgaccctgt cgtgtgaaca aaatctgaac catgatgcga tgtattggta ccgtcaggac   120
ccgggtcaag gtctgcgtct gatttattac agccagatcg tgaatgattt tcaaaaaggc   180
gacattgcag aaggttatag cgtgagccgt gaaaagaaag aatcttttcc gctgaccgtc   240
acgtccgctc agaagaaccc gaccgcgttc tacctgtgcg cgagcagcag ccgtagcagc   300
tatgaacaat actttggtcc gggtacgcgt ctgaccgtca cggaagatct gaaaaacgtg   360
tttccgccgg aagttgcggt ttttgaaccg agcgaagcgt gcattagcca tacccagaaa   420
gcgaccctgg tttgtctggc gaccggtttt tatccggatc atgtggaact gtcttggtgg   480
gtgaacggca agaagtgca tagcggtgtt tctaccgatc cgcagccgct gaaagaacag   540
ccggcgctga atgatagccg ttatgcgctg tctagccgtc tgcgtgttag cgcgaccttt   600
tggcaaaatc cgcgtaacca ttttcgttgc caggtgcagt tttatggcct gagcgaaaac   660
gatgaatgga cccaggatcg tgcgaagccg gttacccaga ttgttagcgc ggaagcctgg   720
ggccgcgcag attaa                                                    735
```

<210> SEQ ID NO 44
<211> LENGTH: 244
<212> TYPE: PRT
<213> ORGANISM: Artificial Sequence
<220> FEATURE:
<223> OTHER INFORMATION: Synthetic Polypeptide

<400> SEQUENCE: 44

```
Met Val Asp Gly Gly Ile Thr Gln Ser Pro Lys Tyr Leu Phe Arg Lys
1               5                  10                  15
Glu Gly Gln Asn Val Thr Leu Ser Cys Glu Gln Asn Leu Asn His Asp
                20                  25                  30
Ala Met Tyr Trp Tyr Arg Gln Asp Pro Gly Gln Gly Leu Arg Leu Ile
            35                  40                  45
Tyr Tyr Ser Gln Ile Val Asn Asp Phe Gln Lys Gly Asp Ile Ala Glu
        50                  55                  60
Gly Tyr Ser Val Ser Arg Glu Lys Lys Glu Ser Phe Pro Leu Thr Val
65                  70                  75                  80
Thr Ser Ala Gln Lys Asn Pro Thr Ala Phe Tyr Leu Cys Ala Ser Ser
                85                  90                  95
```

Ser Arg Ser Ser Tyr Glu Gln Tyr Phe Gly Pro Gly Thr Arg Leu Thr
            100                 105                 110

Val Thr Glu Asp Leu Lys Asn Val Phe Pro Pro Glu Val Ala Val Phe
        115                 120                 125

Glu Pro Ser Glu Ala Cys Ile Ser His Thr Gln Lys Ala Thr Leu Val
    130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val Ser Thr Asp Pro Gln Pro
                165                 170                 175

Leu Lys Glu Gln Pro Ala Leu Asn Asp Ser Arg Tyr Ala Leu Ser Ser
            180                 185                 190

Arg Leu Arg Val Ser Ala Thr Phe Trp Gln Asn Pro Arg Asn His Phe
        195                 200                 205

Arg Cys Gln Val Gln Phe Tyr Gly Leu Ser Glu Asn Asp Glu Trp Thr
    210                 215                 220

Gln Asp Arg Ala Lys Pro Val Thr Gln Ile Val Ser Ala Glu Ala Trp
225                 230                 235                 240

Gly Arg Ala Asp

<210> SEQ ID NO 45
<211> LENGTH: 630
<212> TYPE: DNA
<213> ORGANISM: Artificial Sequence
<220> FEATURE:
<223> OTHER INFORMATION: Synthetic Polyribonucleotide

<400> SEQUENCE: 45

```
atgggtaagc aggaagtgac ccagatccct gccgccctga gcgtgcccga gggcgagaac    60
ctggtgctga actgcagctt caccgacagc gccatctaca acctgcagtg gttccggcag   120
gaccccggca agggcctgac cagcctgctg ctggtgcgtc cgtatcagcg ggagcagacc   180
agcggcagac tgaacgccag cctggacaag agcagcggca agcacccct gtatatcgcc   240
gccagccagc ccggcgactc cgccacctac ctgtgcgctg tgcggcctgg cggagcggc    300
agctaccagc tgaccttcgg caagggcacc aagctgtccg tgatcccca atatccagaat   360
ccggatccgg ccgtttgcca gctgcgtgat agcaaaagca gcgataaaag cgtgtgcctg   420
ttcaccgatt tgatagcca gaccaacgtg agccagagca agatagcga tgtgtacatc     480
accgataaaa ccgtgctgga tatgcgcagc atggatttca aaagcaatag cgcggttgcg   540
tggagcaaca aaagcgattt tgcgtgcgcg aacgcgttta caacagcat catcccggaa    600
gatacgttct tccccagccc agaaagttcc                                   630
```

<210> SEQ ID NO 46
<211> LENGTH: 210
<212> TYPE: PRT
<213> ORGANISM: Artificial Sequence
<220> FEATURE:
<223> OTHER INFORMATION: Synthetic Polypeptide

<400> SEQUENCE: 46

Met Gly Lys Gln Glu Val Thr Gln Ile Pro Ala Ala Leu Ser Val Pro
1               5                   10                  15

Glu Gly Glu Asn Leu Val Leu Asn Cys Ser Phe Thr Asp Ser Ala Ile
            20                  25                  30

Tyr Asn Leu Gln Trp Phe Arg Gln Asp Pro Gly Lys Gly Leu Thr Ser
        35                  40                  45

```
Leu Leu Leu Val Arg Pro Tyr Gln Arg Glu Gln Thr Ser Gly Arg Leu
 50                  55                  60

Asn Ala Ser Leu Asp Lys Ser Ser Gly Arg Ser Thr Leu Tyr Ile Ala
 65                  70                  75                  80

Ala Ser Gln Pro Gly Asp Ser Ala Thr Tyr Leu Cys Ala Val Arg Pro
                 85                  90                  95

Gly Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Cys Gln Leu
        115                 120                 125

Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser
    210

<210> SEQ ID NO 47
<211> LENGTH: 735
<212> TYPE: DNA
<213> ORGANISM: Artificial Sequence
<220> FEATURE:
<223> OTHER INFORMATION: Synthetic Polyribonucleotide

<400> SEQUENCE: 47
atgggtaaag ctggagttac tcaaactcca agatatctga tcaaaacgag aggacagcaa      60
gtgacactga gctgctcccc tatctctggg cataggagtg tatcctggta ccaacagacc     120
ccaggacagg gccttcagtt cctctttgaa tacttcagtg agacacagag aaacaaagga     180
aacttccctg gtcgattctc agggcgccag ttctctaact ctcgctctga gatgaatgtg     240
agcaccttgg agctggggga ctcggccctt tatctttgcg ccagcagccc gaacatggcc     300
gacgagcagt acttcgggcc gggcaccagg ctcacggtca cagaagatct gaaaaacgtg     360
tttccgccgg aagttgcggt ttttgaaccg agcgaagcgt gcattagcca tacccagaaa     420
gcgaccctgg tttgtctggc gaccggtttt tatccggatc atgtggaact gtcttggtgg     480
gtgaacggca agaagtgcag tagcggtgtt tctaccgatc cgcagccgct gaaagaacag     540
ccggcgctga atgatagccg ttatgcgctg tctagccgtc tgcgtgttag cgcgaccttt     600
tggcaaaatc cgcgtaacca ttttcgttgc caggtgcagt ttatggcct gagcgaaaac     660 gatgaatgga cccaggatcg tgcgaagccg gttacccaga ttgttagcgc ggaagcctgg     720
ggccgcgcag attaa                                                      735

<210> SEQ ID NO 48
<211> LENGTH: 244
<212> TYPE: PRT
<213> ORGANISM: Artificial Sequence
<220> FEATURE:
<223> OTHER INFORMATION: Synthetic Polypeptide
```

-continued

<400> SEQUENCE: 48

Met Gly Lys Ala Gly Val Thr Gln Thr Pro Arg Tyr Leu Ile Lys Thr
1               5                   10                  15

Arg Gly Gln Gln Val Thr Leu Ser Cys Ser Pro Ile Ser Gly His Arg
            20                  25                  30

Ser Val Ser Trp Tyr Gln Thr Pro Gly Gln Gly Leu Gln Phe Leu
        35                  40                  45

Phe Glu Tyr Phe Ser Glu Thr Gln Arg Asn Lys Gly Asn Phe Pro Gly
50                  55                  60

Arg Phe Ser Gly Arg Gln Phe Ser Asn Ser Arg Ser Glu Met Asn Val
65                  70                  75                  80

Ser Thr Leu Glu Leu Gly Asp Ser Ala Leu Tyr Leu Cys Ala Ser Ser
                85                  90                  95

Pro Asn Met Ala Asp Glu Gln Tyr Phe Gly Pro Gly Thr Arg Leu Thr
            100                 105                 110

Val Thr Glu Asp Leu Lys Asn Val Phe Pro Pro Glu Val Ala Val Phe
        115                 120                 125

Glu Pro Ser Glu Ala Cys Ile Ser His Thr Gln Lys Ala Thr Leu Val
    130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val Ser Thr Asp Pro Gln Pro
                165                 170                 175

Leu Lys Glu Gln Pro Ala Leu Asn Asp Ser Arg Tyr Ala Leu Ser Ser
            180                 185                 190

Arg Leu Arg Val Ser Ala Thr Phe Trp Gln Asn Pro Arg Asn His Phe
        195                 200                 205

Arg Cys Gln Val Gln Phe Tyr Gly Leu Ser Glu Asn Asp Glu Trp Thr
    210                 215                 220

Gln Asp Arg Ala Lys Pro Val Thr Gln Ile Val Ser Ala Glu Ala Trp
225                 230                 235                 240

Gly Arg Ala Asp

<210> SEQ ID NO 49
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 49

Glu Glu Tyr Leu Lys Ala Trp Thr Phe
1               5

<210> SEQ ID NO 50
<211> LENGTH: 41
<212> TYPE: DNA
<213> ORGANISM: Artificial Sequence
<220> FEATURE:
<223> OTHER INFORMATION: Synthetic Polyribonucleotide

<400> SEQUENCE: 50
gataaatgcg tgctggatat gtgcagcatg gatttcaaaa g         41

<210> SEQ ID NO 51
<211> LENGTH: 41
<212> TYPE: DNA
<213> ORGANISM: Artificial Sequence

```
<220> FEATURE:
<223> OTHER INFORMATION: Synthetic Polyribonucleotide

<400> SEQUENCE: 51
cttttgaaat ccatgctgca catatccagc acgcatttat c                              41

<210> SEQ ID NO 52
<211> LENGTH: 34
<212> TYPE: DNA
<213> ORGANISM: Artificial Sequence
<220> FEATURE:
<223> OTHER INFORMATION: Synthetic Polyribonucleotide

<400> SEQUENCE: 52
ggcaaagaag tgcattgcgg tgtttgtacc gatc                                     34

<210> SEQ ID NO 53
<211> LENGTH: 34
<212> TYPE: DNA
<213> ORGANISM: Artificial Sequence
<220> FEATURE:
<223> OTHER INFORMATION: Synthetic Polypeptide

<400> SEQUENCE: 53
gatcggtaca aacaccgcaa tgcacttctt tgcc                                     34

<210> SEQ ID NO 54
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 54

Lys Leu Val Ala Leu Gly Ile Asn Ala Val
1               5                   10

<210> SEQ ID NO 55
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 55

Ser Leu Leu Met Trp Ile Thr Gln Cys
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 56

Gly Ile Leu Gly Phe Val Phe Thr Leu
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic Polypeptide
```

<400> SEQUENCE: 57

Glu Val Asp Pro Ile Gly His Leu Tyr
1               5

<210> SEQ ID NO 58
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 58

Ser Ser Cys Ser Ser Cys Pro Leu Ser Lys
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 59

Lys Tyr Lys Asp Tyr Phe Pro Val Ile
1               5

<210> SEQ ID NO 60
<211> LENGTH: 35
<212> TYPE: PRT
<213> ORGANISM: Artificial Sequence
<220> FEATURE:
<223> OTHER INFORMATION: Synthetic Polyribonucleotide

<400> SEQUENCE: 60

Cys Gly Gly Ala Ala Gly Ala Thr Ala Cys Gly Thr Thr Cys Thr Thr
1               5                   10                  15

Cys Thr Gly Cys Ala Gly Cys Cys Ala Gly Ala Ala Ala Gly Thr
                20                  25                  30

Thr Cys Cys
        35

<210> SEQ ID NO 61
<211> LENGTH: 35
<212> TYPE: DNA
<213> ORGANISM: Artificial Sequence
<220> FEATURE:
<223> OTHER INFORMATION: Synthetic Polyribonucleotide

<400> SEQUENCE: 61
ggaactttct gggctgcaga agaacgtatc ttccg                            35

<210> SEQ ID NO 62
<211> LENGTH: 36
<212> TYPE: DNA
<213> ORGANISM: Artificial Sequence
<220> FEATURE:
<223> OTHER INFORMATION: Synthetic Polyribonucleotide

<400> SEQUENCE: 62
gtttttgaac cgagcgaatg cgaaattagc catacc                           36

<210> SEQ ID NO 63
<211> LENGTH: 36
<212> TYPE: DNA
<213> ORGANISM: Artificial Sequence

```
<220> FEATURE:
<223> OTHER INFORMATION: Synthetic Polyribonucleotide

<400> SEQUENCE: 63
ggtatggcta atttcgcatt cgctcggttc aaaaac                                36

<210> SEQ ID NO 64
<211> LENGTH: 33
<212> TYPE: DNA
<213> ORGANISM: Artificial Sequence
<220> FEATURE:
<223> OTHER INFORMATION: Synthetic Polyribonucleotide

<400> SEQUENCE: 64
ccggatccgg ccgtttgcca gctgcgtgat agc                                   33

<210> SEQ ID NO 65
<211> LENGTH: 33
<212> TYPE: DNA
<213> ORGANISM: Artificial Sequence
<220> FEATURE:
<223> OTHER INFORMATION: Synthetic Polyribonucleotide

<400> SEQUENCE: 65
gctatcacgc agctggcaaa cggccggatc cgg                                   33

<210> SEQ ID NO 66
<211> LENGTH: 33
<212> TYPE: DNA
<213> ORGANISM: Artificial Sequence
<220> FEATURE:
<223> OTHER INFORMATION: Synthetic Polyribonucleotide

<400> SEQUENCE: 66
gaaccgagcg aagcgtgcat tagccatacc cag                                   33

<210> SEQ ID NO 67
<211> LENGTH: 33
<212> TYPE: DNA
<213> ORGANISM: Artificial Sequence
<220> FEATURE:
<223> OTHER INFORMATION: Synthetic Polyribonucleotide

<400> SEQUENCE: 67
ctgggtatgg ctaatgcacg cttcgctcgg ttc                                   33

<210> SEQ ID NO 68
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 68

Ile Gln Asn Pro Asp Pro Ala Val Tyr Gln Leu Arg Asp Ser Lys Ser
1               5                   10                  15

Ser Asp Lys Ser
            20

<210> SEQ ID NO 69
<211> LENGTH: 20
<212> TYPE: PRT
<213> ORGANISM: Artificial Sequence
<220> FEATURE:
<223> OTHER INFORMATION: Synthetic Polypeptide
```

```
<400> SEQUENCE: 69

Ile Thr Asp Lys Thr Val Leu Asp Met Arg Ser Met Asp Phe Lys Ser
1               5                   10                  15

Asn Ser Ala Val
            20

<210> SEQ ID NO 70
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 70

Ser Ile Ile Pro Glu Asp Thr Phe Phe Cys Ser Pro Glu Ser Ser Ser
1               5                   10                  15

Ala Ala Ala Leu
            20

<210> SEQ ID NO 71
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 71

Glu Val Ala Val Phe Glu Pro Ser Glu Ala Glu Ile Ser His Thr Gln
1               5                   10                  15

Lys Ala Thr Leu
            20

<210> SEQ ID NO 72
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 72

Trp Trp Val Asn Gly Lys Glu Val His Ser Gly Val Ser Thr Asp Pro
1               5                   10                  15

Gln Pro Leu Lys
            20

<210> SEQ ID NO 73
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 73

Glu Val Ala Val Phe Glu Pro Ser Glu Ala Glu Ile Ser His Thr Gln
1               5                   10                  15

Lys Ala Thr Leu
            20

<210> SEQ ID NO 74
<211> LENGTH: 24
<212> TYPE: PRT
<213> ORGANISM: Artificial Sequence
<220> FEATURE:
<223> OTHER INFORMATION: Synthetic Polypeptide
```

```
<400> SEQUENCE: 74

Ile Gln Asn Pro Glu Pro Ala Val Tyr Gln Leu Lys Asp Pro Arg Ser
1               5                   10                  15

Gln Asp Ser Thr Leu Cys Leu Phe
            20

<210> SEQ ID NO 75
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 75

Gly Thr Phe Ile Thr Asp Lys Thr Val Leu Asp Met Lys Ala Met Asp
1               5                   10                  15

Ser Lys Ser Asn Gly Ala
            20

<210> SEQ ID NO 76
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 76

Gln Asp Ile Phe Lys Glu Thr Asn Ala Thr Tyr Pro Ser Ser
1               5                   10

<210> SEQ ID NO 77
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 77

Phe Pro Pro Glu Val Ala Val Phe Glu Pro Ser Glu Ala Glu Ile Ser
1               5                   10                  15

His Thr Gln Lys Ala Thr Leu Val Cys Leu Ala Thr
            20                  25

<210> SEQ ID NO 78
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 78

Leu Ser Trp Trp Val Asn Gly Lys Glu Val His Ser Gly Val Ser Thr
1               5                   10                  15

Asp Pro Gln Ala Tyr Lys Glu Ser Asn
            20                  25

<210> SEQ ID NO 79
<211> LENGTH: 28
<212> TYPE: PRT
<213> ORGANISM: Artificial Sequence
<220> FEATURE:
<223> OTHER INFORMATION: Synthetic Polypeptide
```

```
<400> SEQUENCE: 79

Phe Pro Pro Glu Val Ala Val Phe Glu Pro Ser Glu Ala Glu Ile Ser
1               5                   10                  15

His Thr Gln Lys Ala Thr Leu Val Cys Leu Ala Thr
            20                  25
```

SOLUBLE HETERODIMERIC T CELL RECEPTOR, AND PREPARATION METHOD AND USE THEREOF

REFERENCE TO SUBMISSION OF A SEQUENCE LISTING AS A TEXT FILE

The Sequence Listing written in file Sequence_Listing_1048028.txt created on Jul. 13, 2018, 87,604 bytes, machine format IBM-PC, MS-Windows operating system, is hereby incorporated by reference in its entirety for all purposes.

TECHNICAL FIELD

The present invention relates to field of biomedicine, and particularly to a highly stable soluble T cell receptor, and preparation method and use thereof.

BACKGROUND ART

There are only two types of molecules that can recognize antigens in a specific manner. One is immunoglobulin or antibody and the other is T cell receptor (TCR), which is α/β or γ/δ heterodimeric glycoprotein on cell membrane. The physical repertoire of TCR of immune system is generated in thymus through V (D) J recombination, followed by positive and negative selections. In peripheral environment, TCRs mediate the recognition of specific Major Histocompatibility Complex-peptide complexes (pMHC) by T cells and, as such, are essential to the immunological functioning of cells in the immune system.

TCR is the only receptor for presenting particular peptide antigens in Major Histocompatibility Complex (MHC). The exogenous or endogenous peptides may be the only sign of abnormality in a cell. In the immune system, once antigen-specific TCRs bind with pMHC complexes, it causes direct physical contact of a T-cell and an antigen presenting cell (APC). Then, the interaction of other membrane molecules in T cell and APC occurs and the subsequent cell signaling and other physiological responses are initiated so that a range of different antigen-specific T cells exert immune effects on their targets.

On T cell membrane, the TCR is associated with invariant proteins of CD3 involved in mediating signal transduction to form a complex. TCRs exist in many forms, which are structurally similar but T cells expressing them have quite distinct anatomical locations and probably have different functions. The extracellular portion of TCR consists of two membrane-proximal constant domains, and two membrane-distal variable domains. The variable domains contain polymorphic loops analogous to the complementary determining regions (CDRs) of antibodies. It is these loops that form the binding site of the TCR molecule and determine peptide specificity. The MHC class I and class II ligands corresponding to TCR are also immunoglobulin superfamily proteins but are specialized for antigen presentation, with a polymorphic peptide binding site which enables them to present a diverse array of short peptide fragments at APC cell surface.

Just like an immunoglobulin (antibody) can be used as an antigen recognition molecule, TCR can be developed for diagnostic and therapeutic applications. Soluble TCRs have a wide range of uses, and are useful not only in study of interaction of TCR-pMHC but also as a diagnostic tool for detecting infection or as a marker for autoimmune disease. Similarly, soluble TCRs can be used to deliver a therapeutic agent, such as a cytotoxic compound or an immunostimulatory compound, to cells presenting specific antigens or to inhibit T cells (e.g., the T cells which react with autoimmune peptide antigens). Further, soluble TCRs can be bound with other molecules (e.g., anti-CD3 antibodies) and re-directed so as to target cells which present specific antigens. For expression of a soluble TCR in *E. coli*, when TCR is separated from membrane, its instability and low yield of protein become major obstacles for development of a therapeutic or diagnostic agent based on TCR or fragments thereof.

The naturally occurring TCR is a membrane protein which is stabilized by its transmembrane region, so it is very difficult for a soluble TCR expressed in bacteria to form a high stability TCR that retains a specific binding ability to its original ligand (i.e., pMHC) and has a high stability, as described in patent WO99/18129. Some references have described truncated TCRs containing only an extracellular region or containing only extracellular and cytoplasmic regions. Although such TCRs can be recognized by TCR-specific antibodies, the yield is low and they can not recognize major histocompatibility complex-peptide complexes under low concentrations, indicating that such TCRs are instable and vulnerable to denaturation.

Reiter et al. (Immunity, 1995, 2: 281-287) have described construction of soluble molecules of disulfide-stabilized TCR α and β variable domains wherein a variable domain is associated with a truncated *Pseudomonas* exotoxin (PE38). The position of the new disulfide bond in TCR variable domain is identified by analyzing homology to variable domain of antibody (see Brinkmann et al. (1993), Proc. Natl. Acad. Sci USA 90: 7538-7542; and Reiter et al. (1994) Biochemistry 33: 5451-5459). The stability of TCR can be improved by forming an inter-chain disulfide bond via mutating a non-cysteine residue in constant domain of TCR into cysteine. However, there is no such homology between antibody constant domain and TCR constant domain. Therefore, this technique can not be used to identify suitable sites of new inter-chain disulfide bond between TCR constant domains.

Theoretically, there are many sites in the TCR for forming an artificial inter-chain disulfide bond. However, it is very difficult to find a suitable site for formation of an artificial interchain disulfide bond in the TCR so that a TCR containing such an artificial interchain disulfide bond can be successfully renatured, refolded, thereby obtaining a TCR with high yield, high stability, and specific binding activity with its original ligand. The skilled in the art are committed to development of a TCR which contains an artificial inter-chain disulfide bond, can be sufficiently renatured, refolded, and purified, has high stability, high yield after refolding and can specifically bind to the original ligand.

SUMMARY OF THE INVENTION

The object of the present invention is to provide a soluble and highly stable T cell receptor, and preparation method and use thereof.

In the first aspect of the invention, it provides a T cell receptor (TCR) which has an artificial interchain disulfide bond formed by introducing a cysteine residue into TCR α chain and/or β chain constant region, wherein the TCR having an artificial interchain disulfide bond has a Tm≥45° C.

In a preferred embodiment, the cysteine residue is introduced into the β chain constant region of TCR at a substitution position selected from the group consisting of: 54S, 19A and 20E in Exon 1 of TRBC1*01 or TRBC2*01.

In a preferred embodiment, the cysteine residue is introduced into the α chain constant region of TCR at a substitution position selected from the group consisting of: 53R, 89P and 10Y in Exon 1 of TRAC1*01.

In a preferred embodiment, the TCR comprises: (i) all or part of the TCR α chain other than its transmembrane domain, and (ii) all or part of the TCR β chain other than its transmembrane domain, wherein (i) and (ii) each comprises a functional variable domain and at least a portion of a constant domain of TCR chain.

In a preferred embodiment, the TCR is soluble.

In a preferred embodiment, the TCR does not have any natural interchain disulfide bond.

In a preferred embodiment, the C-terminus of the native TCR is truncated in the TCR so that a cysteine residue for forming a natural interchain disulfide bond is removed.

In a preferred embodiment, a cysteine residue for forming a natural interchain disulfide bond is substituted with another residue.

In a preferred embodiment, the TCR β chain constant region has no unpaired cysteine residue.

In a preferred embodiment, the unpaired cysteine residue in the TCR β chain constant region is substituted into Ala or Ser.

In a preferred embodiment, the cysteine residues that form an artificial interchain disulfide bond are at a substitution position selected from the group consisting of:

53R in Exon 1 of TRAC*01, and 54S in Exon 1 of TRBC1*01 or TRBC2*01;

89P in Exon 1 of TRAC*01, and 19A in Exon 1 of TRBC1*01 or TRBC2*01; and 10Y in Exon 1 of TRAC*01, and 20E in Exon 1 of TRBC1*01 or TRBC2*01.

In a preferred embodiment, a combination of α chain variable domain and β chain variable domain of the TCR is selected from the group consisting of:

an extracellular α (alpha) chain amino acid sequence as shown in SEQ ID NO.: 2, and an extracellular β (beta) chain amino acid sequence as shown in SEQ ID NO.: 4:

an extracellular α chain amino acid sequence as shown in SEQ ID NO.: 6 and an extracellular β chain amino acid sequence as shown in SEQ ID NO: 8;

an extracellular α chain amino acid sequence as shown in SEQ ID NO.: 10 and an extracellular β chain amino acid sequence as shown in SEQ ID NO: 12;

an extracellular α chain amino acid sequence as shown in SEQ ID NO.: 14 and an extracellular β chain amino acid sequence as shown in SEQ ID NO: 16;

an extracellular α chain amino acid sequence as shown in SEQ ID NO.: 18 and an extracellular β chain amino acid sequence as shown in SEQ ID NO.: 20;

an extracellular α chain amino acid sequence as shown in SEQ ID NO.: 22, and an extracellular β chain amino acid sequence as shown in SEQ ID NO: 24;

an extracellular α chain amino acid sequence as shown in SEQ ID NO.: 26, and an extracellular β chain amino acid sequence as shown in SEQ ID NO: 28:

an extracellular α chain amino acid sequence as shown in SEQ ID NO: 30 and an extracellular β chain amino acid sequence as shown in SEQ ID NO: 32;

an extracellular α chain amino acid sequence shown in SEQ ID NO.: 34 and an extracellular β chain amino acid sequence as shown in SEQ ID NO: 36;

an extracellular α chain amino acid sequence as shown in SEQ ID NO.: 38 and an extracellular β chain amino acid sequence as shown in SEQ ID NO.:40:

an extracellular α chain amino acid sequence as shown in SEQ ID NO.: 42 and an extracellular β chain amino acid sequence as shown in SEQ ID NO: 44; and an extracellular α chain amino acid sequence as shown in SEQ ID NO.: 46, and an extracellular β chain amino acid sequence as shown in SEQ ID NO::48.

In a preferred embodiment, a conjugate is linked to C- or N-terminal of the TCR α and/or β chains.

In a preferred embodiment, the conjugate is selected from the group consisting of: a detectable marker; a therapeutic agent; a PK modifying moiety and a combination thereof.

Preferably, the detectable marker comprises: a fluorescent or luminescent label, a radiolabel, a MRI (magnetic resonance imaging) or CT (computer tomography X-ray) contrast agent, or an enzyme capable of producing a detectable product.

Preferably, the therapeutic agent comprises: a radionuclide, a biotoxin, a cytokine (e.g., IL-2, etc.), an antibody, an antibody Fc fragment, a scFv antibody fragment, a gold nanoparticle/nanorod, a virus particle, a liposome, a nanomagnetic particle, a prodrug activating enzyme (e.g., DT-diaphorase (DTD) or a biphenyl hydrolase-like protein (BPHL)), a chemotherapeutic agent (e.g., cisplatin) or a nano-particle in any form.

In a preferred embodiment, the therapeutic agent bound with the TCR is an antibody against CD3 or any protein, small molecule compound or organic macromolecule compound that specifically binds to CD3 which is linked at C- or N-terminal of the TCR α and/or β chains.

In the second aspect of the invention, it provides a nucleic acid molecule comprising a sequence encoding an α chain and/or a β chain of the TCR according to the first aspect of the invention, or its complementary sequence.

In the third aspect of the invention, it provides a vector comprising a nucleic acid molecule according to the second aspect of the invention.

In the fourth aspect of the invention, it provides a host cell or a genetically engineered cell which comprises a vector according to the third aspect of the invention or in which an exogenous nucleic acid molecule according to the second aspect of the invention is integrated in a chromosome.

In a preferred embodiment, the host cell or the genetically engineered cell is selected from the group consisting of: a prokaryotic and an eukaryotic cell, such as an *Escherichia coli*, a yeast, a CHO cell and so on.

In the fifth aspect of the invention, it provides an isolated cell which expresses a TCR according to the first aspect of the invention In the sixth aspect of the invention, it provides a method for preparing a TCR according to the first aspect of the invention, which comprises:

(i) culturing the host cell according to the fourth aspect of the invention, thereby expressing an α chain and/or β chain of the TCR in the first aspect of the invention; and (ii) isolating or purifying the α chain and/or β chain:

(iii) refolding the α chain and/or β chain, thereby obtaining the TCR.

In the seventh aspect of the invention, it provides a TCR complex comprising one or more TCR molecules in the first aspect of the invention.

In a preferred embodiment, the complex comprises a complex formed by the TCR of the invention bound with a therapeutic agent or a detectable marker.

In a preferred embodiment, the complex comprises two or more TCR molecules.

In the eighth aspect of the invention, it provides a use of the TCR of the first aspect of the invention for manufacture of a medicine for treating tumor, viral infection or autoimmune disease or a reagent for detecting MHC-peptide complexes.

In the ninth aspect of the invention, it provides a pharmaceutical composition comprising a pharmaceutically acceptable carrier and a safe and effective dosage of a TCR of the first aspect of the invention, a cell of the fourth aspect of the invention, or a TCR complex of the seventh aspect of the invention.

In the tenth aspect of the invention, it provides a method for treating a disease which comprises administering the TCR of the first aspect of the invention, a cell of the fifth aspect of the invention, or the TCR complex of the seventh aspect of the invention, or a pharmaceutical composition of the ninth aspect of the invention to a subject in need of.

Preferably, the disease comprises tumor, autoimmune disease or viral infection.

It should be understood that in the present invention, the technical features specifically described above and below (such as the examples) can be combined with each other, thereby constituting a new or preferred technical solution, which needs not be specified one by one.

DESCRIPTION OF FIGURES

FIGS. 1a and 1b respectively show the extracellular α chain amino acid sequence of LC13TCR in which a cysteine is introduced at position 53 of TRAC*01 exon 1, and the extracellular β chain amino acid sequence of LC13TCR in which a cysteine is introduced at position 54 of exon 1 of TRBC1*01 or TRBC2*01.

FIGS. 2a and 2b respectively show the nucleotide sequences corresponding to the amino acid sequences in FIGS. 1a and 1b.

FIG. 3 shows an elution curve of gel filtration column after refolding the TCR α and β chains as shown in FIGS. 1a and 1b.

FIG. 4 shows the SEC spectrum of the TCR α and β chains as shown in FIGS. 1a and 1b after refolding and protein purification.

FIG. 5 shows a DSC thermogram of the TCR α and β chains as shown in FIGS. 1a and 1b after refolding and protein purification.

FIG. 6 shows binding curves of LC13TCR molecules at different concentrations with its corresponding antigen after refolding the TCR α and β chains as shown in FIGS. 1a and 1b and protein purification.

FIGS. 7a and 7b respectively show the extracellular α chain amino acid sequence of 1G4TCR in which a cysteine is introduced at position 53 of TRAC*01 exon 1, and the extracellular β chain amino acid sequence of 1G4TCR in which a cysteine is introduced at position 54 of exon 1 of TRBC1*01 or TRBC2*01.

FIGS. 8a and 8b respectively show the nucleotide sequences corresponding to the amino acid sequences in FIGS. 7a and 7b.

FIG. 9 shows an elution curve of gel filtration column after refolding the TCR α and β chains as shown in FIGS. 7a and 7b.

FIG. 10 shows the SEC spectrum of the TCR α and β chains as shown in FIGS. 7a and 7b after refolding and protein purification.

FIG. 11 shows a DSC thermogram of the TCR α and β chains as shown in FIGS. 7a and 7b after refolding and protein purification.

FIG. 12 shows binding curves of 1G4TCR molecules at different concentrations with its corresponding antigen after refolding the TCR α and β chains as shown in FIGS. 7a and 7b and protein purification.

FIGS. 13a and 13b respectively show the extracellular α chain amino acid sequence of JM22TCR in which a cysteine is introduced at position 53 of TRAC*01 exon 1, and the extracellular β chain amino acid sequence of JM22TCR in which a cysteine is introduced at position 54 of exon 1 of TRBC1*01 or TRBC2*01.

FIGS. 14a and 14b respectively show the nucleotide sequences corresponding to the amino acid sequences in FIGS. 13a and 13b.

FIG. 15 shows an elution curve of gel filtration column after refolding the TCR α and β chains as shown in FIGS. 13a and 13b.

FIG. 16 shows the SEC spectrum of the TCR α and β chains as shown in FIGS. 13a and 13b after refolding and protein purification.

FIG. 17 shows a DSC thermogram of the TCR α and β chains as shown in FIGS. 13a and 13b after refolding and protein purification.

FIG. 18 shows binding curves of JM22TCR molecules at different concentrations with its corresponding antigen after refolding the TCR α and β chains as shown in FIGS. 13a and 13b and protein purification.

FIGS. 19a and 19b respectively show the extracellular α chain amino acid sequence of MGA3TCR in which a cysteine is introduced at position 53 of TRAC*01 exon 1, and the extracellular β chain amino acid sequence of MGA3TCR in which a cysteine is introduced at position 54 of exon 1 of TRBC1*01 or TRBC2*01.

FIGS. 20a and 20b respectively show the nucleotide sequences corresponding to the amino acid sequences in FIGS. 19a and 19b.

FIG. 21 shows an elution curve of gel filtration column after refolding the TCR α and β chains as shown in FIGS. 19a and 19b.

FIG. 22 shows the SEC spectrum of the TCR α and β chains as shown in FIGS. 19a and 19b after refolding and protein purification.

FIG. 23 shows a DSC thermogram of the TCR α and β chains as shown in FIGS. 19a and 19b after refolding and protein purification.

FIG. 24 shows binding curves of MGA3TCR molecules at different concentrations with its corresponding antigen after refolding the TCR α and β chains as shown in FIGS. 19a and 19b and protein purification.

FIGS. 25a and 25b respectively show the extracellular α chain amino acid sequence of LC13TCR in which a cysteine is introduced at position 89 of TRAC*01 exon 1, and the extracellular β chain amino acid sequence of LC13TCR in which a cysteine is introduced at position 19 of exon 1 of TRBC1*01 or TRBC2*01.

FIGS. 26a and 26b respectively show the nucleotide sequences corresponding to the amino acid sequences in FIGS. 25a and 25b.

FIG. 27 shows an elution curve of gel filtration column after refolding the TCR α and β chains as shown in FIGS. 25a and 25b.

FIG. 28 shows the SEC spectrum of the TCR α and β chains as shown in FIGS. 25a and 25b after refolding and protein purification.

FIG. 29 shows a DSC thermogram of the TCR α and β chains as shown in FIGS. 25a and 25b after refolding and protein purification.

FIG. 30 shows binding curves of LC13TCR molecules at different concentrations with its corresponding antigen after refolding the TCR α and β chains as shown in FIGS. 25a and 25b and protein purification.

FIGS. 31a and 31b respectively show the extracellular α chain amino acid sequence of 1G4TCR in which a cysteine is introduced at position 89 of TRAC*01 exon 1, and the extracellular β chain amino acid sequence of 1G4TCR in which a cysteine is introduced at position 19 of exon 1 of TRBC1*01 or TRBC2*01.

FIGS. 32a and 32b respectively show the nucleotide sequences corresponding to the amino acid sequences in FIGS. 31a and 31b.

FIG. 33 shows an elution curve of gel filtration column after refolding the TCR α and β chains as shown in FIGS. 31a and 31b.

FIG. 34 shows the SEC spectrum of the TCR α and β chains as shown in FIGS. 31a and 31b after refolding and protein purification.

FIG. 35 shows a DSC thermogram of the TCR α and β chains as shown in FIGS. 31a and 31b after refolding and protein purification.

FIG. 36 shows binding curves of 1G4TCR molecules at different concentrations with its corresponding antigen after refolding the TCR α and β chains as shown in FIGS. 31a and 31b and protein purification.

FIGS. 37a and 37b respectively show the extracellular α chain amino acid sequence of JM22TCR in which a cysteine is introduced at position 89 of TRAC*01 exon 1, and the extracellular β chain amino acid sequence of JM22TCR in which a cysteine is introduced at position 19 of exon 1 of TRBC1*01 or TRBC2*01.

FIGS. 38a and 38b respectively show the nucleotide sequences corresponding to the amino acid sequences in FIGS. 37a and 37b.

FIG. 39 shows an elution curve of gel filtration column after refolding the TCR α and β chains as shown in FIGS. 37a and 37b.

FIG. 40 shows the SEC spectrum of the TCR α and β chains as shown in FIGS. 37a and 37b after refolding and protein purification.

FIG. 41 shows a DSC thermogram of the TCR α and β chains as shown in FIGS. 37a and 37b after refolding and protein purification.

FIG. 42 shows binding curves of JM22TCR molecules at different concentrations with its corresponding antigen after refolding the TCR α and β chains as shown in FIGS. 37a and 37b and protein purification.

FIGS. 43a and 43b respectively show the extracellular α chain amino acid sequence of MGA3TCR in which a cysteine is introduced at position 89 of TRAC*01 exon 1, and the extracellular β chain amino acid sequence of MGA3TCR in which a cysteine is introduced at position 19 of exon 1 of TRBC1*01 or TRBC2*01.

FIGS. 44a and 44b respectively show the nucleotide sequences corresponding to the amino acid sequences in FIGS. 43a and 43b.

FIG. 45 shows an elution curve of gel filtration column after refolding the TCR α and β chains as shown in FIGS. 43a and 43b.

FIG. 46 shows the SEC spectrum of the TCR α and β chains as shown in FIGS. 43a and 43b after refolding and protein purification.

FIG. 47 shows a DSC thermogram of the TCR α and β chains as shown in FIGS. 43a and 43b after refolding and protein purification.

FIG. 48 shows binding curves of MGA3TCR molecules at different concentrations with its corresponding antigen after refolding the TCR α and β chains as shown in FIGS. 43a and 43b and protein purification.

FIGS. 49a and 49b respectively show the extracellular α chain amino acid sequence of LC13TCR in which a cysteine is introduced at position 10 of TRAC*01 exon 1, and the extracellular β chain amino acid sequence of LC13TCR in which a cysteine is introduced at position 20 of exon 1 of TRBC1*01 or TRBC2*01.

FIGS. 50a and 50b respectively show the nucleotide sequences corresponding to the amino acid sequences in FIGS. 49a and 49b.

FIG. 51 shows an elution curve of gel filtration column after refolding the TCR α and β chains as shown in FIGS. 49a and 49b.

FIG. 52 shows the SEC spectrum of the TCR α and β chains as shown in FIGS. 49a and 49b after refolding and protein purification.

FIG. 53 shows a DSC thermogram of the TCR α and β chains as shown in FIGS. 49a and 49b after refolding and protein purification.

FIG. 54 shows binding curves of LC13TCR molecules at different concentrations with its corresponding antigen after refolding the TCR α and β chains as shown in FIGS. 49a and 49b and protein purification.

FIGS. 55a and 55b respectively show the extracellular α chain amino acid sequence of 1G4TCR in which a cysteine is introduced at position 10 of TRAC*01 exon 1, and the extracellular β chain amino acid sequence of 1G4TCR in which a cysteine is introduced at position 20 of exon 1 of TRBC1*01 or TRBC2*01.

FIGS. 56a and 56b respectively show the nucleotide sequences corresponding to the amino acid sequences in FIGS. 55a and 55b.

FIG. 57 shows an elution curve of gel filtration column after refolding the TCR α and β chains as shown in FIGS. 55a and 55b.

FIG. 58 shows the SEC spectrum of the TCR α and β chains as shown in FIGS. 55a and 55b after refolding and protein purification.

FIG. 59 shows a DSC thermogram of the TCR α and β chains as shown in FIGS. 55a and 55b after refolding and protein purification.

FIG. 60 shows binding curves of 1G4TCR molecules at different concentrations with its corresponding antigen after refolding the TCR α and β chains as shown in FIGS. 55a and 55b and protein purification.

FIGS. 61a and 61b respectively show the extracellular α chain amino acid sequence of JM22TCR in which a cysteine is introduced at position 10 of TRAC*01 exon 1, and the extracellular β chain amino acid sequence of JM22TCR in which a cysteine is introduced at position 20 of exon 1 of TRBC1*01 or TRBC2*01.

FIGS. 62a and 62b respectively show the nucleotide sequences corresponding to the amino acid sequences in FIGS. 61a and 61b.

FIG. 63 shows an elution curve of gel filtration column after refolding the TCR α and β chains as shown in FIGS. 61a and 61b.

FIG. 64 shows the SEC spectrum of the TCR α and β chains as shown in FIGS. 61a and 61b after refolding and protein purification.

FIG. 65 shows a DSC thermogram of the TCR α and β chains as shown in FIGS. 61a and 61b after refolding and protein purification.

FIG. 66 shows binding curves of JM22TCR molecules at different concentrations with its corresponding antigen after refolding the TCR α and β chains as shown in FIGS. 61a and 61b and protein purification.

FIGS. 67a and 67b respectively show the extracellular α chain amino acid sequence of MGA3TCR in which a cysteine is introduced at position 10 of TRAC*01 exon 1, and the extracellular β chain amino acid sequence of MGA3TCR in which a cysteine is introduced at position 20 of exon 1 of TRBC1*01 or TRBC2*01.

FIGS. 68a and 68b respectively show the nucleotide sequences corresponding to the amino acid sequences in FIGS. 67a and 67b.

FIG. 69 shows an elution curve of gel filtration column after refolding the TCR α and β chains as shown in FIGS. 67a and 67b.

FIG. 70 shows the SEC spectrum of the TCR α and β chains as shown in FIGS. 67a and 67b after refolding and protein purification.

FIG. 71 shows a DSC thermogram of the TCR α and β chains as shown in FIGS. 67a and 67b after refolding and protein purification.

FIG. 72 shows binding curves of MGA3TCR molecules at different concentrations with its corresponding antigen after refolding the TCR α and β chains as shown in FIGS. 67a and 67b and protein purification.

DETAILED DESCRIPTION OF INVENTION

Figure 73:
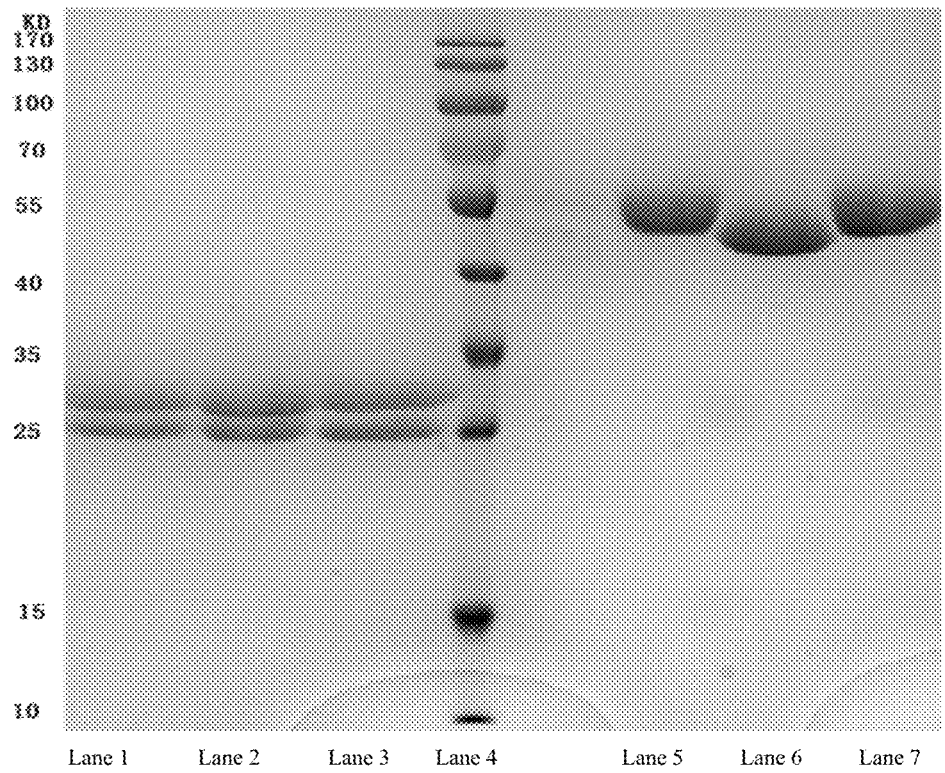
FIG. 73 shows reducing and non-reducing gel electrophoresis of LC13TCR molecules with an introduced artificial interchain disulfide bond, wherein Lane 4 is molecular weight marker.

Through extensive and intensive researches, the inventors have unexpectedly developed a highly stable soluble T cell receptor with a Tm value greater than 45° C. In particular, the inventors have mutated many different sites in the α and β chains of TCR into cysteine to introduce an artificial interchain disulfide bond. A class of highly stable soluble TCRs have been obtained after numerous and extensive screening. The specific site in the α and β chain constant domains of the TCR of the present invention is mutated into cysteine to form a new interchain disulfide bond. The TCR containing such new interchain disulfide bond has high stability with a Tm value greater than 45° C., can be well renatured, refolded and purified, has a high yield after refolding and can specifically bind with its original ligands. The present invention also provides the use and preparation of said TCRs.

T Cell Receptor (TCR)

The native TCR consists of two polypeptide chains, in the form of αβ or γδ, respectively. Each polypeptide has a constant domain close to membrane and a variable domain away from membrane. Each of the constant domain and variable domain contains an internal chain disulfide bond.

The extracellular constant domain of TCR has a region close to membrane and an immunoglobulin region. There are a group of disulfide bonds between the two chains of the near membrane region of native TCR, which are referred to as "natural interchain disulfide bond". In the present invention, an interchain covalent disulfide bond, which is artificially introduced at a position different from the position of the natural interchain disulfide bond, is referred to as "artificial interchain disulfide bond". In the present invention, the terms "polypeptides of the present invention", "TCR of the present invention" and "T cell receptors of the present invention" are interchangeable and refer to a TCR containing an artificial interchain disulfide bond of the present invention.

The TCRs of the invention are named as in the International Immunogenetics Information System (IMGT). In this system, "TRAC*01" represents an α-chain constant domain of TCR, wherein "TR" represents a T cell receptor gene, "A" represents an α-chain gene, C represents a constant region, "01" means allele 1. Likewise, "TRBC1*01" or "TRBC2*01" represents a β chain constant domain. There are two possible constant region genes "C1" and "C2" in the β chain. The domain translated and encoded by each allele may consist of genetic codes from several exons. Thus, the sequences of TCR constant domains are well known to the skilled in the art and available in IMGT, for example, in the public database of IMGT. The 53rd position in the amino acid sequence of TRAC*01 of IMGT is R, which is expressed as 53R in exon 1 of TRAC*01. The other positions are expressed in the same way. The TCR α chain has a unique constant domain TRAC*01. The two constant domains of β chain are only slightly different. TRBC1*01 has 4N, 5K and 37 F in its exon, while TRBC2*01 has 4K, 5N and 37Y in its exon. Therefore, when the constant region of β chain in TCR molecule is TRBC1*01 or TRBC2*01, there is substantially no difference. In summary, because different TCRs have a constant amino acid sequence in the constant region, the spatial structure of constant region in different TCRs is considered to be the same. The term "stability" refers to any aspect of protein stability. Compared with the original wild-type protein, the high-stability protein screened out has one or more of the following characteristics: more resistant to unfolding, more resistant to inappropriate or undesirable folding, stronger renaturability, stronger expression ability, higher protein renaturation yield, and increased thermal stability. Preferably, it refers to higher protein renaturation yield and/or increased thermal stability.

A non-cysteine residue on each TCR chain can be mutated into Cys, thereby forming an artificial interchain disulfide bond. The disulfide bond is preferably located at a constant region of each TCR chain.

In a preferred embodiment of the invention, the site for introducing a cysteine residue so as to form an artificial interchain disulfide bond comprises:

53R in Exon 1 of TRAC*01, and 54S in Exon 1 of TRBC1*01 or TRBC2*01;

89P in Exon 1 of TRAC*01, and 9A in Exon 1 of TRBC1*01 or TRBC2*01; or 10Y in Exon 1 of TRAC*01, and 20E in Exon 1 of TRBC1*01 or TRBC2*01.

In a preferred embodiment of the invention, the TCR of the invention may comprise a complete constant domain except the transmembrane domain (i.e., an extracellular and cytoplasmic domain). In this case, one or more cysteine residues forming a disulfide bond between the natural TCR chains are preferably mutated into other amino acid residues that do not participate in formation of disulfide bond.

In another preferred embodiment of the invention, the TCR of the invention may comprise a partial constant domain other than the transmembrane domain. In this case, one or more cysteine residues forming a disulfide bond between the natural TCR chains are mutated into other amino acid residues that do not participate in formation of disulfide bond. Alternatively, one or more such residues are deleted.

In a preferred embodiment of the invention, the TCR does not have a natural interchain disulfide bond. It can be achieved by mutating cysteine which forms a natural interchain disulfide bond into another amino acids or by truncating the corresponding chain so as not to exclude a cysteine residue forming a natural interchain disulfide bond, thereby deleting a natural interchain disulfide bond.

In a preferred embodiment of the invention, the highly stable TCR of the invention comprises a constant region of natural TCR α and β chains with a truncated C-terminal. Preferably, it is truncated at a distance of 1, 2, 3, 4, 5, 6, 7, 8, 9 or 10 or more amino acids from the cysteine residue that forms a natural interchain disulfide bond so as to remove a cysteine residue forming a natural interchain disulfide bond. The resultant TCR does not contain any natural interchain disulfide bond. It should be pointed out, however, that the TCR of the invention may also contain a natural interchain disulfide bond. It should be noted that, in some cases, only one TCR chain has a cysteine that forms a natural interchain disulfide bond, which is used to link the TCR molecule having an artificial interchain disulfide bond with some other molecular. When the β chain of TCR contains a free unpaired cysteine residue, it is preferred in the invention that said cysteine is mutated into another amino acid, such as Ser or Ala. The chains of the TCR of the invention may also contain an internal disulfide bond.

It is to be understood that the constant domain of TCR is not directly involved in the binding of TCR to pMHC and that the truncation of a certain number of amino acid residues at the C-terminal will not substantially affect the function of TCR. Therefore, the chains of the TCR of the invention may be further shortened. The binding affinity (inversely proportional to the dissociation equilibrium constant KD) of the TCR of invention with its corresponding antigen can be determined by any suitable method. It should be understood that the doubling of affinity of TCR will halve KD value. In a preferred embodiment of the invention, the dissociation equilibrium constant KD of TCR with its corresponding pMHC is measured by forteBIO Oke, as described in Example 4 of the invention.

Not every amino acid residue in the TCR chain is critical to its antigen specificity and functionality. Therefore, an appropriate amount of mutation can be introduced in the TCR chain of the present invention without affecting its antigen specificity and functionality. Other mutations include, but are not limited to, deletion, insertion, and substitution of 1 to 6 amino acids (usually 1 to 5, preferably 1 to 3, more preferably 1 to 2, preferably 1); adding one or more (usually 5 or less, preferably 3 or less, and more preferably 2 or less) amino acids at the C-terminal and/or N-terminal. For example, in the art, substitution with a functionally similar amino acid usually does not alter the function of protein. The addition of one or more amino acids at the C-terminal and/or N-terminal usually does not alter the structure and function of protein.

In the present invention, suitable sites in TCR chain are identified which can be mutated into Cys to form an artificial interchain disulfide bond for stabilization of TCR. The TCR of the invention may contain not only human TCRs, but also the highly stable TCRs of other species. The skilled in the art can obtain those TCRs based on the suitable sites provided in the present invention. For example, one skilled in the art can determine the residues to be mutated (the bolded and underlined residue is a residue for mutation into Cys) by finding the following motif in the corresponding TCR chain:

```
α chain constant region, 10Y:
                                   (SEQ ID NO: 68)
IQNPDPAVYQLRDSKSSDKS α chain constant region, 53R:
                                   (SEQ ID NO: 69)
ITDKTVLDMRSMDFKSNSAV α chain constant region, 89P:
                                   (SEQ ID NO: 70)
SIIPEDTFFCSPESSSAAAL β chain constant region, 20E:
                                   (SEQ ID NO: 71)
EVAVFEPSEAEISHTQKATL β chain constant region, 54S:
                                   (SEQ ID NO: 72)
WWVNGKEVHSGVSTDPQPLK
and β chain constant region, 19A:
                                   (SEQ ID NO: 73)
EVAVFEPSEAEISHTIQKATL.
```

Although TCR chains from other species may have a region which is not 100% same as the above motifs, the skilled in the art can identify the equivalent portion in the corresponding TCR according to the above motif so as to obtain a cysteine residue to be mutated. For example, ClustalW available the European Institute of Bioinformatics can be used to compare the TCR chain from other species with the above motifs to obtain the corresponding site.

The present invention comprises a stable human αβTCR linked with an artificial interchain disulfide bond, as well as other mammal αβTCR linked with an artificial interchain disulfide bond. Such mammals include, but are not limited to, goat, sheep, pig, mouse and rat. For example, according to the present invention, it is possible to identify the following sites (in bold and underlined letters) for introducing Cys residue in mouse to form an artificial interchain disulfide bond:

```
mouse homolog of human α chain containing 10Y:
                                   (SEQ ID NO: 74)
IQNPEPAVYQLKDPRSQDSTLCLF mouse homolog of human α chain containing 53R:
                                   (SEQ ID NO: 75)
GTFITDKTVLDMKAMDSKSNGA mouse homolog of human α chain containing 89P:
                                   (SEQ ID NO: 76)
QDIFKETNATYPSS mouse homolog of human β chain containing 20E:
                                   (SEQ ID NO: 77)
FPPEVAVFEPSEAEISHTQKATLVCLAT mouse homolog of human β chain containing 54S:
                                   (SEQ ID NO: 78)
LSWWVNGKEVHSGVSTDPQAYKESN mouse homolog of human β chain containing 19A:
                                   (SEQ ID NO: 79)
FPPEVAVFEPSEAEISHTQKATLVCLAT.
```

It should be understood, amino acid names used herein are internationally accepted single alphabetical identity and its corresponding abbreviations of amino acid name with three English letters. They are Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y), and Val (V).

The present invention further includes the active fragments, derivatives and analogs of the polypeptide of the present invention. As used herein, the terms "fragments". "derivatives" and "analogs" refer to the polypeptides that can bind with a ligand molecule. The polypeptide fragments, derivatives or analogs of the present invention may be (i) a polypeptide with one or more conservative or non-conservative amino acid residues (preferably the conservative amino acid residues) being substituted, or (ii) a polypeptide having substituted group(s) in one or more amino acid residues, or (iii) a polypeptide formed by fusion of TCR of the present invention with another compound (such as the compound that prolongs the half life of the polypeptide, such as polyethylene glycol), or (iv) a polypeptide with additional amino acid sequence fused to said polypeptide sequence, such as fusion proteins formed by fusion with leader sequence, secretion sequence or tag sequence, such as 6His. According to the teaching of present invention, these fragments, derivatives and analogs are within the scope commonly known by the skilled person.

A class of preferred active derivatives are the polypeptides formed by replacing at most 5, preferably at most 3, more preferably at most 2, and most preferably 1 amino acid(s) of the amino acid sequence of the polypeptide of the present invention with an amino acid having similar or analogous property. These conservative variant polypeptides are preferably formed by carrying out the amino acid replacement according to Table A.

TABLE A

| Initial residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides the analogues of TCR of the present invention. These analogues differ from TCR of the present invention in amino acid sequence or modifications that do not affect the sequence, or by both. Also included are analogues which include residues other than those naturally occurring L-amino acids (e.g., D-amino acids) or non-naturally occurring or synthetic amino acids (e.g., beta- or gamma-amino acids). It is understood that the polypeptides of the present invention are not limited to the representative polypeptides listed hereinabove.

Modifications (which do not normally alter the primary sequence) include in vivo or in vitro chemical derivation of polypeptides, e.g., acetylation, or carboxylation. Glycosylation is also included in modification, e.g., the polypeptides produced by glycosylation modification during its synthesis and processing or in the further processing steps. These modifications can be achieved by exposing the polypeptide to enzymes for glycosylation (e.g., mammalian glycosylating or deglycosylating enzymes). Also included are sequences that have phosphorylated amino acid residues, e.g., phosphotyrosine, phosphoserine, phosphothronine, as well as sequences that have been modified to improve their resistance to proteolytic degradation or to optimize solubility properties.

The polypeptides of the present invention can be used in a form of pharmaceutically or physiologically acceptable salt derived from acid or base. Such salts include, but are not limited to, the salts formed with the following acids: hydrochloric acid, hydrobromic acid, sulfuric acid, citric acid, tartaric acid, phosphoric acid, lactic acid, pyruvic acid, acetic acid, succinic acid, oxalic acid, fumaric acid, maleic acid, oxaloacetic acid, methanesulfonic acid, ethyl-sulfonic acid, benzene sulfonic acid, or isethionic acid. Also included are salts formed with alkali metals or alkaline earth metals (such as sodium, potassium, calcium or magnesium), and esters, carbamate or other conventional "prodrug" forms.

Polypeptides of the present invention can be provided in form of multivalent complexes.

Multivalent TCR complex of the present invention comprises two, three, four or more TCR molecules linked with another molecule.

The present invention also relates to a polynucleotide encoding the TCR of the invention.

The full-length nucleotide sequence of the present invention, or a fragment thereof can usually be obtained by but not limited to the PCR amplification, recombination or synthetic methods. At present, the DNA sequences encoding polypeptides of the present invention (or fragments thereof, or derivatives thereof) can be obtained completely by chemical synthesis.

Then the DNA sequences can be introduced into various existing DNA molecules (for example vectors) and cells known in the art.

The present invention also includes a vector containing the polynucleotide of the present invention, and a host cell genetically engineered by using the vector or the coding sequence of the present invention.

Encoding Sequence

The present invention further relates to polynucleotides encoding the TCR of the present invention.

The polynucleotides of the present invention can be in a form of DNA or RNA. DNA may be the coding strand or non-coding strand. For example, the coding sequence encoding the mature polypeptide can be identical to the coding sequence indicated in any of SEQ ID NO: 1, 3, 5, 7, 9, 11, 13, 15, 17, 19, 21, 23, 25, 27, 29, 31, 33, 35, 37, 39, 41, 43, 45, 47, or can be a degenerate variant thereof. As used herein, "degenerate variant" refers to a nucleic acid sequence which encodes the protein having any of the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, but is different from the above corresponding coding sequence.

The full-length nucleotide sequence of the present invention, or a fragment thereof can usually be obtained by but not limited to the PCR amplification, recombination or synthetic methods. At present, the DNA sequences encoding polypeptides of the present invention (or fragments thereof, or derivatives thereof) can be obtained completely by chemical synthesis.

Then the DNA sequences can be introduced into various existing DNA molecules (for example vectors) and cells known in the art.

The present invention also includes a vector containing the polynucleotide of the present invention, and a host cell engineered by the vector or the coding sequence of the present invention.

Moreover, the present invention further comprises polyclonal antibodies or monoclonal antibodies specific to TCR polypeptide of the present invention, especially the monoclonal antibodies.

Preparation Method

The introduction of a Cys residue for forming a novel interchain disulfide bond can be carried out by using any suitable methods including, but not limited to, those based on polymerase chain reaction (PCR), restriction enzyme based cloning or linkage independent cloning (LIC). These methods are detailed in many of the standard molecular biology texts. For further details regarding polymerase chain reaction (PCR) mutagenesis and restriction enzyme based cloning, see Sambrook & Russell, (2001) Molecular Cloning—A laboratory Manual ($3^{rd}$ Ed) CSHL press. More information on the procedure of LIC can be found in Rashtchian, (1995) *Curr Opin Biotechnol* 6 (1): 30-6.

The polypeptide of the present invention can be a recombinant or synthetic polypeptide. The polypeptide of the present invention can be a chemically synthesized or recombinant polypeptide. Accordingly, the polypeptide of the present invention can be artificially synthesized via a conventional method, or can be produced via a recombinant method.

With the conventional recombinant DNA technique, the polynucleotide of the present invention can be used to express or produce recombinant polypeptides of the present invention. Generally, the method comprises the following steps:

(1) Transforming or transfecting a suitable host cell with a polynucleotide or variant thereof encoding TCR polypeptide of the present invention or a recombinant expression vector containing said polynucleotide:

(2) Culturing the host cell in a suitable culture medium;

(3) Isolating and purifying the TCR polypeptide of the present invention from the culture medium or the cell.

Preferably, the soluble, highly stable TCR of the invention can be obtained by expressing it in bacteria such as in *E. coli* as an inclusion body and performing in vitro refolding.

Pharmaceutical Composition and Methods of Administration

The TCRs of the present invention and T cells transfected with TCRs of the present invention may be provided in a pharmaceutical composition together with a pharmaceutically acceptable carrier. The TCRs, multivalent TCR complexes and cells of the present invention will usually be supplied as part of sterile pharmaceutical composition which will normally comprises a pharmaceutically acceptable carrier. The pharmaceutical composition can be in any appropriate forms (depending upon the desired method of administering to a patient). It can be provided in unit dosage form, will generally be provided in a sealed container, and can be provided as part of a kit. The kit (although not necessarily) normally includes instructions for use. It may include a plurality of said unit dosage forms.

In addition, the polypeptides of the present invention may be used alone, or associating or coupling with other therapeutic agents (e.g., those formulated in the same pharmaceutical composition).

Therapeutic agents that can be associated with or coupled with the TCRs of the present invention include, but are not limited to: 1. Radioactive nuclide (Koppe, et al, 2005, *Cancer metastasis reviews* 24, 539); 2. Biological toxin (Chaudhary et al, 1989, Nature, 339, 394; Epel et al, 2002, *Cancer immunology and immunotherapy* 51, 565); 3. Cytokine (Gillies, et al, 1992, *PNAS*, 89, 1428; Card, et al, 2004, *Cancer immunology and immunotherapy* 53, 345; Halin, et al, 2003, *Cancer research* 63, 3202); 4. Antibody Fc fragment (Mosquera et al, 2005, *The journal of immunology* 174, 4381); 5. Antibody scFv (Zhu, et al, 1995, *International journal of cancer* 62, 319); 6. Gold nano-particle/nano-rod (Lapotko, et al, 2005, *Cancer letters* 239, 36; Huang, et al, 2006, *Journal of the American chemical society* 128, 2115); 7. Virus particles (Peng, et al, 2004, *Gene therapy*, 11, 1234); 8. Liposome (Mamot, et al, 2005, *Cancer research* 65, 11631); 9. Magnetic nano-particles; 10. Prodrug activating enzymes (such as DT-diaphorase (DTD) or Biphenyl hydrolase-like protein (BPHL)); 11. Chemotherapeutic agent (e.g., cisplatin), and the like.

The antibody or fragment thereof bound to the TCR of the invention comprises an anti-T cell or an NK-cell determining antibody such as an anti-CD3 or anti-CD28 or anti-CD16 antibody. The binding of antibody or fragment thereof with TCR is capable of directing effector cells to better target a cell of interest.

The pharmaceutical composition can further comprise a pharmaceutically acceptable carrier. The term "pharmaceutically acceptable carrier" refers to a carrier for using in administering the therapeutic agents. The term refers to such medical carriers that they themselves do not induce antibody deleterious to the subject having been administered the composition, and they do not have excessive toxicity after administration. These carriers are well known by the skilled person in the art. The detailed discussion about the pharmaceutically acceptable excipient can be found in Remington's Pharmaceutical Sciences (Mack Pub. Co., N.J., 1991). Such carriers include, but are not limited to, saline, buffer solution, glucose, water, glycerin, ethanol, adjuvant or the combination thereof.

The pharmaceutically acceptable carrier in the therapeutic composition can comprise liquid, such as water, saline, glycerin, and ethanol. Further, these carriers can contain auxiliary substance(s), such as wetting agent or emulsifying agent, pH buffering substance, etc.

Typically, the therapeutic composition can be formulated into an injectable formulation, such as a liquid solution or suspension; or it may be in a solid form that is suitable to be formulated into a solution or suspension or liquid carrier before injection.

Once formulated, the composition of the present invention can be administered via conventional routes which include, but are not limited to, administering intra-ocularly, intramuscularly, intravenously, subcutaneously, intracutaneously or topically. The subject to be prevented or treated may be an animal, especially a human.

When the pharmaceutical composition of the present invention is used in the actual treatment, the dosage form of the pharmaceutical composition can be varied according to the uses. Preferably, as an example, the dosage form may include injection, oral formulation, etc.

The pharmaceutical composition can be formulated by mixing, diluting or dissolving according to the conventional methods. And, occasionally, suitable medical additives, such as excipients, disintegrating agents, adhesives, lubricants, diluting agents, buffering agents, isotonicities, preservatives, wetting agents, emulsifying agents, dispersing agents, stabilizing agents, and solubility promoters, may be added. Formulation can be carried out in a conventional manner according to the dosage form.

The pharmaceutical composition of the present invention can further be administered in a form of sustained release formulation. For example, the peptide of the present invention can be incorporated into the pill or microcapsule in which a sustained release polymer is used as carrier, and then the pill or microcapsule is implanted into the tissue to be treated by operation. Examples of the slow release polymer include ethylene-ethylene acetate copolymer, polyhydroxymethylacrylate, polyacrylamide, polyvinylpyrrolidone, methyl cellulose, polymer of lactic acid, lactic acid-glycolic acid copolymer, etc. Preferable examples include the biodegradable polymers, such as polymer of lactic acid, and lactic acid-glycolic acid copolymer.

When the pharmaceutical composition of the present invention is used in the actual treatment, the dose of the peptide the present invention or a pharmaceutically acceptable salt thereof, as an active ingredient, can be suitably determined according to the body weight, age, sex, symptom of each patient.

Use of TCR of Invention

The TCR of the present invention can be used as a drug or a diagnostic agent. The features which are suitable for use as a drug or a diagnostic agent can be obtained by modifications or other improvements. Such drugs or diagnostic agents may be used for treatment or diagnosis of various diseases, including but not limited to cancer (such as renal cancer, ovarian cancer, head and neck cancer, testicular cancer, lung cancer, gastric cancer, cervical cancer, bladder cancer, prostatic carcinomas or melanomas), autoimmune disease, viral infection disease, graft rejection and graft-versus-host disease.

Drug localization or targeted drug delivery can be realized based on specificity of the TCR of invention, thereby enhancing therapeutic or diagnostic effects of various diseases.

For cancer, the localization in the vicinity of tumors or metastasis can enhance the effect of toxins or immunostimulants. In autoimmune diseases, immunoreaction to normal cells or tissues can be inhibited specifically, or immunosuppressive drugs can be released slowly to get more local effect over a longer time-span while minimally affecting the overall immuno-capacity of the subject. In the prevention of transplant rejection, the effect of immunosuppression can be optimized in the same way. For viral diseases for which medicines exist, for example HIV, SIV, EBV, CMV, HCV, HBV, it is beneficial that the medicine is released or plays activation function in vicinity of infected cells.

TCRs of the invention can be used to modulate T cell activation by binding to specific pMHC and thereby inhibiting T cell activation. This approach may apply to autoimmune diseases involving T cell-mediated inflammation and/or tissue damage, for example type I diabetes.

TCRs of the invention can also be used for delivering cytotoxic agents to tumor cells, or can be transformed into T cells, thus rendering them a capability of damaging tumor cells presenting HLA complexes so that they can be administrated to a patient in a treatment process termed adoptive immunotherapy.

TCRs of invention can also be used as a therapeutic agent. TCRs of invention can be labeled with a detectable label, for example a label which is suitable for diagnostic purpose, for detecting binding of a MHC-peptide to a TCR of the invention which is specific for the MHC-peptide. A fluorescently-labeled multimeric TCR is suitable for use in FACS analysis to detect antigen presenting cells carrying a peptide to which the TCR is specific.

INDUSTRIAL APPLICABILITY

The high-stable TCR of the present invention is useful not only in the study of the interaction between TCR and pMHC (peptide-major histocompatibility complex) but also in diagnosis and treatment of diseases.

The main advantages of the present invention comprise:
(1) The TCR of the invention has a high stability, can be well renatured, refolded, and purified and can specifically bind to its original ligand.
(2) The TCR of the invention has a high Tm value with a Tm value greater than 45° C.
(3) The TCR of the invention has a high protein yield after refolding, is easy for production in large scale, and can reduce production cost.

The present invention will be further illustrated below with reference to the specific examples. It will be appreciated that the fact that a highly stable TCR molecule is obtained by introducing an interchain disulfide bond of the invention into a TCR constant region is sufficient to demonstrate the function of the artificial chain of the invention because the constant region amino acid sequence and spatial structure of the different TCRs are the same. By using several different molecules as exemplary TCRs, the following examples further illustrate the introduction of the interchain disulfide bond of the invention into TCR molecules can produce a soluble TCR having a high refolding effect, high yield after refolding and high stability. It should be understood that these examples are only to illustrate the invention, not to limit the scope of the invention. The experimental methods with no specific conditions described in the following examples are generally performed under the conventional conditions (e.g., the conditions described by Sambrook and Russell et al., Molecular Cloning-A Laboratory Manual ($3^{rd}$ Ed) CSHL Press), or according to the manufacture's instructions. Unless indicated otherwise, parts and percentage are calculated by weight. The experimental materials used in the examples of the invention are commercially available, unless indicated otherwise.

Example 1 Primers Design and PCR Mutations of LC13 Molecule for Introducing an Artificial Interchain Disulfide Bond at Position 53 of TRAC*01 Exon 1 and Position 54 of TRBC1*01 or TRBC2*01 Exon 1

The arginine at position 53 of TRAC*01 exon 1 of TCR molecule LC13 against antigen short peptide HLA-B4405: EEYLKAWTF (SEQ ID NO.: 49) was mutated into cysteine and the serine at position 54 of TRBC1*01 or TRBC2*01 exon 1 was mutated into cysteine, thereby forming an artificial interchain disulfide bond.

When the arginine at position 53 of TRAC*01 exon 1 of above TCR was mutated into cysteine, the primers were designed as follows:

```
5'-3'
                                        (SEQ ID NO.: 50)
GATAAATGCGTGCTGGATATGTGCAGCATGGATTTCAAAAG (SEQ ID NO.: 51)
CTTTTGAAATCCATGCTGCACATATCCAGCACGCATTTATC
```

When the serine at position 54 of TRBC1*01 or TRBC2*01 exon 1 of above TCR was mutated into cysteine, the primers were designed as follows:

```
5'-3'
                                     (SEQ ID NO.: 52)
GGCAAAGAAGTGCATTGCGGTGTTTGTACCGATC (SEQ ID NO.: 53)
GATCGGTACAAACACCGCAATGCACTTCTTTGCC
```

The steps of PCR were as follows:

The expression plasmids containing the LC13 TCR α and β chain genes were mutated with the above α and β chain primers, respectively. In each PCR site-directed mutation reaction, 10-30 ng of plasmid DNA was mixed with 5 μL of 10×KOD plus buffer, 5 μL of 2.5 mM dNTP Mix, 3 μL of 2 mM MgSO$_4$, 1 unit of KOD plus polymerase (Toyobo Shanghai BioScience Co., Ltd.), 1 μL of 10 μM upstream and downstream primers, and finally H$_2$O was added to 50 μL. After mixing, the reaction was carried out in a Bio-Rad PCR instrument. After 94° C. 2 min initial denaturation, 18 cycles of amplification (94° C. 15 sec of denaturation, 55° C. 30 sec of annealing and 68° C. 6 min of extension) were performed. And 10 units of Dpn I restriction enzyme (New England Biolabs) was used for digestion at 37° C. for 1 hour. 10 μL of digested product was transformed into competent E. coli DH5α bacteria and grown at 37° C. for 16 hours. Single clones were picked and cultured overnight in 5 mL LB+Kanamycin. Plasmid DNA was purified using the Zyppy plasmid kit (ZYMO RESEARCH) according to the manufacturer's instructions and sent to Invitrogen for sequencing and the correct mutation was used for downstream expression.

The α-chain and β-chain extracellular amino acid sequences of the mutated TCR molecule LC13 are shown in FIGS. 1a and 1b, respectively, and their corresponding nucleotide sequences are shown in FIGS. 2a and 2b, respectively. The introduced cysteine residues are bolded and underlined.

Example 2 TCR Expression, Refolding and Purification and Determination Results TCR Protein Expression The target gene carrying the template chain was digested with NcoI and NotI and ligated with pET28a (Novagen) vector digested with NcoI and NotI. The ligation product was transformed into E. coli DH5α (Tiangen), coated on kanamycin-containing LB plates, incubated overnight at 37° C., and the clones were picked for PCR and the positive recombinants were sequenced.

The expression plasmids containing TCR α and β chain were transformed into E. coli strain BL21 (DE3), coated on LB plates (kanamycin 50 μg/ml) and incubated overnight at 37° C. overnight. The next day, the cells were inoculated into 10 ml LB liquid medium (kanamycin 50 μg/ml) and cultured for 2-3 h and then seeded at 1: 100 in volume to 1 L LB medium (kanamycin 50 μg/ml), and cultured to OD600 at 0.5-0.8. And then the expression of the target protein was induced using IPTG at a final concentration of 1 mM. After 4 hours of induction, the cells were harvested by centrifugation at 6000 rpm for 10 min. The cells were washed once with PBS buffer and were dispensed. And the cells corresponding to 200 ml of bacterial culture were digested with 5 ml BugBuster Master Mix (Novagen) and the inclusion bodies were collected by centrifugation at 6000 g for 15 min. Four detergent washings were then performed to remove cell debris and membrane fractions. The inclusion bodies are then washed with a buffer such as PBS to remove the detergent and salt. Finally, the inclusion bodies were dissolved with 6M guanidine hydrochloride buffer solution. The inclusion body was determined for its concentration and dispensed at −80° C. for cryopreservation.

TCR Protein Refolding

The inclusion body was taken out from the −80° C. cryogenic refrigerator and dithiothreitol (DTT) was added to a final concentration of 10 mM and the inclusion body was incubated at 37° C. for 30 min to 1 hour to ensure that the disulfide bond was fully open. The inclusion body sample solution (15 mg α chain and 10 mg β chain) was then added dropwise into 200 ml of 4° C. pre-cooled refolding buffer (100 mM Tris pH 8.1, 400 mM L-arginine, 2 mM EDTA, 5 M urea, 6.5 mM cysteamine hydrochloride and 1.87 mM dihydrochloride) and slowly stirred at 4° C. for about 30 minutes. The refolding solution was dialyzed with 8 volumes of pre-cooled H$_2$O for 16-20 hours and then dialyzed twice with 8 volumes of 20 mM Tris pH 8.0 and dialyzed for 4 hours at 4° C. After dialysis, the sample was filtered and purified as follows.

The First Step of Purification of TCR Protein

The dialyzed refolded product (in 20 mM Tris pH 8.0) was eluted with a GE Hitrap Q anion exchange preparative column (GE Healthcare) using a gradient elution at 0-600 mM NaCl in an AKTA Purification Instrument (GE Healthcare). The components were analyzed by Coomassie brilliant blue staining SDS-PAGE and then combined.

The Second Step of Purification of TCR Protein

The purified pooled sample solution in the first step was concentrated for this step and Superdex 100 160/300 GL gel filtration pre-packed column (GE Healthcare) pre-equilibrated in PBS buffer was used to purify the protein. The elution curves of TCR molecule LC13 were shown in FIG. 3. The components with peak were analyzed by Coomassie bright blue-stained SDS-PAGE, and the reducing and non-reducing gel electrophoresis were shown in lane 2 and lane 6 of FIG. 73. According to the elution peak and the gel electrophoresis, it was found that the elution peak was a soluble TCR molecule linked by an artificial interchain disulfide bond. The molecule was stable in SDS gel and formed separate α and β chains after reduction.

Determination of TCR Protein by HPLC

The TCR protein was purified by two steps and the eluted fraction was tested for its purity by HPLC. The condition was: Agilent 1260, column Bio SEC-3 (300 A, φ7.8×300 mm) with mobile phase of 150 mM phosphate buffer, flow rate 0.5 mL/min, column temperature 25° C., UV detection wavelength 214 nm. The SEC (spatial exclusion chromatography) spectrum of the LC13 TCR molecule is shown in FIG. 4. The HPLC elution peaks of the TCR molecules containing the artificial interchain disulfide bonds of the present invention were single and symmetrical.

Calculation of Yield of TCR Protein after Refolding

The yield of TCR protein after refolding in the present invention is calculated as follows:

Protein refolding yield (%)=100*purified protein quantity (mg)/inclusion body quantity used in refolding (mg).

According to the above calculation, the protein refolding yield of the LC13 TCR having an artificial interchain disulfide bond formed between the position 53 of TRAC*01 exon 1 and the position 54 of TRBC1*01 or TRBC2*01 exon 1 was 43.30%. The yield was very high, indicating that the soluble TCR molecules with the artificial interchain disulfide bonds of the present invention were very stable.

Example 3 Stability Test of TCR Containing Artificial Interchain Disulfide Bonds The LC13 TCR protein (concentration 0.5 mg/ml) obtained in Example 2 was dialyzed into PBS and the thermostability of the TCR proteins was measured with differential scanning calorimeter (Nano DSC) of US TA company (Waters). Scanning range was 10-90° C., and heating rate was 1° C./min. Using dialysis liquid PBS as a control, the baseline was measured three times, and after the baseline was stable, the protein sample was examined. After collecting the data, the Tm value of the TCR was measured with the analysis software TA_DSC_NanoAnalyze and the DSC thermogram was obtained. The DSC thermogram of the LC13 TCR of the present invention containing the artificial interchain disulfide bond obtained by in vitro soluble expression was shown in FIG. 5 and its Tm value could reach 55.82° C. The thermogram could reflect that at room temperature, even at a temperature of 41-43° C., the TCR molecules containing the artificial interchain disulfide bond of the present invention could maintain proper folding and maintain proper activity, indicating that their stability was very high.

Example 4 Binding Characterization and Specificity Detection

The binding activity of the TCR protein to its corresponding antigen pMHC complex was examined using the forteBIO Oke real time analysis system.

A biotinylated pMHC complex of about 2 nm was immobilized on the surface of the SA sensor, and 0.05 mM biotin was flowed through the chip at a flow rate of 10 μL/min for 120 s to block the remaining binding sites of streptavidin. The affinity of the TCR protein was determined by kinetic analysis using PBST buffer (PBS+0.005% Tween 20, pH 7.4) diluted to 5 different concentrations (typically 64, 32, 16, 8, 4, 0 uM). And the affinity for the corresponding pMHC was determined. The kinetic parameters were calculated using the evaluation software with a 1:1 model fit.

The preparation of the above pMHC complex was as follows:

a. Purification 100 ml of *E. coli* culture induced for heavy or light chains expression was collected and centrifuged at 8000 g for 10 min at 4° C. and the cells were washed once with 10 ml PBS and then the cells were resuspended vigorously with 5 ml BugBuster Master Mix Extraction Reagents (Merck) and incubated at room temperature for 20 min. After centrifugation at 4° C. 6000 g for 15 min, the supernatant was discarded and the inclusion bodies were collected.

The inclusion bodies were resuspended in 5 ml BugBuster Master Mix and incubated for 5 min at room temperature. 30 ml of BugBuster (10-fold dilution) was added and mixed, centrifuged at 4° C. 6000 g for 15 min. The supernatant was discarded and 30 ml BugBuster (10-fold dilution) was added to resuspend the inclusion body and mixed, and centrifuged at 4° C. 6000 g for 15 min, repeat twice. 30 ml 20 mM Tris-HCl pH 8.0 was added to resuspend the inclusion body, mixed and centrifuged at 4° C. 6000 g for 15 min. Finally, 20 mM Tris-HCl 8M urea was used to dissolve inclusion bodies. SDS-PAGE was used to detect the purity of inclusion body. A BCA kit was used to detect the concentration.

b. Refolding

The desired peptide was synthesized (Peking Parkson Gene Technology Co., Ltd.) and was dissolved in DMSO to a concentration of 20 mg/ml. Light chain and heavy chain inclusion bodies were dissolved with 8 M urea, 20 mM Tris pH 8.0, and 10 mM DTT. Before refolding, 3 M guanidine hydrochloride, 10 mM sodium acetate, and 10 mM EDTA were added for further denaturation. The short peptide at 25 mg/L (final concentration) was added to the refolding buffer (0.4 M L-arginine, 100 mM Tris pH 8.3, 2 mM EDTA, 0.5 mM oxidized glutathione, 5 mM reduced glutathione, 0.2 mM PMSF, and cooled to 4° C.), followed by the addition of 20 mg/L light chain and 90 mg/L heavy chain (final concentration, heavy chain was added three times, 8 h every time) refolding at 4° C. for at least 3 days to complete, and SDS-PAGE was used to detect the success of refolding.

c. Purification after Refolding

The refolding buffer was replaced with dialysis using 10 volumes of 20 mM Tris pH 8.0 and the refolding buffer was replaced at least twice to sufficiently reduce the ionic strength of the solution. After dialysis, the protein solution was filtered through a 0.45 um cellulose acetate filter and then loaded onto HiTrap Q HP (GE Universal) anion exchange column (5 ml bed volume). The protein was eluted with a linear gradient of 0-400 mM NaCl prepared at 20 mM Tris pH 8.0 using a Akta Purification Instrument (GE General Electric Co., Ltd.), and pMHC was eluted at about 250 mM NaCl and the peak components were collected and the purity was analyzed by SDS-PAGE.

d. Biotinylated

The purified pMHC molecule was concentrated by Millipore ultrafiltration tubes while the buffer was replaced with 20 mM Tris pH 8.0 followed by adding biotinylated reagent 0.05 M Bicine pH 8.3, 10 mM ATP, 10 mM MgOAc, 50 μM D-Biotin, 100 μg/ml BirA enzyme (GST-BirA). The mixture was incubated at room temperature overnight. SDS-PAGE was used to determine whether biotinylation was complete.

e. Purification of Biotinylated Complexes

The biotin labeled pMHC molecule was concentrated to 1 ml with a Millipore ultrafiltration tube, and the biotinylated pMHC was purified by gel filtration chromatography using an Akta Purification Instrument (GE General Electric Co., Ltd.). HiPrep™ 16/60 S200 HR column (GE General Electric) was pre-equilibrated with filtered PBS. 1 ml of concentrated biotinylated pMHC molecule was loaded and then eluted with PBS at a flow rate of 1 ml/min. The biotinylated pMHC molecule appeared as a single peak at about 55 ml. The protein-containing fractions were pooled, and concentrated with Millipore ultrafiltration tubes. The protein concentration was measured by BCA method (Thermo), and the biotinylated pMHC molecules were stored at −80° C. by adding a protease inhibitor cocktail (Roche).

The binding curves of the different concentrations of LC13 molecules to their corresponding antigens were shown in FIG. 6 and the KD values were 10.5 μM. It can be seen from these binding curves that the decrease in concentration did not affect the binding of the TCR molecules of the invention to its corresponding antigens. The TCR molecules at a low concentration exhibited the same binding activity as that at a high concentration. And it also demonstrated from another aspect that the TCR having the artificial interchain disulfide bond of the present invention was relatively stable.

Specific Detection of TCR Protein

The forteBIO Oke real-time analysis system was used to detect the specificity of the TCR protein for its corresponding antigen pMHC complex. Six different biotinylated antigens (concentrations of 0.5 μM) were loaded onto the surface of six SA sensors respectively, and then interacted with each of the TCR proteins to be tested (concentrations of 2-20 μM). Finally, the signals generated by their interactions were analyzed. The results showed that LC13 TCR with an artificial interchain disulfide bond was only bound to its corresponding antigen pMHC complex, and did not bind to other unrelated antigens including A0201: KLVALGI-NAV (SEQ ID NO.: 54), A0201: SLLMWITQC (SEQ ID NO.: 55) A0201: GILGFVFTL (SEQ ID NO.: 56), A0101: EVDPIGHLY (SEQ ID NO.: 57), A1101: SSCSSCPLSK (SEQ ID NO.: 58) and A2402: KYKDYFPVI (SEQ ID NO.: 59).

Example 5 1G4 Molecule with an Introduced Artificial Interchain Disulfide Bond Between the 53$^{rd}$ Position of TRAC*01 Exon 1 and 54$^{th}$ Position of TRBC1*01 or TRBC2*01 Exon 1

The arginine at position 53 of TRAC*01 exon 1 of TCR molecule 1G4 against antigen short peptide HLA-A2/SLL-MWITQC (SEQ ID NO.:55) (NY-ESO-1 tumor specific antigen) was mutated into cysteine and the serine at position 54 of TRBC1*01 or TRBC2*01 exon 1 was mutated into cysteine, thereby forming an artificial interchain disulfide bond.

Mutations were carried out using the primers and the PCR procedure described in Example 1. The α-chain and β-chain extracellular amino acid sequences of the mutated TCR molecule 1G4 are shown in FIGS. 7a and 7b, respectively, and their corresponding nucleotide sequences are shown in FIGS. 8a and 8b, respectively. The introduced cysteine residues are bolded and underlined.

Figure 74:
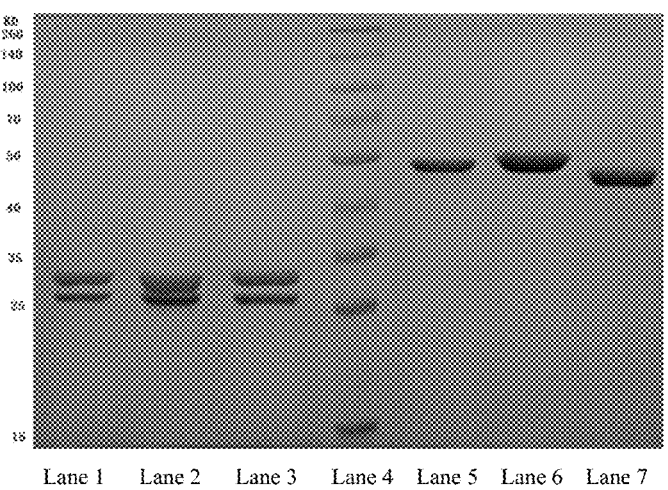
FIG. 74 shows reducing and non-reducing gel electrophoresis of 1G4TCR molecules with an introduced artificial interchain disulfide bond, wherein Lane 4 is molecular weight marker.

The 1G4 TCR was expressed, refolded and purified using the method described in Example 2. The elution curve of the second purification step was shown in FIG. 9. The components with peak were analyzed by Coomassie bright blue-stained SDS-PAGE, and the reducing and non-reducing gel electrophoresis were shown in lane 2 and lane 6 of FIG. 74. According to the elution peak and the gel electrophoresis, it was found that the elution peak was a soluble TCR molecule linked by an artificial interchain disulfide bond. The molecule was stable in SDS gel and formed separate α and β chains after reduction.

The purity of the 1G4 TCR protein was determined according to the method described in Example 2 and the yield thereof was calculated. As shown in FIG. 10, the HPLC elution peak of the 1G4 TCR molecule having an artificial interchain disulfide bond of the present invention was single and symmetrical. Its yield reached 40%.

The stability of the 1G4 TCR having an artificial interchain disulfide bond was determined using the method described in Example 3. The DSC thermogram was shown in FIG. 11 and its Tm value was 55.21° C. The thermogram could reflect that at room temperature, even at a temperature of 47-48° C., the TCR molecules containing the artificial interchain disulfide bond of the present invention could maintain proper folding and maintain proper activity, indicating that their stability was very high.

The binding activity and specificity of the 1G4 TCR protein to its corresponding antigen pMHC complex were examined by the method described in Example 4. The binding curve was obtained as shown in FIG. 12 with a KD value of 6.96 μM. It can be seen from this binding curve that the decrease in concentration did not affect the binding of the stable TCR molecules of the invention to its corresponding antigens. The TCR molecules at a low concentration exhibited the same binding activity as that at a high concentration. And it also demonstrated from another aspect that the TCR having the artificial interchain disulfide bond of the present invention was relatively stable.

At the same time, the TCR molecules of the present invention were also highly specific and only bonded to their corresponding pMHC complexes, and did not bind to other unrelated antigens including B4405: EEYLKAWTF(SEQ ID NO.:49), A0201: GILGFVFTL(SEQ ID NO.:56), A0101: EVDPIGHLY(SEQ ID NO.:57), A1101: SSCSSCPLSK (SEQ ID NO.:58) and A2402: KYKDYFPVI(SEQ ID NO.: 59).

Example 6 JM22 Molecule with an Introduced Artificial Interchain Disulfide Bond Between the 53$^{rd}$ Position of TRAC*01 Exon 1 and 54$^{th}$ Position of TRBC1*01 or TRBC2*01 Exon 1

The arginine at position 53 of TRAC*01 exon 1 of TCR molecule JM22 against antigen short peptide HLA-A2/GILGFVFTL (SEQ ID NO.:56) (from the influenza virus matrix protein) was mutated into cysteine and the serine at position 54 of TRBC1*01 or TRBC2*01 exon 1 was mutated into cysteine, thereby forming an artificial interchain disulfide bond.

Mutations were carried out using the primers and the PCR procedure described in Example 1. The α-chain and β-chain extracellular amino acid sequences of the mutated TCR molecule JM22 are shown in FIGS. 13a and 13b, respectively, and their corresponding nucleotide sequences are shown in FIGS. 14a and 14b, respectively. The introduced cysteine residues are bolded and underlined.

Figure 75:
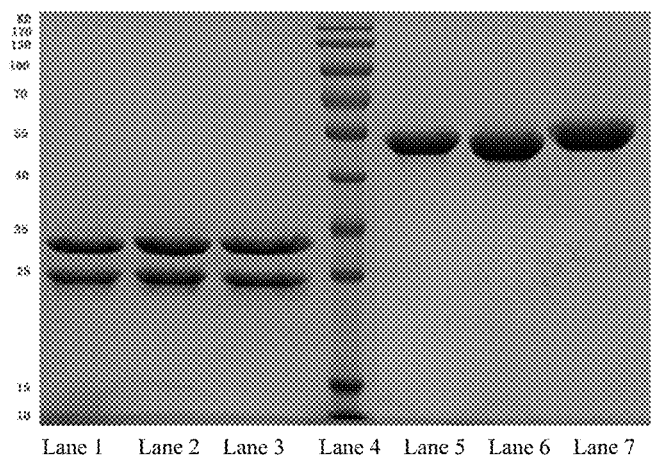
FIG. 75 shows reducing and non-reducing gel electrophoresis of JM22TCR molecules with an introduced artificial interchain disulfide bond, wherein Lane 4 is molecular weight marker.

The JM22 TCR was expressed, refolded and purified using the method described in Example 2. The elution curve of the second purification step was shown in FIG. 15. The components with peak were analyzed by Coomassie bright blue-stained SDS-PAGE, and the reducing and non-reducing gel electrophoresis were shown in lane 2 and lane 6 of FIG. 75. According to the elution peak and the gel electrophoresis, it was found that the elution peak was a soluble TCR molecule linked by an artificial interchain disulfide bond. The molecule was stable in SDS gel and formed separate α and β chains after reduction.

The purity of the JM22 TCR protein was determined according to the method described in Example 2 and the yield thereof was calculated. The SEC spectrum obtained is shown in FIG. 16, and the HPLC elution peak of the JM22 TCR molecule having an artificial interchain disulfide bond of the present invention was single and symmetrical. Its yield reached 31.65%.

The stability of the JM22 TCR having an artificial interchain disulfide bond was determined using the method described in Example 3. The DSC thermogram was shown in FIG. 17 and its Tm value was 49.06° C. The thermogram could reflect that at room temperature, even at a temperature of 40° C., the TCR molecules containing the artificial interchain disulfide bond of the present invention could maintain proper folding and maintain proper activity, indicating that their stability was very high.

The binding activity and specificity of the JM22 TCR protein to its corresponding antigen pMHC complex were examined by the method described in Example 4. The binding curve was obtained as shown in FIG. 18 with a KD value of 7.14 μM. It can be seen from this binding curve that the decrease in concentration did not affect the binding of the stable TCR molecules of the invention to its corresponding antigens. The TCR molecules at a low concentration exhibited the same binding activity as that at a high concentration. And it also demonstrated from another aspect that the TCR having the artificial interchain disulfide bond of the present invention was relatively stable.

At the same time, the TCR molecules of the present invention were also highly specific and only bonded to their corresponding pMHC complexes, and did not bind to other unrelated antigens including B4405: EEYLKAWTF(SEQ ID NO.:49), A0201: SLLMWITQC(SEQ ID NO.:55), A0101: EVDPIGHLY(SEQ ID NO.:57), A1101: SSCSS-CPLSK(SEQ ID NO.:58) and A2402: KYKDYFPVI(SEQ ID NO.:59).

Example 7 MGA3 Molecule with an Introduced Artificial Interchain Disulfide Bond Between the 53$^{rd}$ Position of TRAC*01 Exon 1 and 54$^{th}$ Position of TRBC1*01 or TRBC2*01 Exon 1

The arginine at position 53 of TRAC*01 exon 1 of TCR molecule MGA3 against antigen short peptide HLA-A1: EVDPIGHLY(SEQ ID NO.:57) (MageA3 tumor specific antigen) was mutated into cysteine and the serine at position 54 of TRBC1*01 or TRBC2*01 exon 1 was mutated into cysteine, thereby forming an artificial interchain disulfide bond.

Mutations were carried out using the primers and the PCR procedure described in Example 1. The α-chain and β-chain extracellular amino acid sequences of the mutated TCR molecule MGA3 are shown in FIGS. 19a and 19b, respectively, and their corresponding nucleotide sequences are shown in FIGS. 20a and 20b, respectively. The introduced cysteine residues are bolded and underlined.

Figure 76:
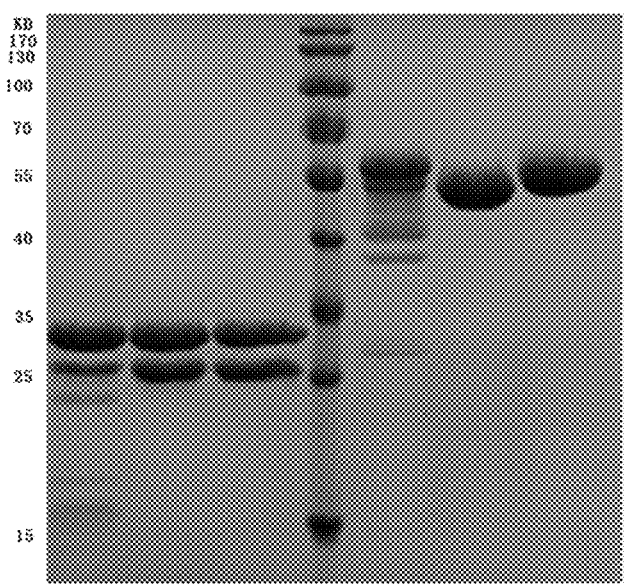
FIG. 76 shows reducing and non-reducing gel electrophoresis of MGA3TCR molecules with an introduced artificial interchain disulfide bond, wherein Lane 4 is molecular weight marker.

The MGA3 TCR was expressed, refolded and purified using the method described in Example 2. The elution curve of the second purification step was shown in FIG. 21. The components with peak were analyzed by Coomassie bright blue-stained SDS-PAGE, and the reducing and non-reducing gel electrophoresis were shown in lane 2 and lane 6 of FIG. 76. According to the elution peak and the gel electrophoresis, it was found that the elution peak was a soluble TCR molecule linked by an artificial interchain disulfide bond. The molecule was stable in SDS gel and formed separate α and β chains after reduction.

The purity of the MGA3 TCR protein was determined according to the method described in Example 2 and the yield thereof was calculated. As shown in FIG. 22, the HPLC elution peak of the MGA3 TCR molecule having an artificial interchain disulfide bond of the present invention was single and symmetrical. Its yield reached 30.14%.

The stability of the MGA3 TCR having an artificial interchain disulfide bond was determined using the method described in Example 3. The DSC thermogram was shown in FIG. 23 and its Tm value was 53.86° C. The thermogram could reflect that at room temperature, even at a temperature of 45-46° C., the TCR molecules containing the artificial interchain disulfide bond of the present invention could maintain proper folding and maintain proper activity, indicating that their stability was very high.

The binding activity and specificity of the MGA3 TCR protein to its corresponding antigen pMHC complex were examined by the method described in Example 4. The binding curve was obtained as shown in FIG. 24 with a KD value of 1.42 μM. It can be seen from this binding curve that the decrease in concentration did not affect the binding of the stable TCR molecules of the invention to its corresponding antigens. The TCR molecules at a low concentration exhibited the same binding activity as that at a high concentration. And it also demonstrated from another aspect that the TCR having the artificial interchain disulfide bond of the present invention was relatively stable.

At the same time, the TCR molecules of the present invention were also highly specific and only bonded to their corresponding pMHC complexes, and did not bind to other unrelated antigens including B4405: EEYLKAWTF(SEQ ID NO.:49), A0201: SLLMWITQC(SEQ ID NO.:55), A0201: GILGFVFTL(SEQ ID NO.:56), A1101: SSCSS-CPLSK(SEQ ID NO.:58) and A2402: KYKDYFPVI(SEQ ID NO.:59).

Example 8 Performance Determination of a Molecule with an Introduced Artificial Interchain Disulfide Bond Between the 89$^{th}$ Position of TRAC*01 Exon 1 and 19$^{th}$ Position of TRBC1*01 or TRBC2*01 Exon 1

The proline at position 89 of TRAC*01 exon 1 of TCR molecules LC13, 1G4, JM22 and MGA3 was mutated into cysteine respectively and the alanine at position 19 of TRBC1*01 or TRBC2*01 exon 1 was mutated into cysteine, thereby form an artificial interchain disulfide bond.

When the proline at position 89 of TRAC*01 exon 1 of above TCRs was mutated into cysteine, the primers were designed as follows:

```
5'-3'
                                      (SEQ ID NO.: 60)
CGGAAGATACGTTCTTCTGCAGCCCAGAAAGTTCC (SEQ ID NO.: 61)
GGAACTTTCTGGGCTGCAGAAGAACGTATCTTCCG
```

When the alanine at position 19 of TRBC*101 or TRBC2*01 exon 1 of above TCRs was mutated into cysteine, the primers were designed as follows:

```
5'-3'
                                      (SEQ ID NO.: 62)
GTTTTTGAACCGAGCGAATGCGAAATTAGCCATACC (SEQ ID NO.: 63)
GGTATGGCTAATTTCGCATTCGCTCGGTTCAAAAAC
```

The PCR, refolding and performance tests of the TCRs were performed according to the methods described in Examples 1 to 4.

The α-chain and β-chain extracellular amino acid sequences of the mutated TCR molecule for LC13 are shown in FIGS. 25a and 25b, respectively, and their corresponding nucleotide sequences are shown in FIGS. 26a and 26b, respectively. The introduced cysteine residues are bolded and underlined. The elution curve and the gel graph are shown in FIG. 27 and lane 3 and lane 7 of FIG. 73. As shown in FIG. 28, the HPLC elution peak was single and symmetrical. The protein refolding yield was also quite high, reaching 42.82%. The Tm value was 55.65° C. The corresponding DSC spectrum is shown in FIG. 29. The binding curve of the LC13 TCR molecule to its corresponding antigen is shown in FIG. 30. The KD value was 10.3 μM.

The α-chain and β-chain extracellular amino acid sequences of the mutated TCR molecule for 1G4 are shown in FIGS. 31a and 31b, respectively, and their corresponding nucleotide sequences are shown in FIGS. 32a and 32b, respectively. The introduced cysteine residues are bolded and underlined. The elution curve and the gel graph are shown in FIG. 33 and lane 3 and lane 7 of FIG. 74. As shown in FIG. 34, the HPLC elution peak was single and symmetrical. The protein refolding yield was also quite high, reaching 48%. The Tm value was 55.82° C. The corresponding DSC spectrum is shown in FIG. 35. The binding curve of the 1G4 TCR molecule to its corresponding antigen is shown in FIG. 36. The KD value was 6.63 μM.

The α-chain and β-chain extracellular amino acid sequences of the mutated TCR molecule for JM22 are shown in FIGS. 37a and 37b, respectively, and their corresponding nucleotide sequences are shown in FIGS. 38a and 38b, respectively. The introduced cysteine residues are bolded and underlined. The elution curve and the gel graph are shown in FIG. 39 and lane 3 and lane 7 of FIG. 75. As shown in FIG. 40, the HPLC elution peak was single and symmetrical. The protein refolding yield reached 14.93%6. The Tm value was 51.08° C. The corresponding DSC spectrum is shown in FIG. 41. The binding curve of the JM22 TCR molecule to its corresponding antigen is shown in FIG. 42. The KD value is 7.61 μM.

The α-chain and β-chain extracellular amino acid sequences of the mutated TCR molecule for MGA3 are shown in FIGS. 43a and 43b, respectively, and their corresponding nucleotide sequences are shown in FIGS. 44a and 44b, respectively. The introduced cysteine residues are bolded and underlined. The elution curve and the gel graph are shown in FIG. 45 and lane 3 and lane 7 of FIG. 76. As shown in FIG. 46, the HPLC elution peak was single and symmetrical. The protein refolding yield reached 13.76%. The Tm value was 54.49° C. The corresponding DSC spectrum is shown in FIG. 47. The binding curve of the MGA3 TCR molecule to its corresponding antigen is shown in FIG. 48. The KD value was 2.04 μM.

The elution curves and the SDS gel diagram of the above molecules showed that the elution peak components were the soluble TCR molecule linked by the artificial interchain disulfide bond of the present invention, which was stable in the SDS gel and was reduced to form separate α and β chains. The protein refolding yields were also high. In addition, the Tm values of the TCR molecules linked by the artificial interchain disulfide bonds of the present invention were also high (all of which were greater than 45° C.), indicating that they could maintain proper folding and desired activity at a higher temperature and showing that its stability was very high. At the same time, the binding curves of the TCR molecules to its original ligands showed that the decrease in TCR concentration did not affect the binding to their ligand, and it also demonstrated from other aspect that the TCR molecules having the interchain disulfide bond of the present invention were stable. In the specificity tests, these TCR molecules introduced artificial interchain disulfide bonds also showed good specificity.

Example 9 Performance Determination of a Molecule with an Introduced Artificial Interchain Disulfide Bond Between the 10$^{th}$ Position of TRAC*01 Exon 1 and 20$^{th}$ Position of TRBC1*01 or TRBC2*01 Exon 1

The tyrosine at position 10 of TRAC*01 exon 1 of TCR molecules LC13, 1G4, JM22 and MGA3 was mutated into cysteine respectively and the glutamic acid at position 20 of TRBC1*01 or TRBC2*01 exon 1 was mutated into cysteine, thereby forming an artificial interchain disulfide bond.

When the tyrosine at position 10 of TRAC*01 exon 1 of above TCRs was mutated into cysteine, the primers were designed as follows:

```
5'-3'
                              (SEQ ID NO.: 64)
CCGGATCCGGCCGTTTGCCAGCTGCGTGATAGC (SEQ ID NO.: 65)
GCTATCACGCAGCTGGCAAACGGCCGGATCCGG
```

When the glutamic acid at position 20 of TRBC1*01 or TRBC2*01 exon 1 of above TCRs was mutated into cysteine, the primers were designed as follows:

```
5'-3'
                              (SEQ ID NO.: 66)
GAACCGAGCGAAGCGTGCATTAGCCATACCCAG (SEQ ID NO.: 67)
CTGGGTATGGCTAATGCACGCTTCGCTCGGTTC
```

The PCR, refolding and performance tests of the TCR were performed according to the methods described in Examples 1 to 4.

The α-chain and β-chain extracellular amino acid sequences of the mutated TCR molecule for LC13 are shown in FIGS. 49a and 49b, respectively, and their corresponding nucleotide sequences are shown in FIGS. 50a and 50b, respectively. The introduced cysteine residues are bolded and underlined. The elution curve and the gel graph were shown in FIG. 51 and lane 1 and lane 5 of FIG. 73. As shown in FIG. 52, the HPLC elution peak was single and symmetrical. The protein refolding yield reached 16.19%. The Tm value was 50.42° C. The corresponding DSC spectrum is shown in FIG. 53. The binding curve of the LC13 TCR molecule to its corresponding antigen is shown in FIG. 54. The KD value was 10 μM.

The α-chain and β-chain extracellular amino acid sequences of the mutated TCR molecule for 1G4 are shown in FIGS. 55a and 55b, respectively, and their corresponding nucleotide sequences are shown in FIGS. 56a and 56b, respectively. The introduced cysteine residues are bolded and underlined. The elution curve and the gel graph were shown in FIG. 57 and lane 1 and lane 5 of FIG. 74. As shown in FIG. 58, the HPLC elution peak was single and symmetrical. The protein refolding yield reached 29%. The Tm value was 54.68° C. The corresponding DSC spectrum is shown in FIG. 59. The binding curve of the 1 G4 TCR molecule to its corresponding antigen is shown in FIG. 60. The KD value is 6.68 μM.

The α-chain and β-chain extracellular amino acid sequences of the mutated TCR molecule for JM22 are shown in FIGS. 61a and 61b, respectively, and their corresponding nucleotide sequences are shown in FIGS. 62a and 62b, respectively. The introduced cysteine residues are bolded and underlined. The elution curve and the gel graph were shown in FIG. 63 and lane 1 and lane 5 of FIG. 75. As shown in FIG. 64, the HPLC elution peak was single and symmetrical. The protein refolding yield reached 10.50%. The Tm value was 49.95° C. The corresponding DSC spectrum is shown in FIG. 65. The binding curve of the JM22 TCR molecule to its corresponding antigen is shown in FIG. 66. The KD value is 5.54 μM.

The α-chain and β-chain extracellular amino acid sequences of the mutated TCR molecule for MGA3 are shown in FIGS. 67a and 67b, respectively, and their corresponding nucleotide sequences are shown in FIGS. 68a and 68b, respectively. The introduced cysteine residues are bolded and underlined. The elution curve and the gel graph were shown in FIG. 69 and lane 1 and lane 5 of FIG. 76. As shown in FIG. 70, the HPLC elution peak was single and symmetrical. The protein refolding yield reached 4.53%. The Tm value was 53.38° C. The corresponding DSC spectrum is shown in FIG. 71. The binding curve of the MGA3 TCR molecule to its corresponding antigen is shown in FIG. 72. The KD value is 3.45 μM.

The elution curves and the SDS gel diagram of the above molecules showed that the elution peak components were the soluble TCR molecule linked by the artificial interchain disulfide bond of the present invention, which was stable in the SDS gel and was reduced to form separate α and β chains. The protein refolding yields were also high. In addition, the Tm values of the TCR molecules linked by the artificial interchain disulfide bonds of the present invention were also high (all of which were greater than 45° C.), indicating that they could maintain proper folding and desired activity at a higher temperature and showing that its stability was very high. At the same time, the binding curves of the TCR molecules to its original ligands showed that the decrease in TCR concentration did not affect the binding to their ligand, and it also demonstrated from other aspect that the TCR molecules having the interchain disulfide bond of the present invention were stable. In the specificity tests, these TCR molecules introduced artificial interchain disulfide bonds also showed good specificity.

The above examples demonstrate that the TCR molecules of the present invention obtained by introducing the artificial interchain disulfide bond of the present invention into the TCR constant region are highly stable and have a Tm value greater than 45° C. and can be well renatured, refolded and purified. The yields after refolding are high while the TCRs retain the ability to specifically bind to their original ligands.

All documents referred to in the present invention are incorporated by reference as if each reference is cited alone as a reference in the present application. In addition, it should be understood that after reading the teachings of the present invention described above, a skilled person in the art can make various changes or modifications of the invention, and these equivalent forms also fall into the scope as defined by the appended claims of the present application.

The invention claimed is:

1. A T cell receptor (TCR) which has an artificial interchain disulfide bond formed by introducing a cysteine residue into TCR α chain and β chain constant region, wherein the TCR having an artificial interchain disulfide bond has a Tm≥45° C.;
wherein the cysteine residues that form an artificial interchain disulfide bond are at a substitution position selected from the group consisting of:
R53C in Exon 1 of TRAC*01, and S54C in Exon 1 of TRBC1*01 or TRBC2*01; and
Y10C in Exon 1 of TRAC*01, and E20C in Exon 1 of TRBC1*01 or TRBC2*01;
wherein the TCR comprises: (i) all or part of the TCR α chain other than its transmembrane domain, and (ii) all or part of the TCR β chain other than its transmembrane domain, wherein (i) and (ii) each comprises a functional variable domain and at least a portion of a constant domain of the TCR chain, wherein a conjugate is linked to the C- or N-terminus of the TCR α and/or β chains, and wherein the conjugate is a detectable marker or a therapeutic agent.

2. The TCR of claim 1, wherein the TCR is soluble.

3. The TCR of claim 1, wherein the TCR does not have any natural interchain disulfide bond.

4. The TCR of claim 3, wherein the C-terminus of the native TCR is truncated in the TCR so that a cysteine residue for forming a natural interchain disulfide bond is removed.

5. The TCR of claim 3, wherein a cysteine residue for forming a natural interchain disulfide bond is substituted with another residue.

6. The TCR of claim 1, wherein the TCR β chain constant region has no unpaired cysteine residue.

7. The TCR of claim 1, wherein the therapeutic agent bound with the TCR is an antibody against CD3 which is linked at C- or N- terminal of the TCR α and/or β chains.

8. A nucleic acid molecule comprising a sequence encoding an α chain and/or a β chain of the TCR according to claim 1, or its complementary sequence.

9. A vector comprising a nucleic acid molecule of claim 8.

10. A host cell or a genetically engineered cell which comprises a vector comprising a nucleic acid molecule of claim 8 or in which an exogenous nucleic acid molecule of claim 8 is integrated in a chromosome.

11. An isolated cell which expresses a TCR, wherein the cell is a bacteria and the TCR has an artificial interchain disulfide bond formed by introducing a cysteine residue into TCR a chain and b chain constant region, wherein the TCR having an artificial interchain disulfide bond has a Tm≥45° C.;
wherein the cysteine residues that form an artificial interchain disulfide bond are at a substitution position selected from the group consisting of:
R53C in Exon 1 of TRAC*01, and S54C in Exon 1 of TRBC1*01 or TRBC2*01; and
Y10C in Exon 1 of TRAC*01, and E20C in Exon 1 of TRBC1*01 or TRBC2*01;
wherein the TCR comprises: (i) all or part of the TCR α chain other than its transmembrane domain, and (ii) all or part of the TCR β chain other than its transmembrane domain, wherein (i) and (ii) each comprises a functional variable domain and at least a portion of a constant domain of the TCR chain.

12. A method for preparing a TCR, which comprises:
(i) culturing the host cell of claim 10, thereby expressing an α chain and/or β chain of the TCR; and
(ii) isolating or purifying the α chain and/or β chain;
(iii) refolding the α chain and/or β chain, thereby obtaining the TCR.

13. A TCR complex comprising one or more TCR molecules of claim 1.

14. A pharmaceutical composition comprising a pharmaceutically acceptable carrier and a TCR of claim 1, or a TCR complex comprising one or more said TCR.

* * * * *